US012678496B2

(12) United States Patent
Massoud et al.

(10) Patent No.: US 12,678,496 B2
(45) Date of Patent: Jul. 14, 2026

(54) GOLD NANOPARTICLE INTRANASAL VACCINE COMPOSITIONS

(71) Applicant: The Board of Trustees of the Leland Stanford Junior University, Stanford, CA (US)

(72) Inventors: Tarik F. Massoud, Stanford, CA (US); Ramasamy Paulmurugan, Stanford, CA (US); Uday Sukumar, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 684 days.

(21) Appl. No.: 18/018,316

(22) PCT Filed: Jul. 30, 2021

(86) PCT No.: PCT/US2021/044052
§ 371 (c)(1),
(2) Date: Jan. 27, 2023

(87) PCT Pub. No.: WO2022/026917
PCT Pub. Date: Feb. 3, 2022

(65) Prior Publication Data
US 2023/0277646 A1 Sep. 7, 2023

Related U.S. Application Data

(60) Provisional application No. 63/059,845, filed on Jul. 31, 2020.

(51) Int. Cl.
*A61K 39/12* (2006.01)
*A61P 31/14* (2006.01)
(Continued)

(52) U.S. Cl.
CPC .............. *A61K 39/12* (2013.01); *A61P 31/14* (2018.01); *A61K 2039/55505* (2013.01);
(Continued)

(58) Field of Classification Search
None
See application file for complete search history.

(56) References Cited

U.S. PATENT DOCUMENTS 8,815,295 B1 8/2014 Singh
8,846,026 B2 9/2014 Plebanski
(Continued)

FOREIGN PATENT DOCUMENTS

WO 2015013673 A1 1/2015
WO 2018115527 A3 8/2018
WO WO-2022026917 A1 * 2/2022 ........... C07K 14/005

OTHER PUBLICATIONS

Zhou et al. (Biomaterials. 2008; 29: 111-117).*
(Continued)

*Primary Examiner* — Shanon A. Foley
(74) *Attorney, Agent, or Firm* — KDW Firm PLLC

(57) ABSTRACT

Provided herein, inter alia, are complexes comprising nanoparticles attached to viral proteins or nucleic acids encoding said viral proteins. Methods for making and using said complexes are provided. Compositions including the complexes are contemplated to be useful for treating and/or preventing viral infections.

4 Claims, 56 Drawing Sheets

Anti-Spike IgG

Time point of Serum Collection (weeks)
(1:500 dilution)

BALBc    C57BL/6J

(51) Int. Cl.
| | |
|---|---|
| *A61K 39/00* | (2006.01) |
| *B82Y 5/00* | (2011.01) |
| *B82Y 30/00* | (2011.01) |

(52) U.S. Cl.
CPC ....... *A61K 2039/55555* (2013.01); *B82Y 5/00* (2013.01); *B82Y 30/00* (2013.01)

(56) References Cited

U.S. PATENT DOCUMENTS

| | | | |
|---|---|---|---|
| 2018/0273948 A1 | 9/2018 | Kadiyala | |
| 2019/0374478 A1* | 12/2019 | Boisselier | A61P 27/06 |
| 2023/0277646 A1* | 9/2023 | Massoud | A61K 39/12 |
| | | | 424/186.1 |

OTHER PUBLICATIONS

Kumar et al. (Human Gene Therapy. 202; 13: 1415-1425).*
Wu et al. (Nature. Available online: Feb. 3, 2020; 579 (7798): 265-269).*
Buchholz et al. (PNAS. 2004; 101 (26): 9804-9809).*
Shi et al. (Molecular Immunology. 2006; 43: 1791-1798).*
Wang et al. (Nanomedicine: Nanotechnology, Biology, and Medicine. 2018; 14: 1349-1360).*
Facchi et al. (Current Medicinal Chemistry. 2017; 24: 2701-2735).*
Al-Halifa et al., "Nanoparticle-Based Vaccines Against Respiratory Viruses," Frontiers in Immunology, vol. 10, Article 22: 11 pages (Jan. 2019).
Jackson et al., "An mRNA Vaccine against SARS-COV-2—Preliminary Report," The New England Journal of Medicine, vol. 383: 1920-1931 (2020).
Kunda et al., "Nanocarriers Targeting Dendritic Cells for Pulmonary Vaccine Delivery," Pharmaceutical Research, vol. 30: 325-341 (2013).
Sukumar et al., "Intranasal Delivery of Targeted Polyfunctional Gold-Iron Oxide Nanoparticles Loaded with Therapeutic microRNAs for Combined Theranostic Multimodality Imaging and Presensitization of Glioblastoma to Temozolomide," Biomaterials, vol. 218: 35 pages (Jul. 2019).
Extended European Search Report issued in EP Application No. 21850622.8, dated Aug. 22, 2024, 11 pages.
Wang, Fuzhou et al. "An Evidence Based Perspective on mRNA-SARS-CoV-2 Vaccine Development." Medical science monitor : international medical journal of experimental and clinical research vol. 26 e924700. May 5, 2020.
International Search Report and Written Opinion for the International Patent Application No. PCT/US2021/44052, mailed Dec. 22, 2021, 16 pages.
Abrica-González et al., "Gold nanoparticles with chitosan, N-acylated chitosan, and chitosan oligosaccharide as DNA carriers," Nanoscale Research Letters, vol. 14: 258 (2019).
Shin et al., "COVID-19 vaccine development and a potential nanomaterial path forward," Nature Nanotechnology, vol. 15: 646-655 (Aug. 2020).

* cited by examiner

Anti-Spike IgG

Time point of Serum Collection (weeks)
(1:500 dilution)

BALBc    C57BL/6J

Anti-Spike IgM

Time point of Serum Collection (weeks)
(1:500 dilution)

BALBc    C57BL/6J

Time course of spike antigen-specific IgA response to
COVID-19 mRNA vaccine

Moderna
Pfizer- BioNTech

Time course of spike antigen-specific IgG response to
COVID-19 mRNA vaccine

Moderna
Pfizer- BioNTech

Lungs pDNA treated mice
Spike DNA treated mice

FIG. 19B

GOLD NANOPARTICLE INTRANASAL VACCINE COMPOSITIONS

CROSS-REFERENCE TO RELATED APPLICATIONS

This application is a national phase entry of, claims the benefit of and priority to previously filed International Patent Application No. PCT/US21/044052, entitled "VACCINE COMPOSITIONS AND METHODS OF USE THEREOF", filed Jul. 30, 2021, which claims priority to U.S. Provisional Application No. 63/059,845, filed Jul. 31, 2020, both of which are hereby incorporated by reference in their entireties and for all purposes.

BACKGROUND

The World Health Organization announced on Mar. 11, 2020 that COVID-19 is a pandemic disease caused by a novel strain of coronavirus called SARS-CoV-2. This virus mainly causes respiratory tract disease and pneumonia in humans by infecting cells expressing a higher level of angiotensin-converting enzyme 2 (ACE2) receptor, which the virus uses to gain intracellular entry.[1-2]

In brief, the body's adaptive immune system can learn to recognize new invading pathogens. SARS-CoV-2 uses its surface spike glycoprotein (S) to lock onto ACE2 receptors on human cell surfaces.[2-3] Once inside, virus fuses with its surrounding vesicle to release its ribonucleic acid (RNA), viral RNA is translated into proteins, virus assembly occurs, and more viruses are released to infect other host cells.[4] An infected patient can then initiate an immune response, whereby specialized "antigen presenting cells" engulf the virus and display portions of it to activate T helper cells. T helper cells then enable other immune responses: B cells make antibodies that can block the virus from infecting cells, and also mark the virus for destruction; and cytotoxic T cells identify and destroy virus-infected cells. Long-lived 'memory' B and T cells that recognize the virus can patrol the body for subsequent months or years, providing immunity.[5]

Anti-COVID-19 treatments and preventions are immediate priorities: The current pandemic SARS-CoV-2 strain is new, and limited clinical and immunological information are available to help in the development of drugs or vaccines that can treat and protect patients with COVID-19. It is vital and of immediate importance to develop safe and effective vaccines that provide protection from SARS-CoV-2.

All vaccines aim to expose the body to an antigen that will not cause disease, but will provoke an immune response that can block or kill the virus if a person becomes infected. As of Apr. 30, 2020, more than 90 vaccines of eight broad types were being developed against SARS-CoV-2 across the world: (1) Virus vaccines (weakened or inactivated viruses). (2) Nucleic acid vaccines (DNA or RNA based). (3) Viral vector vaccines (replicating and non-replicating viral vectors). (4) Protein based vaccines (protein subunits and virus-like particles). There are many relative merits and demerits for these strategies.[6] Conventional vaccine approaches, such as live attenuated, inactivated and subunit vaccines of pathogens, provide durable protection against a variety of dangerous diseases by directly mimicking the natural pathogen without causing the disease. However, since SARS-CoV-2 is a new viral strain that is spreading very rapidly and globally, the traditional vaccine development pipeline may not provide an immediate solution. Rapid development and large-scale deployment strategies are required for those conventional approaches.

SARS-CoV-2 is similar to SARS-CoV and MERS-CoV viruses with regard to their biological profiles and clinical presentations.[7] In all these viruses, the S protein is the major inducer of neutralizing antibodies.[8-11] Recombinant adenovirus-based vaccine expressing S protein of MERS-CoV induces systemic IgG, secretory IgA, and lung resident memory T cell responses when administered intranasally (IN) into BALB/c mice, providing long-lasting neutralizing immunity to spike pseudotyped MERS virus, thereby suggesting that this IN vaccine may confer protection against MERS-CoV.[12] Elsewhere, the possibility of developing a universal CoV vaccine was evaluated based on T cell epitope similarities of SARS-CoV and MERS-CoV, suggesting the potential for cross-reactivity among coronaviruses.[13] Since SARS-CoV-2 shares high genetic similarity with the SARS-CoV, vaccines developed for SARS-CoV may exhibit cross-reactivity to SARS-CoV-2.[13-14] The nucleocapsid (N) protein, membrane (M) protein, as well as the potential B cell epitopes of the E protein of MERS-Cov have also been suggested as probable immuno-protective epitopes that induce both T cell and neutralizing antibody responses.[15-16] Attempts at using vaccines against SARS-CoV and MERS-CoV have achieved limited success. Even though they possess significant genetic homology, there are several variations in the amino acid sequences of the SARS-CoV-2 surface antigens. Therefore, there is a need in the art to develop vaccines against SARS-CoV-2 as well as other pulmonary viruses. Provided herein are solutions to this and other needs in the art.

BRIEF SUMMARY

In an aspect is provided a complex including: (a) a nanoparticle including a gold core; and (b) a pulmonary viral protein or fragment thereof, or a nucleic acid encoding the pulmonary viral protein or fragment thereof, wherein the pulmonary viral protein or nucleic acid is attached to the nanoparticle.

In an aspect is provided a vaccine composition including a complex provided herein including embodiments thereof and a pharmaceutically acceptable excipient.

In an aspect is provided a method of treating or preventing a pulmonary viral disease in a subject in need of such treatment or prevention, the method including administering a therapeutically or prophylactically effective amount of a complex provided herein including embodiments thereof to the subject.

In another aspect a method of treating or preventing a pulmonary viral disease in a subject in need of such treatment or prevention is provided, the method including administering a therapeutically or prophylactically effective amount of a vaccine composition provided herein including embodiments thereof to the subject.

In an aspect is provided a method for immunizing a subject susceptible to a pulmonary viral disease, the method including administering a complex provided herein including embodiments thereof to the subject, under conditions such that antibodies that bind to the pulmonary viral protein or fragment thereof are produced.

In an aspect is provided a nanoparticle including a plurality of nucleic acids attached thereto and plurality of proteins attached thereto, wherein each of the plurality of nucleic acids encode for a different SARS-CoV-2 viral protein, and each of the plurality of proteins is a different SARS-CoV-2 viral protein.

In an aspect is provided a vaccine formulation including a nanoparticle as provided herein including embodiments thereof, and a pharmaceutically acceptable excipient.

In an aspect is provided a method of preventing or treating COVID-19 in a subject in need thereof, the method including administering to the subject a composition including an effective amount of a vaccine as provided herein including embodiments thereof, or a nanoparticle as provided herein including embodiments thereof, to a subject in need thereof.

In embodiments is provided a method of preventing or treating a SARS-CoV-2 viral infection in a subject in need thereof, the method including administering a composition including an effective amount of a vaccine as provided herein including embodiments thereof, or a nanoparticle as provided herein including embodiments thereof, to a subject in need thereof.

BRIEF DESCRIPTION OF THE DRAWINGS

FIG. 2A shows a transmission electron microscopy (TEM) image of PolyGION. FIG. 2B shows Energy-dispersive X-ray spectroscopy (EDX) analysis of PolyGION. FIG. 2C shows RNA loading efficiency of PolyGION-CD-CS. FIGS. 2D-2E show a DLS analysis of PolyGION-CD-CS nanoparticles for size (FIG. 2D) and zeta potential (FIG. 2E). FIG. 2F shows intracellular delivery of PolyGION-CD-CS-mRNA in A549 cells by Prussian blue staining.

FIG. 4A shows microCT images of control and animal treated using PolyGION-CD-CS-FLuc-mRNA; FIG. 4B shows BLI of animals imaged on the same day as microCT; and FIG. 4C shows ex vivo BLI of tissues extracted from animal of treatment group.

(FIG. 7A) Representative images of cells transfected with Au—CH Nanoparticles loaded with DNA encoding a luciferase reporter protein. Intensity of fluorescence is indicative of transfection efficiency. (FIG. 7B) Bar graph showing fluorescence intensity of the transfected cells.

(FIG. 8A) Representative images of cells transfected with Au—CH Nanoparticles loaded with various amounts of DNA encoding a luciferase reporter protein. (FIG. 8B) Number of events against Fluc-EGFP-Fluorescence intensity histogram showing the shift of stained cells dependent on the amount of DNA loaded on the nanoparticles. (FIG. 8C) Bar graph showing transfection efficiency of nanoparticles loaded with DNA, and dose dependent expression of loaded DNA as measured by fluorescence intensity.

(FIGS. 9A-9C) FE-SEM micrographs indicate uniform morphology of AuNS-chitosan and SC2 DNA; (FIG. 9D) Evaluation of DNA loading efficiency of AuNS-chitosan by gel retardation assay; (FIGS. 9E-9F) DLS results measured for zeta potential and particle size (nm) of SC2 vaccine loaded AuNS at different ratios; (FIG. 9G) Transfection efficiency of AuNS-chitosan evaluated by delivery of pcDNA-FLuc-eGFP plasmid by bioluminescence imaging; (FIG. 9H) Immunoblot analysis for expression of SC2 S protein transfected in HEK293T cells by AuNS-chitosan. The data are presented as mean±SEM; One-way ANOVA with Bonferroni post hoc test was used to draw significance of comparisons as indicated. Adjusted p-values were considered statistically significant if p-values <0.05 and the symbols indicating statistical significance were as follows—ns represents no-significant difference, * represents p<0.05,  represents p<0.01, * represents p<0.001 and **** represents p<0.0001 significance.

(FIG. 10B) Chemiluminescence based dot blot immunoassay for screening anti-SC2 antibody levels in serum collected from, (FIG. 10C) BALB/c and (FIG. 10D) C57BL/6J mice at different time points of treatment with their respective quantitative plots. The data are presented as mean±SEM. Two-way ANOVA was performed for multiple comparisons with Tukey T test determining confidence interval and the results are denoted by ns-represents no-significant difference, * for p<0.05,  for p<0.01, * for p<0.001 and **** for p<0.0001.

(FIG. 11C) Response in anti SC2 antibody levels in serum of two different treatment batches (each with n=5) indicates the consistent antibody response; (FIG. 11D) Comparison of anti-SC2 antibody levels generated in BALB/c mice administered with AuNS-chitosan loaded pDNA/pDNA-SC2 DNA vaccine with wild type and ACE-2 engineered C57BL/6J upon challenge with pseudovirus engineered with SC2-W and SC2-SA S proteins (*P<0.05,  P<0.01,  P<0.001, ** P<0.0001, ns: not significant); Antibody mediated immune responses after IN immunization of SC2 S protein DNA vaccine using AuNS-chitosan. Antibody responses in sera of immunized mice at different time points of treatment were evaluated using ELISA. ELISA assay measured against SC2 S protein-specific IgA (FIG. 11E), IgG (FIG.

Figure 1:
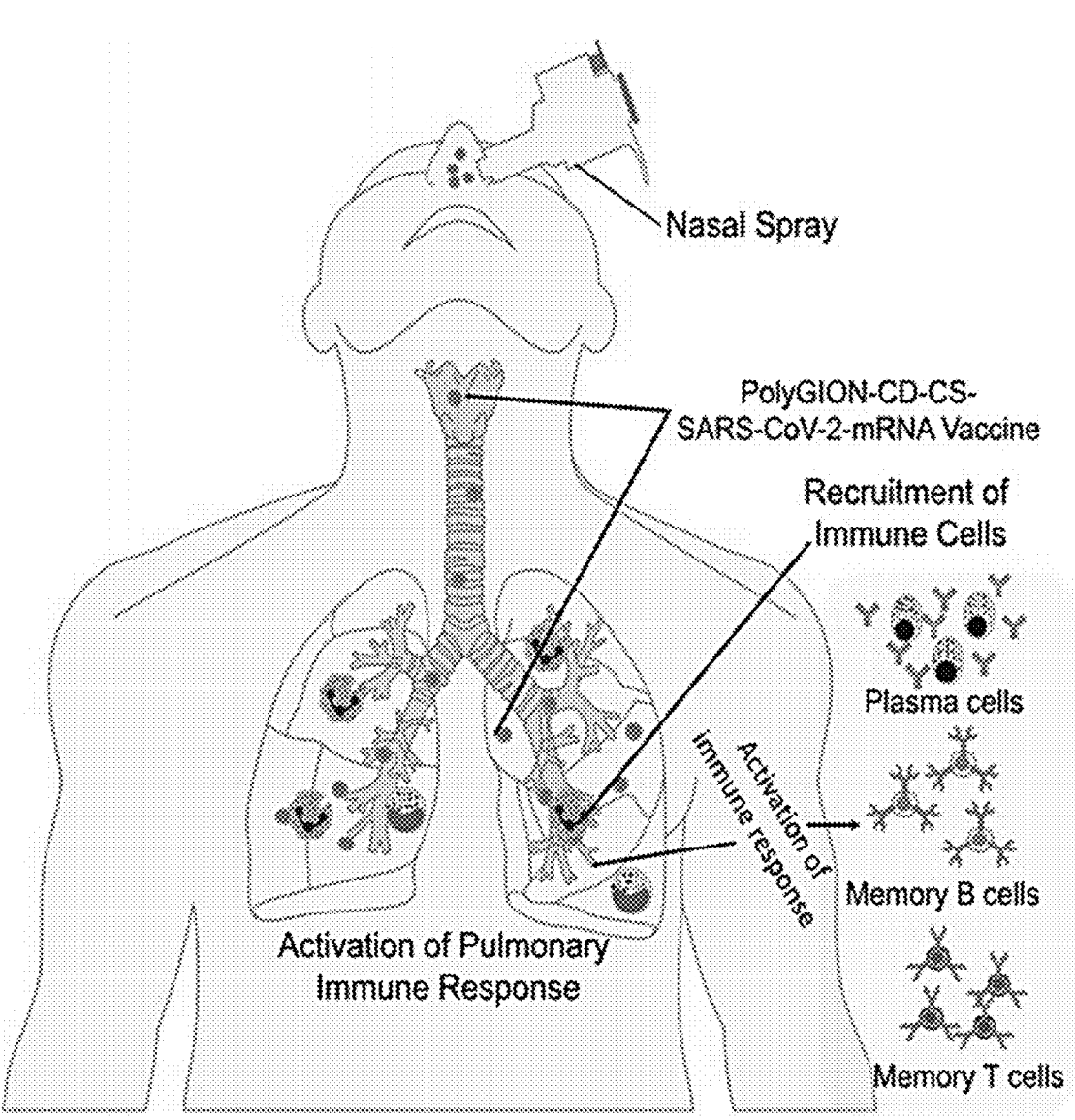
FIG. 1 is a schematic illustration of SARS-CoV-2 mRNA vaccine delivery using PolyGION-CD-CS nanoparticles (NPs) for activation of pulmonary immune responses.

11F) and IgM (FIG. 11G) levels. Data generated from pooled serum of 3-5 BALB/c and 3-5 C57BL/6J mice. All mice received a booster dose on Week 14 to evaluate mucosal and cell-mediated immune responses. The data are presented as mean±SEM. Two-way ANOVA was performed for multiple comparisons with Tukey T test determining confidence interval and the results are denoted by ns-represents no-significant difference, * for p<0.05,  for p<0.01, * for p<0.001 and **** for p<0.0001.

FIGS. 12A-13B show anti-S protein IgA (FIG. 12A) and IgG (FIG. 12B) responses induced by mRNA vaccines FIGS. 13A-13G show evaluation of the specificity of lentivirus expressing SC2 S protein as a pseudovirus to cells expressing ACE2 receptor. (FIG. 13A) Mechanism of SC2 transduction in cells; lentivirus expressing SC2 S protein and Fluc-ZsGreen reporter gene were engineered, and these pseudoviruses were transduced in control and ACE2 receptor expressing cells, and subsequent infectivity was quantified using bioluminescence imaging. (FIGS. 13B-13C) DNA vaccine-mediated induction of anti-SC2-S protein specific antibody evaluated for its neutralizing effect using engineered pseudovirus assessed by quantifying pseudovirus-mediated ZsGreen expression in the infected cells in the presence of neutralizing antibody from serum of mice treated with DNA vaccine; and (FIG. 13D) Neutralizing effect of serum collected at different time points after vaccination. Commercial antibody was used as positive (+) control. T1, T2, T3 indicates time point of serum collection, i.e., after 1 week, 2 weeks, and 3 weeks, respectively; The neutralizing antibodies induced by the IN administration of SC2-DNA vaccine measured for viral infectivity inhibition using lenti-pseudoviral particles engineered to display SC2 S protein of different variants and expressing FLuc-ZsGreen reporter gene in HEK-293T cells engineered to express ACE2 receptor. Serum samples from of SC2-DNA vaccinated C57BL/6J mice at Week 18 (pooled serum from n=3 animals) were assayed for neutralizing activity in comparison with commercial SC2-spike antibody. The relative inhibition in infectivity was performed against lentiviral particles engineered with S protein SC2-Wuhan (FIG. 13E), SC2-SA-mutant (FIG. 13F) and SC2-D614G-mutant (FIG. 13G) variants. Each point represents the mean of serum collected from three mice with three technical replicates. The data are presented as mean±SEM; One-way ANOVA with Bonferroni post hoc test was used to draw significance of comparisons as indicated. Adjusted p-values were considered statistically significant if p-values <0.05 and the symbols indicating statistical significance were as follows—ns represents no-significant difference, * represents p<0.05,  represents p<0.01, * represents p<0.001 and **** represents p<0.0001 significance.

FIGS. 14A-14D show in vitro delivery of Fluc mRNA using AuNS-chitosan in (FIG. 14A) HEK293 and (FIG. 14B) A549 and cells imaged by optical bioluminescence (BLI). (FIG. 14C) In vivo BLI, and (FIG. 14D) ex vivo BLI of tissues after two doses of AuNS-chitosan-FLuc-mRNA delivery. There is significant expression of Firefly luciferase in the lungs and this is supported by the ex vivo tissue imaging findings.

Figure 15:
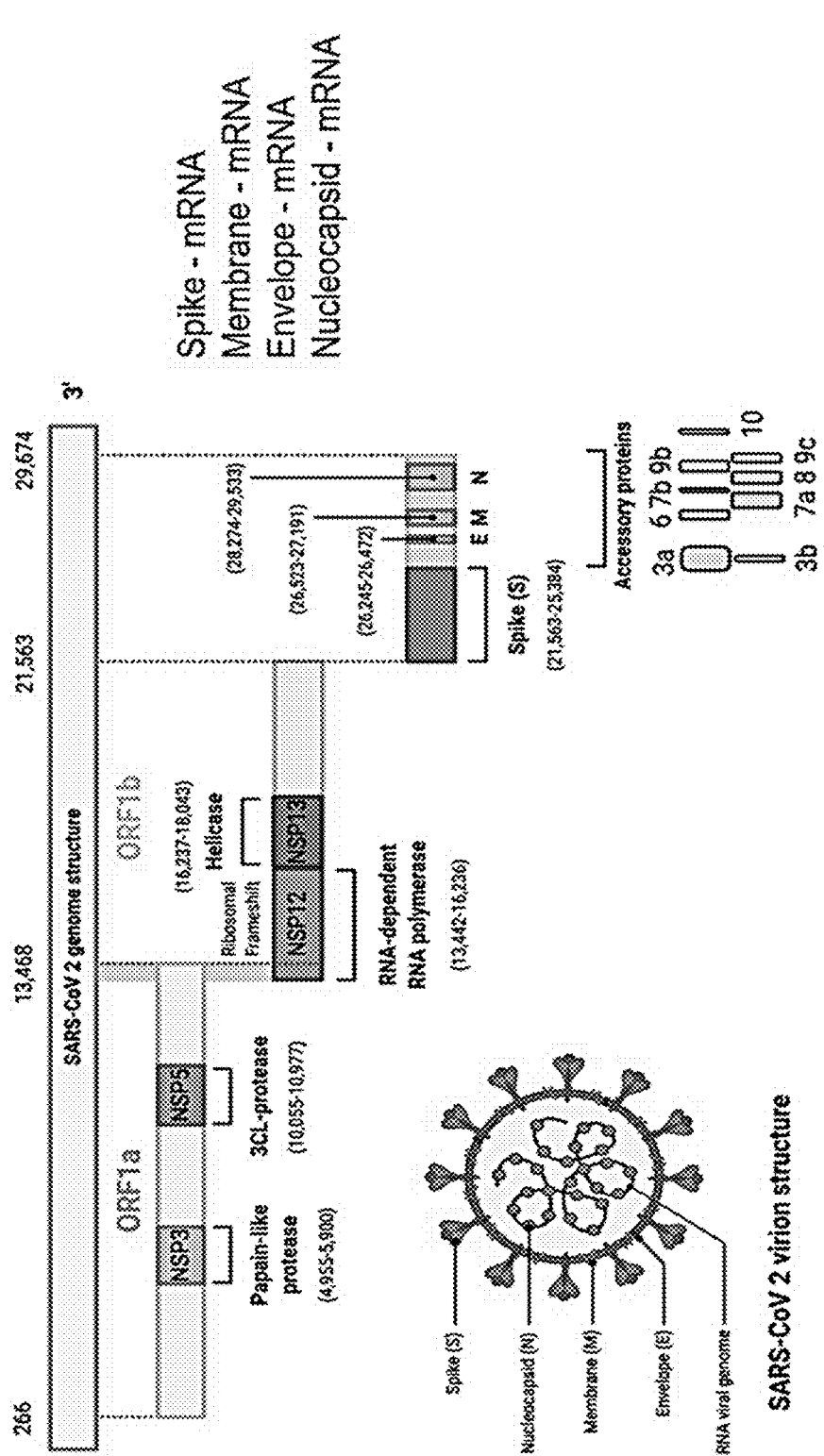

FIG. 15 illustrates the SARS-CoV-2 genome structure and locations where target proteins for a mRNA vaccine are encoded.

FIGS. 16A-16E shows recruitment of immune cells in the lung (FIG. 16A) and resident T cell distribution in the spleen (FIG. 16B), lungs (FIG. 16C), thymus (FIG. 16D), and lymph nodes (FIG. 16E) of mice IN treated with DNA vaccine expressing S protein of SC2. The DNA vaccine induced CD4+ T cells expressing memory and tissue-resident markers were used for assessment. The number of lung resident CD4+ T cells increased in the lungs of the immunized mice compared to control DNA treated mice. The lungs, spleen, thymus and lymph nodes were dissected 14 weeks after treatment to evaluate for T cell subtypes. (T cell subtypes: CD3/CD4, CD3/CD8; macrophages: CD45/CD11b; dendritic cells: CD45/CD11c; B cells: CD19 and CD22).

FIGS. 17A-17E illustrate flow cytometry analysis of IFNγ expression in CD45+ T cells isolated from spleen (FIG. 17A), lungs (FIG. 17B), thymus (FIG. 17C), lymph nodes (FIG. 17D), and blood (FIG. 17E) of BALB/c mice treated with pDNA and SC2-spike DNA.

Figure 18:
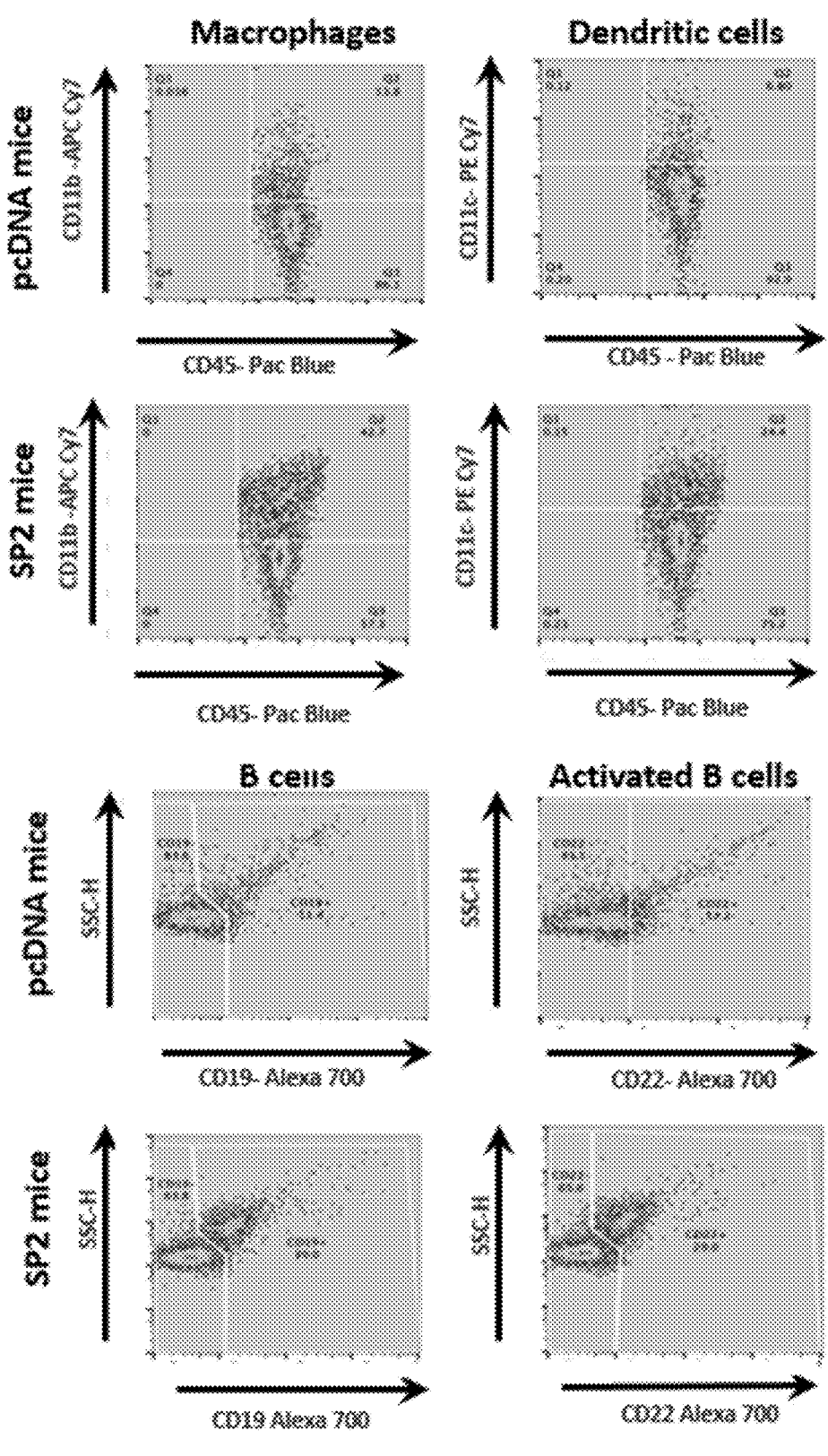

FIG. 18 shows that vaccination with DNA encoding SARS-CoV-2 S protein results in T and B cell activation in the Draining Lymph Node.

Figure 19A:
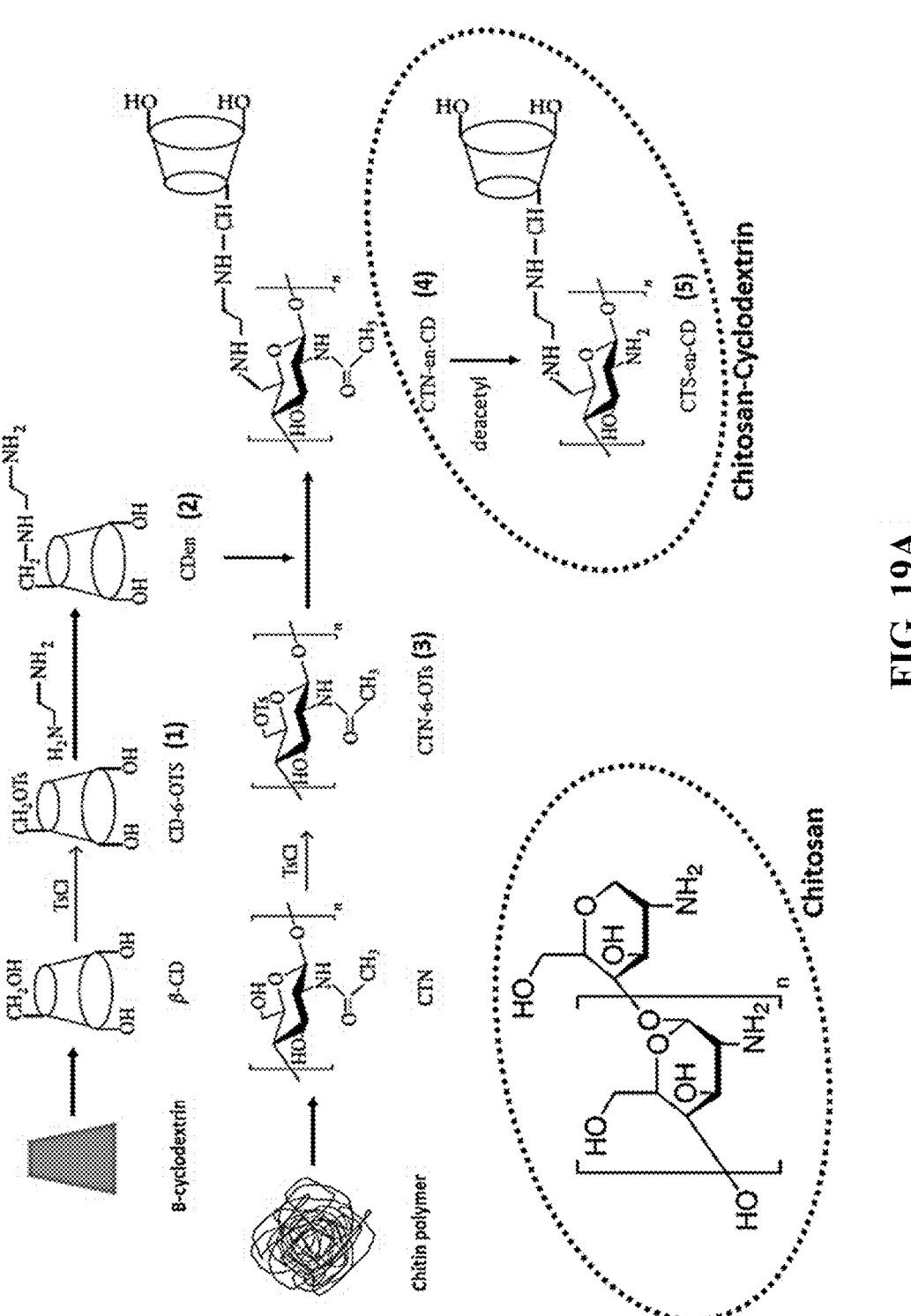
Figure 19B:
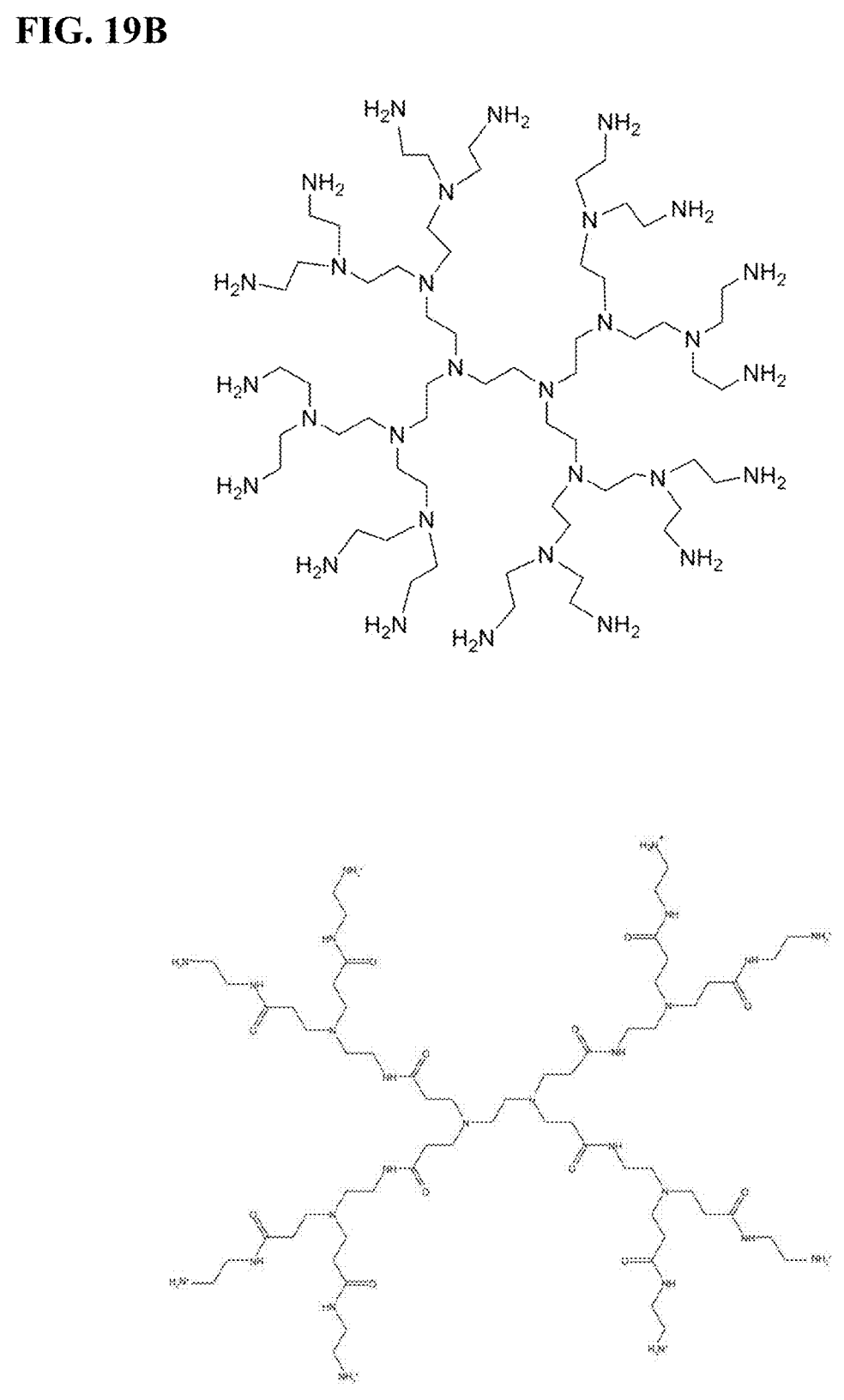

FIG. 19 shows the structures of polymers that form may form the outer layer of the nanoparticle. FIG. 19A shows the structures of chitosan and chitosan-cyclodextran and the reaction for synthesizing cyclodextrin conjugated chitosan (CD-CS). FIG. 19B shows the structure of Polyethylenimine (PEI) (top panel) and Polyamidoamine (PAMAM) (bottom panel) dendrimers.

DETAILED DESCRIPTION

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to nucleotides (e.g., deoxyribonucleotides or ribonucleotides) and polymers thereof in either single-, double- or multiple-stranded form, or complements thereof; or nucleosides (e.g., deoxyribonucleosides or ribonucleosides). In embodiments, "nucleic acid" does not include nucleosides. The terms "polynucleotide," "oligo-nucleotide," "oligo" or the like refer, in the usual and customary sense, to a linear sequence of nucleotides. The term "nucleoside" refers, in the usual and customary sense, to a glycosylamine including a nucleobase and a five-carbon sugar (ribose or deoxyribose). Non limiting examples, of nucleosides include, cytidine, uridine, adenosine, guanosine, thymidine and inosine. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include a reactive moiety that reacts with an outer layer of a nanoparticle through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGO-NUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanosine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. One skilled in the art will immediately recognize the identity and location of residues corresponding to a specific position in a protein (e.g., Spike protein) in other proteins with different numbering systems. For example, by performing a simple sequence alignment with a protein (e.g., Spike protein) the identity and location of residues corresponding to specific positions of the protein are identified in other protein sequences aligning to the protein. For example, a selected residue in a selected protein corresponds to glutamic acid at position 138 when the selected residue occupies the same essential spatial or other structural relationship as a glutamic acid at position 138. In some embodiments, where a selected protein is aligned for maximum homology with a protein, the position in the aligned selected protein aligning with glutamic acid 138 corresponds to glutamic acid 138. Instead of a primary sequence alignment, a three dimensional structural alignment can also be used, e.g., where the structure of the selected protein is aligned for maximum correspondence with the glutamic acid at position 138, and the overall structures compared. In this case, an amino acid that occupies the same essential position as glutamic acid 138 in the structural model corresponds to the glutamic acid 138 residue.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region, involved in binding the target antigen, and a constant ("C") region that interacts with other components of the immune system. The light and heavy chain variable regions (also referred to herein as light chain variable (VL) domain and heavy chain variable (VH) domain, respectively) come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs. The recognized immunoglobulin genes that encode antibodies include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The terms "antigen" and "epitope" interchangeably refer to the portion of a molecule (e.g., a polypeptide) which is specifically recognized by a component of the immune system, e.g., an antibody, a T cell receptor, or other immune receptor such as a receptor on natural killer (NK) cells. As used herein, the term "antigen" encompasses antigenic epitopes and antigenic fragments thereof.

An exemplary immunoglobulin (antibody) structural unit can have a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms "variable heavy chain," "$V_H$," or "VH" refer to the variable region of an immunoglobulin heavy chain, including an Fv, scFv, dsFv or Fab; while the terms "variable light chain," "$V_L$" or "VL" refer to the variable region of an immunoglobulin light chain, including an Fv, scFv, dsFv or Fab.

Examples of antibody functional fragments include, but are not limited to, complete antibody molecules, antibody fragments, such as Fv, single chain Fv (scFv), complementarity determining regions (CDRs), VL (light chain variable region), VH (heavy chain variable region), Fab, F(ab)2' and any combination of those or any other functional portion of an immunoglobulin peptide capable of binding to target antigen (see, e.g., FUNDAMENTAL IMMUNOLOGY (Paul ed., 4th ed. 2001). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., (1990) *Nature* 348:552). The term "antibody" also includes bivalent or bispecific molecules, diabodies, triabodies, and tetrabodies. Bivalent and bispecific molecules are described in, e.g., Kostelny et al. (1992) *J Immunol.* 148:1547, Pack and Pluckthun (1992) *Biochemistry* 31:1579, Hollinger et al. (1993), *PNAS. USA* 90:6444, Gruber et al. (1994) *J Immunol.* 152:5368, Zhu et al. (1997) *Protein Sci.* 6:781, Hu et al. (1996) *Cancer Res.*

56:3055, Adams et al. (1993) *Cancer Res.* 53:4026, and McCartney, et al. (1995) *Protein Eng.* 8:301.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

The term "Spike protein" or "S protein" as used herein includes any of the recombinant or naturally-occurring forms of Spike glycoprotein, also known as S glycoprotein, E2, peplomer protein, or variants or homologs thereof that maintain Spike protein activity (e.g. within at least 50%, 80%, 90%, 95%, 96%, 97%, 98%, 99% or 100% activity compared to Spike protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Spike protein. In embodiments, the Spike protein is substantially identical to the protein identified by the UniProt reference number PODTC2.

The term "Envelope protein" or "E protein" as used herein includes any of the recombinant or naturally-occurring forms of Envelope small membrane protein, also known as sM protein, or variants or homologs thereof that maintain Envelope protein activity (e.g. within at least 50%, 80%, 90%, 95%, 96%, 97%, 98%, 99% or 100% activity compared to Envelope protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Envelope protein. In embodiments, the Envelope protein is substantially identical to the protein identified by the UniProt reference number PODTC4.

The term "Membrane protein" or "M protein" as used herein includes any of the recombinant or naturally-occurring forms of Membrane protein, or variants or homologs thereof that maintain Membrane protein activity (e.g. within at least 50%, 80%, 90%, 95%, 96%, 97%, 98%, 99% or 100% activity compared to Membrane protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Membrane protein. In embodiments, the Membrane protein is substantially identical to the protein identified by the UniProt reference number P0DTC5.

The term "Nucleocapsid protein" or "N protein" as used herein includes any of the recombinant or naturally-occurring forms of Nucleocapsid protein, also known as Nucleoprotein protein, NC protein, or variants or homologs thereof that maintain Nucleocapsid protein activity (e.g. within at least 50%, 80%, 90%, 95%, 96%, 97%, 98%, 99% or 100% activity compared to Nucleocapsid protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Nucleocapsid protein. In embodiments, the Nucleocapsid protein is substantially identical to the protein identified by the UniProt reference number P0DTC9.

The term "Glycoprotein G protein" or "G protein" as used herein includes any of the recombinant or naturally-occurring forms of Major surface glycoprotein G protein, also known as Membrane-bound glycoprotein, mG protein, or variants or homologs thereof that maintain Glycoprotein G protein activity (e.g. within at least 50%, 80%, 90%, 95%, 96%, 97%, 98%, 99% or 100% activity compared to Glycoprotein G protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Glycoprotein G protein. In embodiments, the Glycoprotein G protein is substantially identical to the protein identified by the UniProt reference number P03423.

The term "Glycoprotein F protein" or "F protein" as used herein includes any of the recombinant or naturally-occurring forms of Fusion glycoprotein protein, also known as Fusion glycoprotein F0, Fusion glycoprotein F2, Intervening segment, Pep27, Peptide 27, Fusion glycoprotein F1, or variants or homologs thereof that maintain Glycoprotein F protein activity (e.g. within at least 50%, 80%, 90%, 95%, 96%, 97%, 98%, 99% or 100% activity compared to Glycoprotein F protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Glycoprotein F protein. In embodiments, the Glycoprotein F protein is substantially identical to the protein identified by the UniProt reference number P03420.

The term "Glycoprotein SH protein" or "SH protein" as used herein includes any of the recombinant or naturally-occurring forms of Small hydrophobic protein, also known as Small protein 1A, or variants or homologs thereof that maintain Glycoprotein SH protein activity (e.g. within at least 50%, 80%, 90%, 95%, 96%, 97%, 98%, 99% or 100% activity compared to Glycoprotein SH protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Glycoprotein SH protein. In embodiments, the Glycoprotein SH protein is substantially identical to the protein identified by the UniProt reference number P0DOE5.

The term "Hemagglutinin-neuraminidase protein" or "HN protein" as used herein includes any of the recombinant or naturally-occurring forms of Hemagglutinin-neuraminidase, or variants or homologs thereof that maintain Hemagglutinin-neuraminidase protein activity (e.g. within at least 50%, 80%, 90%, 95%, 96%, 97%, 98%, 99% or 100% activity compared to Hemagglutinin-neuraminidase protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Hemagglutinin-neuraminidase protein. In embodiments, the Hemagglutinin-neuraminidase protein is substantially identical to the protein identified by the UniProt reference number P21526.

The term "Fusion glycoprotein protein" or "F protein" as used herein includes any of the recombinant or naturally-occurring forms of Fusion glycoprotein 0, or variants or homologs thereof that maintain Fusion glycoprotein activity (e.g. within at least 50%, 80%, 90%, 95%, 96%, 97%, 98%, 99% or 100% activity compared to Fusion glycoprotein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Fusion glycoprotein. In embodiments, the Fusion glycoprotein is substantially identical to the protein identified by the UniProt reference number P06828.

The term "Matrix protein" or "M protein" as used herein includes any of the recombinant or naturally-occurring forms of Matrix protein, or variants or homologs thereof that maintain Matrix protein activity (e.g. within at least 50%, 80%, 90%, 95%, 96%, 97%, 98%, 99% or 100% activity compared to Matrix protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Matrix protein. In embodiments, the Matrix protein is substantially identical to the protein identified by the UniProt reference number P07873.

The term "Capsid glycoprotein VP1" or "VP1 protein" as used herein includes any of the recombinant or naturally-occurring forms of Capsid protein VP1, or variants or homologs thereof that maintain Capsid glycoprotein VP1 activity (e.g. within at least 50%, 80%, 90%, 95%, 96%, 97%, 98%, 99% or 100% activity compared to Capsid glycoprotein VP1). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Capsid glycoprotein VP1. In embodiments, the Capsid glycoprotein VP1 is substantially identical to the protein identified by the UniProt reference number U6BK95.

The term "Capsid glycoprotein VP0" or "VP0 protein" as used herein includes any of the recombinant or naturally-occurring forms of Capsid protein VP0, or variants or homologs thereof that maintain Capsid glycoprotein VP0 activity (e.g. within at least 50%, 80%, 90%, 95%, 96%, 97%, 98%, 99% or 100% activity compared to Capsid glycoprotein VP0). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Capsid glycoprotein VP0. In embodiments, the Capsid glycoprotein VP0 is substantially identical to the protein identified by the UniProt reference number D4NYJ3.

The term "hexon protein" or "hexon" as used herein includes any of the recombinant or naturally-occurring forms of hexon protein, or variants or homologs thereof that maintain hexon protein activity (e.g. within at least 50%, 80%, 90%, 95%, 96%, 97%, 98%, 99% or 100% activity compared to hexon protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring hexon protein. In embodiments, the hexon protein is substantially identical to the protein identified by the UniProt reference number Q9DKL1.

The term "penton protein" or "penton" as used herein includes any of the recombinant or naturally-occurring forms of penton protein, or variants or homologs thereof that maintain penton protein activity (e.g. within at least 50%, 80%, 90%, 95%, 96%, 97%, 98%, 99% or 100% activity compared to penton protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring penton protein. In embodiments, the penton protein is substantially identical to the protein identified by the UniProt reference number Q2YOH9.

The term "fiber protein" or "fiber" as used herein includes any of the recombinant or naturally-occurring forms of fiber protein, or variants or homologs thereof that maintain fiber protein activity (e.g. within at least 50%, 80%, 90%, 95%, 96%, 97%, 98%, 99% or 100% activity compared to fiber protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring fiber protein. In embodiments, the fiber protein is substantially identical to the protein identified by the UniProt reference number P04501.

The term "Pre-hexon-linking protein IIIa" as used herein includes any of the recombinant or naturally-occurring forms of Pre-hexon-linking protein IIIa, also known as Capsid vertex-specific component IIIa, CVSC, Protien IIIa, or pIIIa, or variants or homologs thereof that maintain Pre-hexon-linking protein IIIa activity (e.g. within at least 50%, 80%, 90%, 95%, 96%, 97%, 98%, 99% or 100% activity compared to Pre-hexon-linking protein IIIa). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Pre-hexon-linking protein IIIa. In embodiments, the Pre-hexon-linking protein IIIa is substantially identical to the protein identified by the UniProt reference number Q2Y0I0.

The term "Pre-hexon-linking protein VIII" as used herein includes any of the recombinant or naturally-occurring forms of Pre-hexon-linking protein VIII, also known as Pre-protein VIII, pVIII, or Protein VIII-N, or variants or homologs thereof that maintain Pre-hexon-linking protein VIII activity (e.g. within at least 50%, 80%, 90%, 95%, 96%, 97%, 98%, 99% or 100% activity compared to Pre-hexon-linking protein VIII). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Pre-hexon-linking protein VIII. In embodiments, the Pre-hexon-linking protein VIII is substantially identical to the protein identified by the UniProt reference number Q71BW3.

The term "Hexon-interlacing protein" as used herein includes any of the recombinant or naturally-occurring forms of Hexon-interlacing protein, also known as Protein IX, or variants or homologs thereof that maintain Hexon-interlacing protein activity (e.g. within at least 50%, 80%, 90%, 95%, 96%, 97%, 98%, 99% or 100% activity compared to Hexon-interlacing protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Hexon-interlacing protein. In embodiments, the Hexon-interlacing protein is substantially identical to the protein identified by the UniProt reference number Q71BW3.

The term "Major surface glycoprotein G" as used herein includes any of the recombinant or naturally-occurring forms of Major surface glycoprotein G, also known as Attachment glycoprotein G, Membrane-bound glycoprotein, mG, or variants or homologs thereof that maintain Major surface glycoprotein G activity (e.g. within at least 50%, 80%, 90%, 95%, 96%, 97%, 98%, 99% or 100% activity compared to Major surface glycoprotein G). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Major surface glycoprotein G. In embodiments, the Major surface glycoprotein G protein is substantially identical to the protein identified by the UniProt reference number Q6WB94.

The term "Fusion glycoprotein F0" as used herein includes any of the recombinant or naturally-occurring forms of Fusion glycoprotein F0, also known as Protein F, or variants or homologs thereof that maintain Fusion glycoprotein F0 activity (e.g. within at least 50%, 80%, 90%, 95%, 96%, 97%, 98%, 99% or 100% activity compared to Fusion glycoprotein F0). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Fusion glycoprotein F0. In embodiments, the Fusion glycoprotein F0 is substantially identical to the protein identified by the UniProt reference number Q6WB98.

The term "Nucleoprotein" or "Protein N" as used herein includes any of the recombinant or naturally-occurring forms of Nucleoprotein, also known as Nucleocapsid protein, or variants or homologs thereof that maintain Nucleoprotein activity (e.g. within at least 50%, 80%, 90%, 95%, 96%, 97%, 98%, 99% or 100% activity compared to Nucleoprotein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Nucleoprotein. In embodiments, the Nucleoprotein is substantially identical to the protein identified by the UniProt reference number Q6WBA1.

The term "Small hydrophobic protein" or "SH protein" as used herein includes any of the recombinant or naturally-occurring forms of Small hydrophobic protein, or variants or homologs thereof that maintain Small hydrophobic protein activity (e.g. within at least 50%, 80%, 90%, 95%, 96%, 97%, 98%, 99% or 100% activity compared to Small hydrophobic protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Small hydrophobic protein. In embodiments, the Small hydrophobic protein is substantially identical to the protein identified by the UniProt reference number Q6WB95.

The term "Matrix protein" or "M protein" as used herein includes any of the recombinant or naturally-occurring forms of Matrix protein, or variants or homologs thereof that maintain Matrix protein activity (e.g. within at least 50%, 80%, 90%, 95%, 96%, 97%, 98%, 99% or 100% activity compared to Matrix protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Matrix protein. In embodiments, the Matrix protein is substantially identical to the protein identified by the UniProt reference number Q6WB99.

The term "Capsid protein VP1" or as used herein includes any of the recombinant or naturally-occurring forms of Capsid protein VP1, or variants or homologs thereof that maintain Capsid protein VP1 activity (e.g. within at least 50%, 80%, 90%, 95%, 96%, 97%, 98%, 99% or 100% activity compared to Capsid protein VP1). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Capsid protein VP1. In embodiments, the Capsid protein VP1 is substantially identical to the protein identified by the UniProt reference number I0B934.

The term "Capsid protein VP2" or as used herein includes any of the recombinant or naturally-occurring forms of Capsid protein VP2, or variants or homologs thereof that maintain Capsid protein VP2 activity (e.g. within at least 50%, 80%, 90%, 95%, 96%, 97%, 98%, 99% or 100% activity compared to Capsid protein VP2). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Capsid protein VP2. In embodiments, the Capsid protein VP2 is substantially identical to the protein identified by the UniProt reference number Q27X19.

The terms "disease" or "condition" refer to a state of being or health status of a subject capable of being treated with a compound, pharmaceutical composition, or method provided herein. The disease can be an autoimmune, inflammatory, cancer, infectious, metabolic, developmental, cardiovascular, liver, intestinal, endocrine, neurological, or other disease. In some examples, the disease is an infectious disease (e.g. a coronavirus infection).

The term "infection" or "infectious disease" refers to a disease or condition that can be caused by organisms such as a bacterium, virus, fungi or any other pathogenic microbial agents. In embodiments, the infectious disease is caused by a pathogenic virus. Pathogenic viruses are viruses that can infect and replicate within cells (e.g. human cells) and cause diseases. In embodiments, the infectious disease is a virus associated disease. Non-limiting virus associated diseases include hepatic viral diseases (e.g., hepatitis A, B, C, D, E), herpes virus infection (e.g., HSV-1, HSV-2, herpes zoster), flavivirus infection, Zika virus infection, cytomegalovirus infection, a respiratory viral infection (causing a "pulmonary viral disease") (e.g., adenovirus infection, influenza, severe acute respiratory syndrome, coronavirus infection (e.g., SARS-CoV-1, SARS-CoV-2, MERS-CoV, COVID-19, MERS)), a gastrointestinal viral infection (e.g., norovirus infection, rotavirus infection, astrovirus infection), an exanthematous viral infection (e.g., measles, shingles, smallpox, rubella), viral hemorrhagic disease (e.g., Ebola, Lassa fever, dengue fever, yellow fever), a neurologic viral infection (e.g., West Nile viral infection, polio, viral meningitis, viral encephalitis, Japanese enchephalitis, rabies), and human papilloma viral infection. In embodiments, the virus associated disease is caused by a pulmonary virus.

The term "pulmonary viral infection" or "pulmonary viral disease" refers to a condition caused by a virus that can infect and replicate within cells and cause diseases or symptoms that affect the respiratory system (e.g. lower respiratory system, upper respiratory system, and lungs). In embodiments, the virus that causes a pulmonary viral infection may enter the subject by using the nose and/or mouth as ports of entry. The pulmonary viral infection may be caused by viruses including, but not limited to, Human respiratory syncytial virus (HRSV), Human parainfluenza virus (HPV), Human rhinovirus (HRV), Adenovirus (ADV), Human coronavirus (HCoV), Coronavirus associated with SARS (SARS-CoV), Human metapneumovirus (HMPV), or Human bocavirus (HBoV). Pulmonary viral infections may result in one or more symptoms as listed in Table 2.

The terms "virus" or "virus particle" are used according to their plain ordinary meaning in the biological arts and refer to a particle including a viral genome (e.g. DNA, RNA, single strand, double strand), a protective coat of proteins (e.g. capsid) and associated proteins, and in the case of enveloped viruses (e.g. herpesvirus), an envelope including lipids and optionally components of host cell membranes, and/or viral proteins.

"Human coronavirus" or "HCoV" refers to a group of RNA viruses that can enter and replicate in the cells of human and may cause disease (e.g. respiratory tract infections). In embodiments, coronaviruses are enveloped viruses with positive-sense single-stranded RNA and a nucleocapsid. Coronaviruses range in size and can be from, for example, 50 to 200 nm in diameter. In embodiments, the coronavirus viral envelope is made up of a lipid bilayer and includes the membrane, envelope and spike proteins. In instances, HcoV enters the host cell when the spike protein attaches to a host cell receptor. HCoV include Human coronavirus OC43 (HCoV-OC43), Human coronavirus HKU1 (HCoV-HKU1), Human coronavirus 229E (HCoV-229E), Human coronavirus NL63 (HCoV-NL63), Severe acute respiratory syndrome coronavirus (SARS-CoV), Middle East respiratory syndrome-related coronavirus (MERS-CoV), and Severe acute respiratory syndrome coronavirus 2 (SARS-CoV-2). In instances, entry of HcoV into a cell may cause SARS, MERS, or COVID-19.

The term "severe acute respiratory syndrome coronavirus 2" or "SARS-CoV-2" refers to the strain of coronavirus that causes coronavirus disease 2019 (COVID-19). In embodiments, SARS-CoV-2 is a positive-sense single-stranded RNA virus. SARS-CoV-2 belongs to the family of betacoronaviruses, whose members include two other zoonotic viruses that have caused severe disease outbreaks in the new millennium: severe acute respiratory syndrome coronavirus (SARS-CoV) and Middle East respiratory syndrome coronavirus (MERS-CoV). SARS-CoV-2 shows nearly 80 percent genetic similarity to SARS-CoV, which triggered the severe acute respiratory syndrome (SARS) epidemic in 2002-2003. SARS-CoV-2 is more distantly related to MERS-CoV, which is responsible for the Middle East respiratory syndrome (MERS) epidemic that began in 2012 and still persists. See, e.g., Yuki et al., 2020, Clin. Immun. 215, 108427; Chen et al. 2020, *J. Med. Virol.* 92, 418-423. The term "SARS-CoV" refers to SARS coronavirus. The term "SARS-CoV" includes any coronovirus, such as SARS-CoV-2, SARS-CoV-1, and MERS-CoV.

"COVID-19" refers to the disease caused by SARS-CoV-2. COVID-19 has an incubation period of 2-14 days, and symptoms include, e.g., fever, tiredness, cough, and shortness of breath (e.g., difficulty breathing).

The term "severe acute respiratory syndrome coronavirus" or "SARS-CoV-1" refers to the strain of coronavirus that causes severe acute respiratory syndrome (SARS). In embodiments, SARS-CoV-1 is an enveloped, positive-sense, single-stranded RNA virus that infects the epithelial cells within the lungs. In embodiments, the virus enters the host cell by binding to the angiotensin-converting enzyme 2 (ACE2) receptor.

"MERS-CoV" refers to Middle Eastern respiratory syndrome-associated coronavirus. See, e.g., Chung et al, Genetic Characterization of Middle East Respiratory Syndrome Coronavirus, South Korea, 2018. Emerging Infectious Diseases, 25(5):958-962 (2019).

"Middle Eastern respiratory syndrome" or "MERS" refers to the disease caused by MERS-coronavirus.

"Human respiratory syncytial virus" or "RSV", also known as human orthopneumovirus refers to a virus that can infect human cells and may cause infections with symptoms affecting the respiratory tract. In embodiments, RSV is a negative-sense single-stranded RNA virus. RSV can be transmitted through the nose or eys, and in instances can effect the columnar epithelial cells of the upper and lower airway. F protein on the surface of RSV may be used to fuse viral and host cell membranes, thus resulting infection of the host cell. In instances, F and G glycoproteins are used for viral attachment and infection of the host cell. Symptoms and syndromes that may be caused by RSV infection include pneumonia, respiratory failure, apnea, respiratory distress, and distant inflammation.

"Human parainfluenza virus" or "HPIV" refers to a virus that infect cells and may cause human parainfluenza. In embodiments, HPIVs are single-stranded RNA viruses. HPIVs include Human parainfluenza virus type 1, Human parainfluenza virus type 2, Human parainfluenza virus type 3, and Human parainfluenza virus type 4. In instances, HPIV infects the host cell by attachment and fusion between the virus and host cell lipid membrane. For example, HPIV may enter the cell by way of using the Envelope protein and Fusion protein to attach and fuse to the host cell for cell entry. Symptoms and syndromes caused by HPIV infection include lower respiratory tract infections, upper respiratory tract infections, bronchiolitis, pneumonia, neurologic disease, and airway inflammation.

"Human rhinovirus" or "HRV" refers to a virus that infect humans and may cause the common cold. HRV include rhinovirus A, rhinovirus B and rhinovirus C. In embodiments, HRV is a single-stranded postivive sense RNA virus. In embodiments, HRV is transmitted by aerosols of respiratory droplets or fomites. Syndromes and symptoms caused by HRV infection include the common cold, sore throat, runny nose, nasal congestion, sneezing, cough, muscle aches, fatigue and headache.

"Adenovirus" or "ADV" refers to a virus that can infect cells and may cause a wide range of respiratory symptoms. In embodiments, ADV is a nonenveloped virus with a double-stranded DNA genome. In embodiments, human ADV (HAdV) include adenovirus A, adenovirus B, adenovirus C, adenovirus D, adenovirus E, adenovirus F and adenovirus G. In instances, ADV cell entry is initiated by binding of the knob domain of the fiber protein to the host cell receptor. In instances, the penton protein interacts with an integrine molecule thereby stimulating entry of the adenovirus. Symptoms and syndromes caused by adenovirus infection include tonsillitis, bronchiolitis and pneumonia.

As defined herein, the term "inhibition", "inhibit", "inhibiting" and the like in reference to an activity and/or functionality of a molecule (e.g. polynucleotide or protein) means negatively affecting (e.g., decreasing or reducing) the activity or function of the molecule relative to the activity or function of the protein in the absence of the inhibition. Thus, inhibition includes, at least in part, partially or totally blocking stimulation, decreasing, preventing, or delaying activation, or inactivating, desensitizing, or down-regulating signal transduction or enzymatic activity or the amount of a protein or polynucleotide. Similarly an "inhibitor" is a compound that inhibits a target bio-molecule (i.e. nucleic acid, peptide, carbohydrate, lipid or any other molecules that can be found from nature), e.g., by binding, partially or totally blocking, decreasing, preventing, delaying, inactivating, desensitizing, or down-regulating activity of the target bio-molecule. In the context of disease prevention treatment, inhibition refers to reduction of a disease or symptoms of disease (e.g. Covid-19).

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is not prophylactic treatment.

The term "prevent" refers to a decrease in the occurrence of a disease or disease symptoms in a patient. As indicated above, the prevention may be complete (no detectable symptoms) or partial, such that fewer symptoms are observed than would likely occur absent treatment.

As used herein, a "symptom" of a disease includes any clinical or laboratory manifestation associated with the disease, and is not limited to what a subject can feel or observe.

The term "associated" or "associated with" in the context of a substance or substance activity or function associated with a disease means that the disease can be caused by (in whole or in part), or a symptom of the disease can be caused by (in whole or in part) the substance or substance activity or function. When the term is used in the context of a symptom, e.g. a symptom being associated with a disease or condition, it means that a symptom can be indicative of the disease or condition present in the subject who shows the symptom.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, Dosage Calculations (1999); and *Remington: The Science and Practice of Pharmacy,* 20th Edition, 2003, Gennaro, Ed., Lippincott, Williams & Wilkins).

For any compound described herein, the therapeutically effective amount can be initially determined from binding assays or cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as an aerosol, dry powder, nasal spray, suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g., to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols. The preparations may also be combined with inhaled mucolytics (e.g., rhDNase, as known in the art) or with inhaled bronchodilators (short or long acting beta agonists, short or long acting anticholinergics), inhaled corticosteroids, or inhaled antibiotics to improve the efficacy of these drugs by providing additive or synergistic effects. The compositions of the present invention can be delivered transdermally, by a topical route, formulated as applicator sticks, solutions, suspensions, emulsions, gels, creams, ointments, nanoparticles, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., *Gao Pharm. Res.* 12:857-863, 1995); or, as microspheres for oral administration (see, e.g., Eyles, *J Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The term "vaccine" refers to a composition that can provide active acquired immunity to and/or therapeutic effect (e.g. treatment) of a particular disease or a pathogen. A vaccine typically contains one or more agents that can induce an immune response in a subject against a pathogen or disease, i.e. a target pathogen or disease. The immunogenic agent stimulates the body's immune system to recognize the agent as a threat or indication of the presence of the target pathogen or disease, thereby inducing immunological memory so that the immune system can more easily recognize and destroy any of the pathogen on subsequent exposure. Vaccines can be prophylactic (e.g. preventing or ameliorating the effects of a future infection by any natural or pathogen, or of an anticipated occurrence of cancer in a predisposed subject) or therapeutic (e.g., treating cancer in a subject who has been diagnosed with the cancer). The administration of vaccines is referred to vaccination. In some examples, a vaccine composition can provide nucleic acid, e.g. mRNA that encodes antigenic molecules (e.g. peptides) to a subject. The nucleic acid that is delivered via the vaccine composition in the subject can be expressed into antigenic molecules and allow the subject to acquire immunity against the antigenic molecules. In the context of the vaccination against infection disease, the vaccine composition can provide mRNA encoding antigenic molecules that are associated with a certain pathogen, e.g. one or more peptides that are known to be expressed in the pathogen (e.g. pathogenic bacterium or virus). In the context of a viral vaccine, the vaccine composition can provide mRNA encoding certain viral peptides that are characteristic for the virus that immunity is sought for, e.g. peptides that are substantially exclusively or highly expressed on the viral surface (e.g., capsid). The subject, after vaccination with the viral vaccine composition, can have immunity against the viral peptide t kill the cells expressing it with specificity.

The term "adjuvant" is used in accordance with its plain ordinary meaning within Immunology and refers to a substance that is commonly used as a component of a vaccine. Adjuvants may increase an antigen specific immune response in a subject when administered to the subject with one or more specific antigens as part of a vaccine. In embodiments, an adjuvant accelerates an immune response to an antigen. In embodiments, an adjuvant prolongs an immune response to an antigen. In embodiments, an adjuvant enhances an immune response to an antigen.

The term "immune response" used herein encompasses, but is not limited to, an "adaptive immune response", also known as an "acquired immune response" in which adaptive immunity elicits immunological memory after an initial response to a specific pathogen or a specific type of cells that is targeted by the immune response, and leads to an enhanced response to that target on subsequent encounters. The induction of immunological memory can provide the basis of vaccination.

The term "immunogenic" or "antigenic" refers to a compound or composition that induces an immune response, e.g., cytotoxic T lymphocyte (CTL) response, a B cell response (for example, production of antibodies that specifically bind the epitope), an NK cell response or any combinations thereof, when administered to an immunocompetent subject. Thus, an immunogenic or antigenic composition is a composition capable of eliciting an immune response in an immunocompetent subject. For example, an immunogenic or antigenic composition can include one or more immunogenic epitopes associated with a pathogen or a specific type of cells that is targeted by the immune response. In addition, an immunogenic composition can include isolated nucleic acid constructs (such as DNA or RNA) that encode one or more immunogenic epitopes of the antigenic polypeptide that can be used to express the epitope(s) (and thus be used to elicit an immune response against this polypeptide or a related polypeptide associated with the targeted pathogen or type of cells).

According to the methods provided herein, the subject can be administered an effective amount of one or more of agents, compositions or complexes, all of which are interchangeably used herein, (e.g. complex or vaccine composition including the same) provided herein. The terms "effective amount" and "effective dosage" are used interchangeably. The term "effective amount" is defined as any amount necessary to produce a desired effect (e.g., expressing an immunogentic peptide expressed by a nucleic acid and exhibiting intended outcome of the immunogenic peptide). Effective amounts and schedules for administering the agent can be determined empirically by one skilled in the art. The dosage ranges for administration are those large enough to produce the desired effects, e.g. transfection of nucleic acid, modulation in gene expression, gene-edition, induction of stem cells, induction of immune response and more. The dosage should not be so large as to cause substantial adverse side effects, such as unwanted cross-reactions, anaphylactic reactions, and the like. Generally, the dosage can vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products. For example, for the given parameter, an effective amount can show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact dose and formulation can depend on the purpose of the treatment, and can be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)).

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The terms "bind" and "bound" as used herein is used in accordance with its plain and ordinary meaning and refers to the association between atoms or molecules. The association can be covalent (e.g., by a covalent bond or linker) or non-covalent (e.g., electrostatic interactions (e.g., ionic bond, hydrogen bond, or halogen bond), van der Waals interactions (e.g., dipole-dipole, dipole-induced dipole, or London dispersion), ring stacking (pi effects), hydrophobic interactions, and the like).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As used herein, the term "conjugated" when referring to two moieties means the two moieties (e.g. nanoparticle outer layer and nucleic acid) are bonded, wherein the bond or bonds connecting the two moieties may be covalent or non-covalent. In embodiments, the two moieties are covalently bonded to each other (e.g., directly or through a covalently bonded intermediary). In embodiments, the two moieties are non-covalently bonded (e.g., through ionic bond(s), van der Waals bond(s)/interactions, hydrogen bond(s), polar bond(s), or combinations or mixtures thereof).

As used herein, the terms "bioconjugate" and "bioconjugate linker" refers to the resulting association between atoms or molecules of "bioconjugate reactive groups" or "bioconjugate reactive moieties". The association can be direct or indirect. For example, a conjugate between a first bioconjugate reactive group (e.g., —NH2, —C(O)OH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine).

Useful bioconjugate reactive moieties used for bioconjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido or maleimide groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold, or react with maleimides;

(h) amine or sulfhydryl groups (e.g., present in cysteine), which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding; and (m) metal bonding to reactive phosphorus groups (e.g. phosphines) to form, for example, phosphate diester bonds.

(n) azides coupled to alkynes using copper catalyzed cycloaddition click chemistry.

(o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

A "detectable agent" or "detectable moiety" is a composition, substance, element, or compound; or moiety thereof; detectable by appropriate means such as spectroscopic, photochemical, biochemical, immunochemical, chemical, magnetic resonance imaging, or other physical means. For example, useful detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$S, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{21}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

As used herein the terms "oligomer" and "polymer" refer to a compound that has a plurality of repeating subunits, (e.g., polymerized monomers). The terms "co-oligomer" or "co-polymer" refers to an oligomer or polymer that includes 2 or more different residues (monomer units or monomers, which are interchangeably used herein). The number of monomers in oligomers is generally less than the number of monomers in polymers. Therefore, in some examples, oligomers can have 1 to about 10 monomers, 1 to about 20 monomers, 1 to about 30 monomers, 1 to about 40 monomers, 1 to about 50 monomers, 1 to about 100 monomers, 1 to about 150 monomers, 1 to about 200 monomers, 1 to about 250 monomers, 1 to about 300 monomers, 1 to about 350 monomers, 1 to about 400 monomers, 1 to about 450 monomers or 1 to about 500 monomers is in length. In some examples, oligomers can have less than about 500 monomers, less than about 450 monomers, less than about 400 monomers, less than about 350 monomers, less than about 300 monomers, less than about 250 monomers, less than about 200 monomers, less than about 150 monomers, less than about 100 monomers, less than about 50 monomers, less than about 40 monomers, less than about 30 monomers, less than about 20 monomers or less than about 10 monomers in length. In the context of polymers, the number of monomers in polymers is generally more than the number of monomers in oligomers. Therefore, in some examples, polymers can have about 500 to about 1000 monomers, about 500 to about 2000 monomers, about 500 to about 3000 monomers, about 500 to about 4000 monomers, about 500 to about 5000 monomers, about 500 to about 6000 monomers, about 500 to about 7000 monomers, about 500 to about 8000 monomers, about 500 to about 9000 monomers, about 500 to about 10000 monomers, or more than 10000 monomers in length. In embodiments, the polymer is a biopolymer. As used herein, "biopolymer" refers to a polymer produced in the cells of living organisms. In embodiments, the polymer is a polysaccharide. In embodiments, the polymer is a cationic polysaccharide. In embodiments, the polysaccharide is a repeating unit of organic monomers (e.g. monosaccharide) or a repeating unit of a plurality of different organic monomers. In embodiments, a polysaccharide is a repeating unit of monosaccharides (e.g. glucosamine, glucose, methylglucoside, etc.) or a repeating unit of a plurality of different monosaccharides. In embodiments, the polysaccharide is a glycan.

The term "polymerizable monomer" is used in accordance with its meaning in the art of polymer chemistry and refers to a compound that may covalently bind chemically to other monomer molecules (such as other polymerizable monomers that are the same or different) to form a polymer.

The term "block copolymer" is used in accordance with its ordinary meaning and refers to two or more portions (e.g., blocks) of polymerized monomers linked by a covalent bond. In embodiments, a block copolymer is a repeating pattern of polymers. In embodiments, the block copolymer includes two or more monomers in a periodic (e.g., repeating pattern) sequence. For example, a diblock copolymer has the formula: -B-B-B-B-B-B-A-A-A-A-A-, where 'B' is a first subunit and 'A' is a second subunit covalently bound together. A triblock copolymer therefore is a copolymer with three distinct blocks, two of which may be the same (e.g., -A-A-A-A-A-B-B-B-B-B-B-A-A-A-A-A-) or all three are different (e.g., -A-A-A-A-A-B-B-B-B-B-B-C-C-C-C-C-) where 'A' is a first subunit, 'B' is a second subunit, and 'C' is a third subunit, covalently bound together.

The phrase "average molecular weight" refers to the weight average molecular weight of a polymer as determined by gel permeation chromatography (also known as GPC or size exclusion chromatography (SEC)) using tetrahydrofuran (THF) as the solvent and using a molecular weight calibration curve using polystyrene standards.

A "nanoparticle," as used herein, is a particle wherein the longest diameter is less than or equal to 1000 nanometers. The longest dimension of the nanoparticle may be referred to herein as the length of the nanoparticle. The shortest dimension of the nanoparticle may be referred to herein refer as the width of the nanoparticle. Nanoparticles may be composed of any appropriate material. For example, nanoparticle cores may include appropriate metals and metal oxides thereof (e.g., a metal nanoparticle core), carbon (e.g., an organic nanoparticle core), silicon and oxides thereof (e.g., a silicon nanoparticle core) or boron and oxides thereof (e.g., a boron nanoparticle core), or mixtures thereof. In embodiments, the nanoparticle has the shape of a sphere, rod, star, cube, triangular, hexagonal, cylinder, spherocylinder, or ellipsoid. A nanoparticle may further include an outer layer that covers most (e.g. at least 70%, 75%, 80%, 85%, 90%, 95%, 98%, or 99%) or all of the nanoparticle core. The outer layer of the nanoparticle may include moieties that attach to one or more biomolecules (e.g. pulmonary viral protein, nucleic acid encoding said pulmonary viral protein)

An "inorganic nanoparticle" refers to a nanoparticle without carbon. For example, an inorganic nanoparticle may refer to a metal or metal oxide thereof (e.g., gold nanoparticle, iron nanoparticle), silicon and oxides thereof (e.g., a silica nanoparticle), or titanium and oxides thereof (e.g., titanium dioxide nanoparticle). In embodiments, the inorganic nanoparticle is a gold nanoparticle. The inorganic nanoparticle may be a metal nanoparticle. When the nanoparticle is a metal, the metal may be titanium, zirconium, gold, silver, platinum, cerium, arsenic, iron, aluminum or silicon. The metal nanoparticle may be titanium, zirconium, gold, silver, or platinum and appropriate metal oxides thereof. In embodiments, the nanoparticle is titanium oxide, zirconium oxide, cerium oxide, arsenic oxide, iron oxide, aluminum oxide, or silicon oxide. The metal oxide nanoparticle may be titanium oxide or zirconium oxide. The nanoparticle may be titanium. The nanoparticle may be gold. In embodiments, the metal nanoparticle is a gold nanoparticle. In embodiments, the inorganic nanoparticle may further include a moiety which contains carbon.

The term "adjuvant" is used in accordance with its plain ordinary meaning within Immunology and refers to a substance that is commonly used as a component of a vaccine. Adjuvants may increase an antigen specific immune response in a subject when administered to the subject with one or more specific antigens as part of a vaccine. In embodiments, an adjuvant accelerates an immune response to an antigen. In embodiments, an adjuvant prolongs an immune response to an antigen. In embodiments, an adjuvant enhances an immune response to an antigen.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

A "synergistic amount" as used herein refers to the sum of a first amount (e.g., an amount of a compound provided herein) and a second amount (e.g., a therapeutic agent) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of the compound administered in combination where the measured effect is greater than the sum of the individual effects of each of the compounds provided herein administered alone as a single agent.

In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the compound provided herein when used separately from the therapeutic agent. In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the therapeutic agent when used separately from the compound provided herein.

Complexes

Provided herein, inter alia, are complexes including nanoparticles attached to one or more pulmonary viral proteins or one or more nucleic acids encoding the pulmonary viral proteins. As used herein, the term "pulmonary virus" refers to a virus that can enter and replicate within cells (e.g. human cells) and cause infections or infectious diseases that affect the lungs and/or the respiratory tract. For example, a pulmonary virus infection may cause symptoms including, but not limited to, shortness of breath (dyspnea), difficulty breathing, fatigue, cough, and chest pain. Clinical syndromes caused by pulmonary viruses may include the common cold, acute and chronic bronchitis, bronchiolitis, croup, pneumonia, asthma, bronchiectasis, pneumonia, pulmonary embolism, pulmonary hypertension, sarcoidosis, sleep apnea, and distant inflammatory effects. In embodiments, a pulmonary virus causes one or more syndromes as listed in Table 2. Thus, "pulmonary viral protein" refers to a protein (e.g. spike protein, etc.) that is encoded within the genome of a pulmonary virus (e.g. human coronaviruses, adenoviruses, etc.).

The complex provided herein including embodiments thereof includes a nanoparticle, wherein the nanoparticle includes a gold core. The gold core is amenable to attaching (e.g. by indirect or direct attachment) a viral protein or a nucleic acid encoding the viral protein to the nanoparticle. In instances, the viral protein or nucleic acid may be indirectly attached to the nanoparticle gold core, for example, though a covalent linker (e.g. a peptide linker, a chemical linker, a bioconjugate linker etc.) or through attachment with the nanoparticle outer layer. Thus, in an aspect is provided a complex including: (a) a nanoparticle including a gold core; and (b) a pulmonary viral protein or fragment thereof, or a nucleic acid encoding the pulmonary viral protein or fragment thereof, wherein the pulmonary viral protein or nucleic acid is attached to the nanoparticle. In embodiments, the complex includes at least one pulmonary viral protein or fragment thereof and at least one nucleic acid encoding a pulmonary viral protein or fragment thereof.

In embodiments, the complex includes a plurality of pulmonary viral proteins or fragments thereof. In embodiments, the plurality of pulmonary viral proteins include different pulmonary viral proteins. In embodiments, the complex includes a plurality of nucleic acids encoding the pulmonary viral protein or fragment thereof. In embodiments, the plurality of nucleic acids encode different pulmonary viral proteins or fragments thereof. In embodiments, the complex includes a plurality of pulmonary viral proteins or fragments thereof and a plurality of nucleic acids encoding pulmonary viral proteins or fragments thereof.

In embodiments, the pulmonary viral protein is a protein from human respiratory syncytial virus (HRSV), human parainfluenza virus (HPV), human rhinovirus (HRV), adenovirus (ADV), human coronavirus (HCoV), coronavirus associated with SARS (SARS-CoV), human metapneumovirus (HMPV), or human bocavirus (HBoV). In embodiments, the pulmonary viral protein is a protein from human respiratory syncytial virus (HRSV). In embodiments, the pulmonary viral protein is a protein from human parainfluenza virus (HPV). In embodiments, the pulmonary viral protein is a protein from human rhinovirus (HRV). In embodiments, the pulmonary viral protein is a protein from adenovirus (ADV). In embodiments, the pulmonary viral protein is a protein from human coronavirus (HCoV). In embodiments, the pulmonary viral protein is a protein from coronavirus associated with SARS (SARS-CoV). In embodiments, the pulmonary viral protein is a protein from human metapneumovirus (HMPV). In embodiments, the pulmonary viral protein is a protein from human bocavirus (HBoV).

In embodiments, the pulmonary viral protein from HRSV is Glycoprotein G (receptor binding), Glycoprotein F (membrane fusion), or Glycoprotein SH. In embodiments, the pulmonary viral protein from HRSV is Glycoprotein G. In embodiments, the pulmonary viral protein from HRSV is Glycoprotein F. In embodiments, the pulmonary viral protein from HRSV is Glycoprotein SH. In embodiments, the pulmonary viral protein from HPV is HN-Tetramer, F-Protein trimer, or Matrix protein (M). In embodiments, the pulmonary viral protein from HPV is HN-Tetramer. In embodiments, the pulmonary viral protein from HPV is F-Protein trimer. In embodiments, the pulmonary viral protein from HPV is Matrix protein (M). In embodiments, the pulmonary viral protein from HRV is Viral capsid glycoprotein VPT, Viral capsid glycoprotein VP2, Viral capsid glycoprotein VP3, or Viral capsid glycoprotein VP4. In embodiments, the pulmonary viral protein from HRV is Viral capsid glycoprotein VP1. In embodiments, the pulmonary viral protein from HRV is Viral capsid glycoprotein VP2. In embodiments, the pulmonary viral protein from HRV is Viral capsid glycoprotein VP3. In embodiments, the pulmonary viral protein from HRV is Viral capsid glycoprotein VP4. In embodiments, the pulmonary viral protein from ADV is Hexon, Penton, Fiber, IIIa, VIII, or IX. In embodiments, the pulmonary viral protein from ADV is Hexon. In embodiments, the pulmonary viral protein from ADV is Penton. In embodiments, the pulmonary viral protein from ADV is Fiber. In embodiments, the pulmonary viral protein from ADV is IIIa. In embodiments, the pulmonary viral protein from ADV is VIII. In embodiments, the pulmonary viral protein from ADV is IX. In embodiments, the pulmonary viral protein from HCoV is Envelop, Membrane, Spike Protein, or Nucleocapsid protein. In embodiments, the pulmonary viral protein from HCoV is Envelop protein. In embodiments, the pulmonary viral protein from HCoV is Membrane protein. In embodiments, the pulmonary viral protein from HCoV is Spike Protein. In embodiments, the pulmonary viral protein from HCoV is Nucleocapsid protein. In embodiments, the pulmonary viral protein from SARS-CoV is Envelop, Membrane, Spike Protein, or Nucleocapsid protein. In embodiments, the pulmonary viral protein from SARS-CoV is Envelop protein. In embodiments, the pulmonary viral protein from SARS-CoV is Membrane protein. In embodiments, the pulmonary viral protein from SARS-CoV is Spike Protein. In embodiments, the pulmonary viral protein from SARS-CoV is Nucleocapsid protein. In embodiments, the pulmonary viral protein from HMPV is Glycoprotein-G, Fusion protein-F, Nucleoprotein-N, SH-Protein, or Matrix protein. In embodiments, the pulmonary viral protein from HMPV is Glycoprotein-G. In embodiments, the pulmonary viral protein from HMPV is Fusion protein-F. In embodiments, the pulmonary viral protein from HMPV is Nucleoprotein-N. In embodiments, the pulmonary viral protein from HMPV is SH-Protein. In embodiments, the pulmonary viral protein from HMPV is Matrix protein. In embodiments, the pulmonary viral protein from HBoV is Viral capsid protein 1 (VP2) or and Viral capsid protein 2 (VP2). In embodiments, the pulmonary viral protein from HBoV is Viral capsid protein 1 (VP2). In embodiments, the pulmonary viral protein from HBoV is Viral capsid protein 2 (VP2).

In embodiments, the pulmonary virus is SARS-CoV-2. In embodiments, the pulmonary viral protein or fragment thereof is S protein, N protein, M protein, or E protein. In embodiments, the pulmonary viral protein or fragment thereof is S protein. In embodiments, the pulmonary viral protein or fragment thereof is N protein. In embodiments, the pulmonary viral protein or fragment thereof is M protein. In embodiments, the pulmonary viral protein or fragment thereof is E protein. Thus, in embodiments, the nucleic acid encodes S protein, N protein, M protein, or E protein. In embodiments, the nucleic acid encodes S protein. In embodiments, the nucleic acid encodes N protein. In embodiments, the nucleic acid encodes M protein. In embodiments, the nucleic acid encodes E protein.

For the complex provided herein, in embodiments, the gold core is a gold-iron oxide core. In instances, the iron-oxide component may be used for imaging or diagnosing methods (e.g. MRI).

For the complex provided herein, in embodiments, the nanoparticle is modified by attaching an outer layer to the gold core. Thus, in embodiments, the nanoparticle includes an outer layer. The outer layer of the nanoparticle may include a compound (e.g. polymer, cationic polysaccharide) with a functional group by which a viral protein or a nucleic acid encoding the viral protein may be attached (e.g. by way of electrostatic interactions (e.g. ionic bond, hydrogen bond, halogen bond) or hydrophobic interactions, by covalent conjugation chemistry) to the nanoparticle. For covalent attachment of a viral protein or nucleic acid to the outer layer, covalent conjugation methods may be used which are are well known in the art and described herein.

In embodiments, the outer layer of the nanoparticle is covalently attached to the nanoparticle core (e.g. by attachment of a thiol group (—SH) on the outer layer to the surface of the gold core). In embodiments, the outer layer of the nanoparticle is non-covalently attached to the nanoparticle core (e.g. ionic electrostatic interactions with the gold core). For example, the negatively charged surface of the gold core may attach to a positively charged outer surface (e.g. chitosan, chitosan-cyclodextrin) through ionic interactions.

In embodiments, the outer layer includes a polymer. In embodiments, the polymer is Polyethylene glycol (PEG), polyethylenimine (PEI) or polyamidoamine (PAMAM). In embodiments, the polymer is Polyethylene glycol (PEG). In embodiments, the polymer is polyethylenimine (PEI). In embodiments, the polymer is polyamidoamine (PAMAM). In embodiments, the outer layer includes a cationic polysaccharide. In embodiments, the cationic polysaccharide includes chitosan. In embodiments, the cationic polysaccharide includes chitosan-cyclodextrin. Thus, in an embodiment, the outer layer is a chitosan polysaccharide attached to the nanoparticle gold core by non-covalent interactions. In another embodiment, the outer layer is a chitosan-cyclodextrin polysaccharide attached to the nanoparticle gold core by non-covalent interactions.

In embodiments, the outer layer includes an amino acid including a primary amine group. In embodiments, the outer layer includes a thiol (—SH) group. For example, the thiol group on the outer layer may be used to attach the outer layer to the nanoparticle core. Methods for the production of nanoparticles are further described in Sukumar, U. K.; Bose, R. J. C.; Malhotra, M.; Babikir, H. A.; Afjei, R.; Robinson, E.; Zeng, Y.; Chang, E.; Habte, F.; Sinclair, R.; Gambhir, S. S.; Massoud, T. F.; Paulmurugan, R., Intranasal delivery of targeted polyfunctional gold-iron oxide nanoparticles loaded with therapeutic microRNAs for combined theranostic multimodality imaging and presensitization of glioblastoma to temozolomide. Biomaterials 2019, 218, 119342., which is incorporated by reference herein in its entirety and for all purposes.

In embodiments, the pulmonary viral protein or nucleic acid encoding the protein is covalently attached to the nanoparticle. For example, a pulmonary viral protein or nucleic acid functionalized with a thiol may adsorb to the nanoparticle gold core. In embodiments, the pulmonary viral protein or nucleic acid is covalently attached to the outer layer of the nanoparticle. For example, the nanoparticle outer layer may include a first reactive moiety that is able to form a covalent bond with a second reactive moiety on the viral protein or nucleic acid encoding said viral protein. For example, a thiol group on the nanoparticle outer layer may react with a thiol group on the viral protein or nucleic acid to form a covalent disulfide bond. For example, a nucleic acid or protein modified with a covalent reactive moiety may be covalently attached to the nanoparticle outer layer using a variety of conjugation methods described herein and known in the art.

In embodiments, the pulmonary viral protein or nucleic acid is non-covalently attached to the nanoparticle. For example, the pulmonary viral protein or nucleic acid may attach to the nanoparticle by non-covalent bonds (e.g. electrostatic interactions (e.g. ionic bond, hydrogen bond, halogen bond), hydrophobic interactions). For example, a functionalized or non-functionalized protein may attach to the nanoparticle gold core through hydrophobic interactions. In embodiments, the pulmonary viral protein or nucleic acid is non-covalently attached to the outer layer of the nanoparticle. For example, a negatively charged nucleic acid may attach to a positively charged outer layer (e.g. chitosan) by non-covalent bonds (e.g. ionic electrostatic interactions).

In embodiments, the nucleic acid is deoxyribonucleic acid, In embodiments, the nucleic acid is ribonucleic acid. The nucleic acid may be chemically modified, such as to increase stability and/or cell penetration. The nucleic acids provided herein may include one or more reactive moieties, e.g., a covalent reactive moiety. A reactive moiety may be attached to the nucleic acid using any appropriate linker, such as a polymer linker known in the art (e.g. a polyethylene glygcol linker or equivalent). As used herein, the term "covalent reactive moiety" refers to a chemical moiety capable of chemically reaction with a second covalent reactive moiety (e.g. a functional group on a polymer (e.g. polymer outer layer)) to form a covalent bond. Similarly, the pulmonary viral protein provided herein including embodiments thereof may be modified (e.g. to increase stability and/or cell penetration). In embodiments, the pulmonary viral protein may be modified to include reactive moieties (e.g. thiol groups, etc.) as a means to attach to the nanoparticle (e.g. nanoparticle core, nanoparticle outer layer).

In embodiments, the complex provided herein includes a detectable moiety. The detectable moiety can be any known in the art and described herein. In embodiments, the detectable moiety is an enzyme, biotin, digoxigenin, a paramagnetic molecule, a contrast agent, gadolinium, a radioisotope, radionuclide, fluorodeoxyglucose, barium sulfate, thorium dioxide, gold, a fluorophore, a hapten, a protein, a fluorescent moiety, or a combination of two or more thereof. In embodiments, the contrast agent is a magnetic resonance imaging contrast agent, an X-ray contrast agent, or an iodinated contrast agent. In embodiments, the detectable agent is a fluorophore (e.g., fluorescein, rhodamine, coumarin, cyanine, or analogs thereof). In embodiments, the detectable agent is a chemiluminescent agent. In embodiments, the detectable agent is a radionuclide. In embodiments, the detectable agent is a radioisotope. In embodiments, the detectable agent is a paramagnetic molecule or a paramagnetic nanoparticle. The detectable moiety can be attached to the nanoparticle core, the outer layer of the nanoparticle, the pulmonary viral protein, or nucleic acid. In embodiments, the detectable moiety is an enzyme (e.g. a detectable protein (e.g. luciferase)). In embodiments, the complex includes a detectable protein (e.g. luciferase), wherein the protein is attached to the nanoparticle. In embodiments, the complex includes a nucleic acid (e.g. DNA, mRNA) encoding the detectable protein (e.g. luciferase), wherein the nucleic acid is attached to the nanoparticle.

The complex provided herein including embodiments thereof may further be characterized by size. As referred to herein, the size of the complex (e.g. the nanoparticle (e.g. core, core and outer layer) and pulmonary viral protein or nucleic acid) is the average diameter of the complex. Thus, in embodiments, the size of the complex is from about 20 nm to about 80 nm. In embodiments, the size of the complex is from about 25 nm to about 80 nm. In embodiments, the size of the complex is from about 30 nm to about 80 nm. In embodiments, the size of the complex is from about 35 nm to about 80 nm. In embodiments, the size of the complex is from about 40 nm to about 80 nm. In embodiments, the size of the complex is from about 45 nm to about 80 nm. In embodiments, the size of the complex is from about 50 nm to about 80 nm. In embodiments, the size of the complex is from about 55 nm to about 80 nm. In embodiments, the size of the complex is from about 60 nm to about 80 nm. In embodiments, the size of the complex is from about 65 nm to about 80 nm. In embodiments, the size of the complex is from about 70 nm to about 80 nm. In embodiments, the size of the complex is from about 75 nm to about 80 nm.

In embodiments, the size of the complex is from about 20 nm to about 75 nm. In embodiments, the size of the complex is from about 20 nm to about 70 nm. In embodiments, the size of the complex is from about 20 nm to about 65 nm. In embodiments, the size of the complex is from about 20 nm to about 60 nm. In embodiments, the size of the complex is from about 20 nm to about 55 nm. In embodiments, the size of the complex is from about 20 nm to about 50 nm. In embodiments, the size of the complex is from about 20 nm to about 45 nm. In embodiments, the size of the complex is from about 20 nm to about 40 nm. In embodiments, the size of the complex is from about 20 nm to about 35 nm. In embodiments, the size of the complex is from about 20 nm to about 30 nm. In embodiments, the size of the complex is from about 20 nm to about 25 nm. In embodiments, the size of the complex is about 20 nm, 25 nm, 30 nm, 35 nm, 40 nm, 45 nm, 50 nm, 55 nm, 60 nm, 65 nm, 70 nm, 75 or 80 nm.

In embodiments, the size of the complex is about 20 nm. In embodiments, the size of the complex is 20 nm. In embodiments, the size of the complex is about 25 nm. In embodiments, the size of the complex is 25 nm. In embodiments, the size of the complex is about 30 nm. In embodiments, the size of the complex is 30 nm. In embodiments, the size of the complex is about 35 nm. In embodiments, the size of the complex is 35 nm. In embodiments, the size of the complex is about 40 nm. In embodiments, the size of the complex is 40 nm. In embodiments, the size of the complex is about 45 nm. In embodiments, the size of the complex is 45 nm. In embodiments, the size of the complex is about 50 nm. In embodiments, the size of the complex is 50 nm. In embodiments, the size of the complex is about 55 nm. In embodiments, the size of the complex is 55 nm. In embodiments, the size of the complex is about 60 nm. In embodiments, the size of the complex is 60 nm. In embodiments, the size of the complex is about 65 nm. In embodiments, the size of the complex is 65 nm. In embodiments, the size of the complex is about 70 nm. In embodiments, the size of the complex is 70 nm. In embodiments, the size of the complex is about 75. In embodiments, the size of the complex is 75. In embodiments, the size of the complex is about 80 nm. In embodiments, the size of the complex is 80 nm.

In embodiments, the size of the complex is from about 30 nm to about 50 nm. In embodiments, the size of the complex is from about 32 nm to about 50 nm. In embodiments, the size of the complex is from about 34 nm to about 50 nm. In embodiments, the size of the complex is from about 36 nm to about 50 nm. In embodiments, the size of the complex is from about 38 nm to about 50 nm. In embodiments, the size of the complex is from about 40 nm to about 50 nm. In embodiments, the size of the complex is from about 42 nm to about 50 nm. In embodiments, the size of the complex is from about 44 nm to about 50 nm. In embodiments, the size of the complex is from about 46 nm to about 50 nm. In embodiments, the size of the complex is from about 48 nm to about 50 nm.

In embodiments, the size of the complex is from about 30 nm to about 48 nm. In embodiments, the size of the complex is from about 30 nm to about 46 nm. In embodiments, the size of the complex is from about 30 nm to about 44 nm. In embodiments, the size of the complex is from about 30 nm to about 42 nm. In embodiments, the size of the complex is from about 30 nm to about 40 nm. In embodiments, the size of the complex is from about 30 nm to about 38 nm. In embodiments, the size of the complex is from about 30 nm to about 36 nm. In embodiments, the size of the complex is from about 30 nm to about 34 nm. In embodiments, the size of the complex is from about 30 nm to about 32 nm. In embodiments, the size of the complex is about 30 nm, 32 nm, 34 nm, 38 nm, 40 nm, 42 nm, 44 nm, 48 nm, or 50 nm. In embodiments, the size of the complex is about 30 nm. In embodiments, the size of the complex is 30 nm. In embodiments, the size of the complex is about 32 nm. In embodiments, the size of the complex is 32 nm. In embodiments, the size of the complex is about 34 nm. In embodiments, the size of the complex is 34 nm. In embodiments, the size of the complex is about 36 nm. In embodiments, the size of the complex is 36 nm. In embodiments, the size of the complex is about 38 nm. In embodiments, the size of the complex is 38 nm. In embodiments, the size of the complex is about 40 nm. In embodiments, the size of the complex is 40 nm. In embodiments, the size of the complex is about 42 nm. In embodiments, the size of the complex is 42 nm. In embodiments, the size of the complex is about 44 nm. In embodiments, the size of the complex is 44 nm. In embodiments, the size of the complex is about 46 nm. In embodiments, the size of the complex is 46 nm. In embodiments, the size of the complex is about 48 nm. In embodiments, the size of the complex is 48 nm. In embodiments, the size of the complex is about 50 nm. In embodiments, the size of the complex is 50 nm.

In embodiments, the size (e.g. average diameter) of the nanoparticle core is about 4 nm to about 30 nm. In embodiments, the size of the nanoparticle core is about 6 nm to about 30 nm. In embodiments, the size of the nanoparticle core is about 8 nm to about 30 nm. In embodiments, the size of the nanoparticle core is about 10 nm to about 30 nm. In embodiments, the size of the nanoparticle core is about 12 nm to about 30 nm. In embodiments, the size of the nanoparticle core is about 14 nm to about 30 nm. In embodiments, the size of the nanoparticle core is about 16 nm to about 30 nm. In embodiments, the size of the nanoparticle core is about 18 nm to about 30 nm. In embodiments, the size of the nanoparticle core is about 20 nm to about 30 nm. In embodiments, the size of the nanoparticle core is about 22 nm to about 30 nm. In embodiments, the size of the nanoparticle core is about 24 nm to about 30 nm. In embodiments, the size of the nanoparticle core is about 26 nm to about 30 nm. In embodiments, the size of the nanoparticle core is about 28 nm to about 30 nm.

In embodiments, the size of the nanoparticle core is about 4 nm to about 28 nm. In embodiments, the size of the nanoparticle core is about 4 nm to about 26 nm. In embodiments, the size of the nanoparticle core is about 4 nm to about 24 nm. In embodiments, the size of the nanoparticle core is about 4 nm to about 22 nm. In embodiments, the size of the nanoparticle core is about 4 nm to about 18 nm. In embodiments, the size of the nanoparticle core is about 4 nm to about 16 nm. In embodiments, the size of the nanoparticle core is about 4 nm to about 14 nm. In embodiments, the size of the nanoparticle core is about 4 nm to about 12 nm. In embodiments, the size of the nanoparticle core is about 4 nm to about 10 nm. In embodiments, the size of the nanoparticle core is about 4 nm to about 8 nm. In embodiments, the size of the nanoparticle core is about 4 nm to about 6 nm. In embodiments, the size of the nanoparticle core is about 4 nm, 6 nm, 8 nm, 10 nm, 12, nm, 14 nm, 16 nm, 18 nm, 20 nm, 22, nm, 24 nm, 26 nm, 28 nm, or 30 nm. In embodiments, the size of the nanoparticle core is about 4 nm. In embodiments, the size of the nanoparticle core is 4 nm. In embodiments, the size of the nanoparticle core is about 6 nm. In embodiments, the size of the nanoparticle core is 6 nm. In embodiments, the size of the nanoparticle core is about 8 nm. In embodiments, the size of the nanoparticle core is 8 nm. In embodiments, the size of the nanoparticle core is about 10 nm. In embodiments, the size of the nanoparticle core is 10 nm. In embodiments, the size of the nanoparticle core is about 12 nm. In embodiments, the size of the nanoparticle core is 12 nm. In embodiments, the size of the nanoparticle core is about 14 nm. In embodiments, the size of the nanoparticle core is 14 nm. In embodiments, the size of the nanoparticle core is about 16 nm. In embodiments, the size of the nanoparticle core is 16 nm. In embodiments, the size of the nanoparticle core is about 18 nm. In embodiments, the size of the nanoparticle core is 18 nm. In embodiments, the size of the nanoparticle core is about 20 nm. In embodiments, the size of the nanoparticle core is 20 nm. In embodiments, the size of the nanoparticle core is about 22 nm. In embodiments, the size of the nanoparticle core is 22 nm. In embodiments, the size of the nanoparticle core is about 24 nm. In embodiments, the size of the nanoparticle core is 26 nm. In embodiments, the size of the nanoparticle core is about 28 nm. In embodiments, the size of the nanoparticle core is 28 nm. In embodiments, the size of the nanoparticle core is about 30 nm. In embodiments, the size of the nanoparticle core is 30 nm.

Vaccine and Pharmaceutical Compositions

The complex provided herein is contemplated to be particularly effective in vaccine compositions for preventing pulmonary viral infections. Applicant has found that the complex described herein effectively delivers nucleic acid cargo to the lungs. Delivery of the complex to the lungs results in an effective immune response against the protein encoded by the nucleic acid. Thus, in an aspect is provided a vaccine composition including a complex provided herein including embodiments thereof and a pharmaceutically acceptable excipient.

In embodiments, the vaccine composition further includes one or more of a stabilizer, an adjuvant, and a preservative. In embodiments, the vaccine composition includes a stabilizer. In embodiments, the vaccine composition includes an adjuvant. In embodiments, the vaccine composition includes a preservative.

In embodiments, said composition is formulated for nasal administration.

In an aspect is provided a pharmaceutical composition including a therapeutically effective amount of a complex described herein, including embodiments thereof, and a pharmaceutically acceptable excipient. In embodiments, the compositions provided herein are used for a therapeutic purpose. In some embodiments, a therapeutic purpose encompasses a prophylactic purpose (a purpose of preventing a disease or condition from occurring) and a treatment purpose (a purpose of treating an existing disease or condition). The pharmaceutical composition is contemplated to be effective for treating a pulmonary viral infection (e.g. Covid-19) or a condition associated with the viral infection. In embodiments, the complex, when administered to a subject, can induce an immune response, i.e. is immunogenic. This immunogenicity can be induced, at least in part, when one or more antigenic peptides from a pulmonary virus or one or more antigenic peptides encoded by the cargo nucleic acid are expressed in the subject.

Methods of Preventing and Treating a Viral Infection

The complex provided herein including embodiments thereof is particularly useful for treating or preventing pulmonary viral infections. Applicant has found that the complex induces antigen-specific immune response at the ports of entry (e.g. upper and lower respiratory tract) and areas affected (e.g. lungs) by pulmonary viruses. Thus, in an aspect is provided a method of treating or preventing a pulmonary viral disease in a subject in need of such treatment or prevention, the method including administering a therapeutically or prophylactically effective amount of a complex provided herein including embodiments thereof to the subject.

In embodiments, the complex is administered by an intranasal route. In embodiments, the complex is administered by an oro-nasal route. In embodiments, the complex is administered to the lungs.

In an aspect is provided a method of treating or preventing a pulmonary viral disease in a subject in need of such treatment or prevention, the method including administering a therapeutically or prophylactically effective amount of a vaccine composition provided herein including embodiments thereof to the subject.

In embodiments, the vaccine composition is administered by an intranasal route. In embodiments, the vaccine composition is administered by an oro-nasal route. In embodiments, the vaccine composition is administered to the lungs.

In embodiments, the composition including the complex provided herein including embodiments thereof has a prophylactic activity such that the vaccine can prevent or reduce a likelihood of the occurrence of a disease (e.g. COVID-19) or condition in a subject. In embodiments, where the composition is used for a prophylactic purpose, a subject can be an animal who does not have the disease or condition, e.g. a human who was not diagnosed with the disease or condition or who does not have a noticeable symptom associated with the disease or condition.

In embodiments, the composition including the complex described herein is used for a prophylactic purpose, especially in a subject who is considered predisposed of infection but presently does not have the viral disease. The prophylactic vaccine can be administered to the predisposed subject and prevent or reduce a likelihood of the occurrence of the viral disease in the subject.

In embodiments, the composition has a therapeutic effect such that the composition can be used to treat a disease (e.g., a pulmonary vial disease) or condition. The composition can exhibit one or more anti-viral activity, e.g. reduction of viral particle number, reduction and/or inhibition of viral replication and infectivity.

In embodiments, the composition including the complex provided herein can provide both therapeutic and prophylactic effects by delivering two separate pulmonary viral proteins or nucleic acids sequences encoding for said proteins in a single composition. Thus, in embodiments, the composition can (1) induce a more immediate treatment effect to the existing pulmonary viral infection or condition with the first immunogenic viral protein or fragment thereof, and (2) induce adaptive immunity in the subject with the second immunogenic viral protein or fragment thereof for future occurrence of a different pulmonary viral disease or condition. Thus, in embodiments, the composition includes a complex including two or more different pulmonary viral proteins or nucleic acids encoding the same wherein each protein independently exhibits a therapeutic or prophylactic effect, respectively.

Methods of Inducing an Immune Response

In an aspect is provided a method for immunizing a subject susceptible to a pulmonary viral disease, the method including administering a complex provided herein including embodiments thereof to the subject, under conditions such that antibodies that bind to the pulmonary viral protein or fragment thereof are produced.

In an aspect is provided a method for immunizing a subject susceptible to a pulmonary viral disease, the method including administering a vaccine composition provided herein including embodiments thereof to the subject, under conditions such that antibodies that bind to the pulmonary viral protein or fragment thereof are produced.

In embodiments, the antibodies are IgG, IgA or IgM antibodies. In embodiments, the antibodies are IgG antibodies. In embodiments, the antibodies are IgA antibodies. In embodiments, the antibodies are IgM antibodies.

In embodiments, the pulmonary viral disease is COVID-19. In embodiments, the pulmonary viral disease is MERS. In embodiments, the pulmonary viral disease is Severe acute respiratory syndrome (SARS). In embodiments, the pulmonary viral disease is an HRSV infection. In embodiments, the pulmonary viral disease is an HPV infection. In embodiments, the pulmonary viral disease is an HRV infection. In embodiments, the pulmonary viral disease is an HCoV infection. In embodiments, the pulmonary viral disease is an HBoV infection. In embodiments, the pulmonary viral disease is an HMPV infection. In embodiments, the pulmonary viral disease is an ADV infection. In embodiments, the pulmonary viral disease causes one or more syndromes as listed in Table 2. In embodiments, the pulmonary viral disease causes a distant inflammatory effect.

Methods for monitoring induction of an immune response are well known in the art, such as by measuring antibody titers.

Methods of Administration

In an aspect is provided a method for delivering the compositions provided herein including embodiments thereof to a subject as to treat or prevent pulmonary viral infection in the subject. In embodiments, the composition includes a complex including (a) a nanoparticle including a gold core; and (b) a pulmonary viral protein or fragment thereof, or a nucleic acid encoding the pulmonary viral protein or fragment thereof, wherein the pulmonary viral protein or nucleic acid is attached to the nanoparticle. In embodiments, the composition can be administered to a subject in an effective amount that is sufficient to achieve at least part of the intended effects in the subject.

"Administration," "administering" and the like, when used in connection with a composition refer both to direct administration, which may be administration to cells in vitro, administration to cells in vivo, administration to a subject by a medical professional or by self-administration by the subject and/or to indirect administration, which may be the act of prescribing a composition of the disclosure. Typically, an effective amount is administered, which amount can be determined by one of skill in the art. Compositions (e.g., complex) may be administered to cells by, for example, addition of the composition to the cell culture media or injection in vivo. Administration to a subject can be achieved by, for example, through inhalation (e.g. intranasal route, oro-nasal route).

In embodiments, the composition provided herein including embodiments thereof are provided as a pulmonary pharmaceutical composition comprising a pulmonary pharmaceutical excipient. The terms "pulmonary pharmaceutical composition" and the like refer to pharmaceutical compositions intended for pulmonary administration (e.g. intranasal route, oro-nasal route). The terms "pulmonary administration" and the like refer, in the usual and customary sense, to administration to achieve inhalation therapy (e.g. intranasal route, oro-nasal route). The term "inhalation therapy" and the like refer to direct delivery of medications to the lungs by inhalation. In embodiments, the complexes provided herein including embodiments thereof are effective when delivered directly to the lung by an inhaled drug delivery system. The term "pulmonary pharmaceutical liquid" refers to a pulmonary pharmaceutical composition which is a liquid. The terms "pulmonary pharmaceutical solid," "pulmonary pharmaceutical solid" and the like refer to a pulmonary pharmaceutical composition which is a solid (e.g., a powder).

In embodiments, the composition provided herein is provided in an inhaled drug delivery systems. In embodiments, the inhaled drug delivery system is a (i) nebulizer; (ii) a pressurized metered-dose inhaler (pMDI); or (iii) a dry powder inhaler (DPI). Nebulizers are distinctly different from both pMDIs and DPIs, in that the active agent is dissolved or suspended in a polar liquid, e.g., water. In contrast, pMDIs and DPIs are bolus drug delivery devices that contain active agent (e.g., nanoparticle complex), suspended or dissolved in a nonpolar volatile propellant or in a dry powder mix that is fluidized when the patient inhales.

pMDIs and DPIs have considerably reduced treatment time compared with nebulizers. The term "pulmonary pharmaceutical delivery device" and the like refer to an inhaled drug delivery system suitable for delivery (e.g., intranasal, oro-nasal delivery, etc.) of a pharmaceutical composition.

The dosage and frequency (single or multiple doses) administered to a subject can vary depending upon a variety of factors, for example, whether the subject suffers from another disease, its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compositions described herein including embodiments thereof. Adjustment and manipulation of established dosages (e.g., frequency and duration) are well within the ability of those skilled in the art.

In embodiments, the composition provided herein including embodiments thereof is administered in a dose (or an amount) wherein about 2 ug to about 50 ug of nucleic acid (e.g. DNA or RNA encoding a pulmonary viral protein) is delivered to a subject. In embodiments, the composition is administered in a dose wherein about 4 ug to about 50 ug of nucleic acid is delivered to a subject. In embodiments, the composition is administered in a dose wherein about 8 ug to about 50 ug of nucleic acid is delivered to a subject. In embodiments, the composition is administered in a dose wherein about 10 ug to about 50 ug of nucleic acid is delivered to a subject. In embodiments, the composition is administered in a dose wherein about 12 ug to about 50 ug of nucleic acid is delivered to a subject. In embodiments, the composition is administered in a dose wherein about 14 ug to about 50 ug of nucleic acid is delivered to a subject. In embodiments, the composition is administered in a dose wherein about 16 ug to about 50 ug of nucleic acid is delivered to a subject. In embodiments, the composition is administered in a dose wherein about 18 ug to about 50 ug of nucleic acid is delivered to a subject. In embodiments, the composition is administered in a dose wherein about 20 ug to about 50 ug of nucleic acid is delivered to a subject. In embodiments, the composition is administered in a dose wherein about 22 ug to about 50 ug of nucleic acid is delivered to a subject. In embodiments, the composition is administered in a dose wherein about 24 ug to about 50 ug of nucleic acid is delivered to a subject. In embodiments, the composition is administered in a dose wherein about 26 ug to about 50 ug of nucleic acid is delivered to a subject. In embodiments, the composition is administered in a dose wherein about 28 ug to about 50 ug of nucleic acid is delivered to a subject. In embodiments, the composition is administered in a dose wherein about 30 ug to about 50 ug of nucleic acid is delivered to a subject. In embodiments, the composition is administered in a dose wherein about 32 ug to about 50 ug of nucleic acid is delivered to a subject. In embodiments, the composition is administered in a dose wherein about 34 ug to about 50 ug of nucleic acid is delivered to a subject. In embodiments, the composition is administered in a dose wherein about 36 ug to about 50 ug of nucleic acid is delivered to a subject. In embodiments, the composition is administered in a dose wherein about 38 ug to about 50 ug of nucleic acid is delivered to a subject. In embodiments, the composition is administered in a dose wherein about 40 ug to about 50 ug of nucleic acid is delivered to a subject. In embodiments, the composition is administered in a dose wherein about 42 ug to about 50 ug of nucleic acid is delivered to a subject. In embodiments, the composition is administered in a dose wherein about 44 ug to about 50 ug of nucleic acid is delivered to a subject. In embodiments, the composition is administered in a dose wherein about 46 ug to about 50 ug of nucleic acid is delivered to a subject. In embodiments, the composition is administered in a dose wherein about 48 ug to about 50 ug of nucleic acid is delivered to a subject.

In embodiments, the composition is administered in a dose wherein about 2 ug to about 48 ug of nucleic acid is delivered to a subject. In embodiments, the composition is administered in a dose wherein about 2 ug to about 46 ug of nucleic acid is delivered to a subject. In embodiments, the composition is administered in a dose wherein about 2 ug to about 44 ug of nucleic acid is delivered to a subject. In embodiments, the composition is administered in a dose wherein about 2 ug to about 42 ug of nucleic acid is delivered to a subject. In embodiments, the composition is administered in a dose wherein about 2 ug to about 40 ug of nucleic acid is delivered to a subject. In embodiments, the composition is administered in a dose wherein about 2 ug to about 38 ug of nucleic acid is delivered to a subject. In embodiments, the composition is administered in a dose wherein about 2 ug to about 36 ug of nucleic acid is delivered to a subject. In embodiments, the composition is administered in a dose wherein about 2 ug to about 34 ug of nucleic acid is delivered to a subject. In embodiments, the composition is administered in a dose wherein about 2 ug to about 32 ug of nucleic acid is delivered to a subject. In embodiments, the composition is administered in a dose wherein about 2 ug to about 30 ug of nucleic acid is delivered to a subject. In embodiments, the composition is administered in a dose wherein about 2 ug to about 28 ug of nucleic acid is delivered to a subject. In embodiments, the composition is administered in a dose wherein about 2 ug to about 26 ug of nucleic acid is delivered to a subject. In embodiments, the composition is administered in a dose wherein about 2 ug to about 24 ug of nucleic acid is delivered to a subject. In embodiments, the composition is administered in a dose wherein about 2 ug to about 22 ug of nucleic acid is delivered to a subject. In embodiments, the composition is administered in a dose wherein about 2 ug to about 20 ug of nucleic acid is delivered to a subject. In embodiments, the composition is administered in a dose wherein about 2 ug to about 18 ug of nucleic acid is delivered to a subject. In embodiments, the composition is administered in a dose wherein about 2 ug to about 16 ug of nucleic acid is delivered to a subject. In embodiments, the composition is administered in a dose wherein about 2 ug to about 14 ug of nucleic acid is delivered to a subject. In embodiments, the composition is administered in a dose wherein about 2 ug to about 12 ug of nucleic acid is delivered to a subject. In embodiments, the composition is administered in a dose wherein about 2 ug to about 10 ug of nucleic acid is delivered to a subject. In embodiments, the composition is administered in a dose wherein about 2 ug to about 8 ug of nucleic acid is delivered to a subject. In embodiments, the composition is administered in a dose wherein about 2 ug to about 6 ug of nucleic acid is delivered to a subject. In embodiments, the composition is administered in a dose wherein about 2 ug to about 4 ug of nucleic acid is delivered to a subject. In embodiments, the composition is administered in a dose wherein about 2 ug, 4 ug, 6 ug, 8 ug, 10 ug, 12 ug, 14 ug, 16 ug, 18 ug, 20 ug, 22 ug, 24 ug, 26 ug, 28 ug, 30 ug, 32 ug, 34 ug, 36 ug, 38 ug, 40 ug, 42 ug, 44 ug, 46 ug, 48 ug or 50 ug of nucleic acid is delivered to a subject. In embodiments, the composition is administered in a dose wherein 2 ug of nucleic acid is delivered to a subject. In embodiments, the composition is administered in a dose wherein 4 ug of nucleic acid is delivered to a subject. In embodiments, the composition is administered in a dose wherein 6 ug of nucleic acid is delivered to a subject. In embodiments, the composition is administered in a dose wherein 8 ug of nucleic acid is delivered to a subject. In embodiments, the composition is administered in a dose wherein 10 ug of nucleic acid is delivered to a subject. In embodiments, the composition is administered in a dose wherein 12 ug of nucleic acid is delivered to a subject. In embodiments, the composition is administered in a dose wherein 14 ug of nucleic acid is delivered to a subject. In embodiments, the composition is administered in a dose wherein 16 ug of nucleic acid is delivered to a subject. In embodiments, the composition is administered in a dose wherein 18 ug of nucleic acid is delivered to a subject. In embodiments, the composition is administered in a dose wherein 20 ug of nucleic acid is delivered to a subject. In embodiments, the composition is administered in a dose wherein 22 ug of nucleic acid is delivered to a subject. In embodiments, the composition is administered in a dose wherein 24 ug of nucleic acid is delivered to a subject. In embodiments, the composition is administered in a dose wherein 26 ug of nucleic acid is delivered to a subject. In embodiments, the composition is administered in a dose wherein 28 ug of nucleic acid is delivered to a subject. In embodiments, the composition is administered in a dose wherein 30 ug of nucleic acid is delivered to a subject. In embodiments, the composition is administered in a dose wherein 32 ug of nucleic acid is delivered to a subject. In embodiments, the composition is administered in a dose wherein 34 ug of nucleic acid is delivered to a subject. In embodiments, the composition is administered in a dose wherein 36 ug of nucleic acid is delivered to a subject. In embodiments, the composition is administered in a dose wherein 38 ug of nucleic acid is delivered to a subject. In embodiments, the composition is administered in a dose wherein 40 ug of nucleic acid is delivered to a subject. In embodiments, the composition is administered in a dose wherein 42 ug of nucleic acid is delivered to a subject. In embodiments, the composition is administered in a dose wherein 44 ug of nucleic acid is delivered to a subject. In embodiments, the composition is administered in a dose wherein 46 ug of nucleic acid is delivered to a subject. In embodiments, the composition is administered in a dose wherein 48 ug of nucleic acid is delivered to a subject. In embodiments, the composition is administered in a dose wherein 50 ug of nucleic acid is delivered to a subject.

In embodiments, the composition is administered in a dose wherein about 10 ug to about 20 ug of nucleic acid is delivered to a subject. In embodiments, the composition is administered in a dose wherein about 12 ug to about 20 ug of nucleic acid is delivered to a subject. In embodiments, the composition is administered in a dose wherein about 14 ug to about 20 ug of nucleic acid is delivered to a subject. In embodiments, the composition is administered in a dose wherein about 16 ug to about 20 ug of nucleic acid is delivered to a subject. In embodiments, the composition is administered in a dose wherein about 18 ug to about 20 ug of nucleic acid is delivered to a subject.

In embodiments, the composition is administered in a dose wherein about 10 ug to about 18 ug of nucleic acid is delivered to a subject. In embodiments, the composition is administered in a dose wherein about 10 ug to about 16 ug of nucleic acid is delivered to a subject. In embodiments, the composition is administered in a dose wherein about 10 ug to about 14 ug of nucleic acid is delivered to a subject. In embodiments, the composition is administered in a dose wherein about 10 ug to about 12 ug of nucleic acid is delivered to a subject. In embodiments, the composition is administered in a dose wherein about 10 ug, 12 ug, 14 ug, 16 ug, 18 ug or 20 ug of nucleic acid is delivered to a subject. In embodiments, the composition is administered in a dose wherein about 10 ug of nucleic acid is delivered to a subject. In embodiments, the composition is administered in a dose wherein 10 ug of nucleic acid is delivered to a subject. In embodiments, the composition is administered in a dose wherein about 12 ug of nucleic acid is delivered to a subject. In embodiments, the composition is administered in a dose wherein 12 ug of nucleic acid is delivered to a subject. In embodiments, the composition is administered in a dose wherein about 14 ug of nucleic acid is delivered to a subject. In embodiments, the composition is administered in a dose wherein 14 ug of nucleic acid is delivered to a subject. In embodiments, the composition is administered in a dose wherein about 16 ug of nucleic acid is delivered to a subject. In embodiments, the composition is administered in a dose wherein 16 ug of nucleic acid is delivered to a subject. In embodiments, the composition is administered in a dose wherein about 18 ug of nucleic acid is delivered to a subject. In embodiments, the composition is administered in a dose wherein 18 ug of nucleic acid is delivered to a subject. In embodiments, the composition is administered in a dose wherein about 20 ug of nucleic acid is delivered to a subject. In embodiments, the composition is administered in a dose wherein 20 ug of nucleic acid is delivered to a subject.

Nanoparticle Compositions

In an aspect is provided a nanoparticle including a plurality of nucleic acids attached thereto and plurality of proteins attached thereto, wherein each of the plurality of nucleic acids encode for a different SARS-CoV-2 viral protein, and each of said plurality of proteins is a different SARS-CoV-2 viral protein. In embodiments, the nanoparticle is biocompatible. In embodiments, the nanoparticle includes a core, wherein said core includes gold. In embodiments, the core of the nanoparticle is a gold-iron oxide core.

In embodiments, the nanoparticle includes a core and an outer layer, wherein said outer layer includes chitosan-cyclodextrin polymers. In embodiments, the plurality of nucleic acids and the plurality of proteins are attached to the outer layer of the nanoparticle. In embodiments, the one or more nucleic acids includes an RNA sequence encoding the SARS-CoV-2 viral proteins. In embodiments, the RNA sequence is an mRNA sequence. In embodiments, the SARS-CoV-2 viral proteins are selected from the group consisting of an S protein, N protein, M protein, and E protein.

In an aspect is provided a vaccine formulation including a nanoparticle as provided herein including embodiments thereof, and a pharmaceutically acceptable excipient. In embodiments, the vaccine formulation further includes a vaccine excipient. In embodiments, the vaccine excipient is a stabilizer, an adjuvant or a preservative. In embodiments, the vaccine formulation includes a plurality of nanoparticles.

In an aspect is provided a method of preventing or treating COVID-19 in a subject in need thereof, the method including administering to said subject a composition including an effective amount of a vaccine as provided herein including embodiments thereof, or a nanoparticle as provided herein including embodiments thereof, to a subject in need thereof. In embodiments, the composition is administered via the intra-nasal route. In embodiments, the composition is administered via the oro-nasal route.

In embodiments, the composition is administered to the respiratory tract. In embodiments, the composition is administered to the respiratory tract, including exposure to Waldeyer's ring of lymphoid tissue. In embodiments, the composition is administered to the lungs. In embodiments, the composition is administered to the respiratory tract (including exposure to Waldeyer's ring of lymphoid tissue) and the lungs.

In embodiments, the composition includes a plurality of nanoparticles.

In an aspect is provided a method of preventing or treating COVID-19 in a subject, the method including administering a composition including an effective amount of a vaccine as provided herein including embodiments thereof, or a nanoparticle provided herein including embodiments thereof, to a subject in need thereof. In embodiments, delivery can be through intranasal or oro-nasal delivery. In embodiments, airway targeting of multiple mRNAs in one anti-SARS-CoV-2 vaccine is performed. In embodiments, provided herein are combined nano-biotechnological and theranostic strategy for vaccine development against COVID-19. In embodiments, provided hererin is an RNA vaccine against SARS-CoV-2 delivered directly into the airways via the IN or oro-nasal route. In embodiments, provided herein is an RNA multivalent vaccine produced by robust expression of mRNA encoding a plurality of SARS-CoV-2 surface antigens (e.g. S, N, M and E proteins) or fragments thereof and a plurality of surface antigens (e.g. S, N, M, and E proteins) or fragments thereof. In embodiments, provided herein is an engineered polyfunctional NP with multiple components tailored specifically for IN or oro-nasal administration and subsequent targeting of respiratory airway columnar ciliated cells (and their progenitor cells) expressing ACE2 receptors, to deliver synthetic mRNA sequences of 'viral' antigens, as well as a plurality of S, N, M, and E proteins. In embodiments, provided herein is an in vitro evaluation of the uptake and functional effects of SARS-CoV-2 antigens by measuring their expression, cell surface display, and antibody recognition after transfection in mammalian lung cells using PolyGION-CD-CS hybrid polymer NPs. In embodiments, provided herein is an evaluation in mice of an mRNA multivalent vaccine incorporating all four surface antigens of SARS-CoV-2, as well as the S, N, M, and E proteins, using PolyGION-CD-CS hybrid polymer NPs via the IN or oro-nasal route to evaluate their in vivo immune response in mouse models.

EMBODIMENTS

P Embodiment 1: A nanoparticle comprising a plurality of nucleic acids attached thereto and plurality of proteins attached thereto, wherein each of the plurality of nucleic acids encode for a different SARS-CoV-2 viral protein, and each of said plurality of proteins is a different SARS-CoV-2 viral protein.

P Embodiment 2: The nanoparticle of P embodiment 1, wherein the nanoparticle comprises a core, wherein said core comprises gold.

P Embodiment 3: The nanoparticle of P embodiment 2, wherein the core of the nanoparticle is a gold-iron oxide core.

P Embodiment 4: The nanoparticle of P embodiment 1, wherein said nanoparticle comprises a core and an outer layer, where said outer layer comprises chitosan-cyclodextrin polymers.

P Embodiment 5: The nanoparticle of P embodiment 4, wherein said plurality of nucleic acids and said plurality of proteins are attached to said outer layer.

P Embodiment 6: The nanoparticle of P embodiment 5, wherein the one or more nucleic acids comprise an RNA sequence encoding said SARS-CoV-2 viral proteins.

P Embodiment 7: The nanoparticle of P embodiment 5, wherein the SARS-CoV-2 viral proteins are selected from the group consisting of an S protein, N protein, M protein, and E protein.

P Embodiment 8: A vaccine formulation comprising the nanoparticle of one of P embodiments 1-7 and a pharmaceutically acceptable excipient.

P Embodiment 9: The vaccine formulation of P embodiment 8 further comprising a vaccine excipient.

P Embodiment 10: The vaccine formulation of P embodiment 9, wherein the vaccine excipient is a stabilizer, an adjuvant or a preservative.

P Embodiment 11: A method of preventing or treating COVID-19 in a subject in need thereof, the method comprising administering to said subject a composition comprising an effective amount of the vaccine of one of P embodiments 8-10 or the nanoparticle of one of P embodiments 1-7 to a subject in need thereof.

P Embodiment 12: The method of P embodiment 11, wherein the composition is administered via the intra-nasal route.

P Embodiment 13: The method of P embodiment 11, wherein the composition is administered via the oro-nasal route.

P Embodiment 14: The method of P embodiment 11, wherein the composition is administered to the lungs.

P Embodiment 15: A method of preventing or treating a SARS-CoV-2 viral infection in a subject in need thereof, the method comprising administering a composition comprising an effective amount of the vaccine of one of P embodiments 8-10 or the nanoparticle of one of P embodiments 1-7 to a subject in need thereof.

EMBODIMENTS

Embodiment 1: A complex comprising: (a) a nanoparticle comprising a gold core; and (b) a pulmonary viral protein or fragment thereof, or a nucleic acid encoding said pulmonary viral protein or fragment thereof, wherein said pulmonary viral protein or nucleic acid is attached to said nanoparticle.

Embodiment 2: The complex of embodiment 1, comprising a plurality of pulmonary viral proteins or fragments thereof.

Embodiment 3: The complex of embodiment 2, wherein said plurality of pulmonary viral proteins comprise different pulmonary viral proteins.

Embodiment 4: The complex of embodiment 1, comprising a plurality of nucleic acids encoding said pulmonary viral protein or fragment thereof.

Embodiment 5: The complex of embodiment 4, wherein said plurality of nucleic acids encode different pulmonary viral proteins or fragments thereof.

Embodiment 6: The complex of any one of embodiments 1 to 5, wherein said pulmonary virus is human respiratory syncytial virus (HRSV), human parainfluenza virus (HPV) Human rhinovirus (HRV), Adenovirus (ADV), Human coronavirus (HCoV), Coronavirus associated with SARS (SARS-CoV), Human metapneumovirus (HMPV) or Human bocavirus (HBoV).

Embodiment 7: The complex of embodiment 6 wherein said pulmonary virus is SARS-CoV-2.

Embodiment 8: The complex of embodiment 7, wherein said pulmonary viral protein or fragment thereof is S protein, N protein, M protein, or E protein.

Embodiment 9: The complex of any one of embodiments 1 to 8, wherein said gold core is a gold-iron oxide core.

Embodiment 10: The complex of any one of embodiments 1 to 9, wherein said nanoparticle comprises an outer layer.

Embodiment 11: The complex of embodiment 10, wherein said outer layer is covalently attached to said gold core.

Embodiment 12: The complex of embodiment 10, wherein said outer layer is non-covalently attached to said gold core.

Embodiment 13: The complex of any one of embodiments 10 to 12, wherein said outer layer comprises a polymer.

Embodiment 14: The complex of any one of embodiments 10 to 13, wherein said outer layer comprises a cationic polysaccharide.

Embodiment 15: The complex of embodiment 14, wherein said cationic polysaccharide comprises chitosan.

Embodiment 16: The complex of embodiment 14, wherein said cationic polysaccharide comprises chitosan-cyclodextrin.

Embodiment 17: The complex of any one of embodiments 1 to 16, wherein said pulmonary viral protein or nucleic acid is covalently attached to said nanoparticle.

Embodiment 18: The complex of embodiment 17, wherein said pulmonary viral protein or nucleic acid is covalently attached to said outer layer of said nanoparticle.

Embodiment 19: The complex of any one of embodiments 1 to 16, wherein said pulmonary viral protein or nucleic acid is non-covalently attached to said nanoparticle.

Embodiment 20: The complex of embodiment 19, wherein said pulmonary viral protein or nucleic acid is non-covalently attached to said outer layer of said nanoparticle.

Embodiment 21: The complex of any one of embodiments 1 to 20, wherein said nucleic acid is deoxyribonucleic acid.

Embodiment 22: The complex of any one of embodiments 1 to 20, wherein said nucleic acid is ribonucleic acid.

Embodiment 23: The complex of any one of embodiments 1 to 22, wherein said complex is from about 20 nm to about 80 nm in diameter.

Embodiment 24: The complex of any one of embodiments 1 to 23, wherein said complex is about 40 nm in diameter.

Embodiment 25: A vaccine composition comprising the complex of any one of embodiments 1 to 24 and a pharmaceutically acceptable excipient.

Embodiment 26: The vaccine composition of embodiment 25, further comprising one or more of a stabilizer, an adjuvant, and a preservative.

Embodiment 27: The vaccine composition of embodiment 25 or 26, wherein said composition is formulated for nasal administration.

Embodiment 28: A method of treating or preventing a pulmonary viral disease in a subject in need of such treatment or prevention, said method comprising administering a therapeutically or prophylactically effective amount of the complex of any one of embodiments 1 to 24 to said subject.

Embodiment 29: The method of embodiment 28, wherein the complex is administered by an intranasal route.

Embodiment 30: The method of embodiment 28, wherein the complex is administered by an oro-nasal route.

Embodiment 31: The method of embodiment 28, wherein the complex is administered to the lungs.

Embodiment 32: A method of treating or preventing a pulmonary viral disease in a subject in need of such treatment or prevention, said method comprising administering a therapeutically or prophylactically effective amount of the vaccine composition of any one of embodiments 25 to 27 to said subject.

Embodiment 33: The method of embodiment 32, wherein the composition is administered via the intra-nasal route.

Embodiment 34: The method of embodiment 32, wherein the composition is administered via the oro-nasal route.

Embodiment 35: The method of embodiment 32, wherein the composition is administered to the lungs.

Embodiment 36: A method for immunizing a subject susceptible to a pulmonary viral disease, the method comprising administering the complex of any one of embodiments 1 to 24 to said subject, under conditions such that antibodies that bind to said pulmonary viral protein or fragment thereof are produced.

Embodiment 37: The method of embodiment 36, wherein said antibodies are IgG, IgA or IgM antibodies.

EXAMPLES

Example 1: Introduction to Exemplary Experiments

Nucleic acid vaccines are safe and easy to develop because their production involves making genetic material only, and not the virus itself. Anti-COVID-19 nucleic acid vaccines entail delivery of specific portions of viral RNA that code for individual proteins or protein fragments, into human cells, which then produce copies of the viral proteins against the delivered RNA. The mRNA vaccines are capable of inducing antigen-specific T- and B-cell responses.[17-18] By Apr. 30, 2020, at least 20 teams were studying the use of SARS-CoV-2 DNA or RNA to prompt an immune response. When placed in contrast to traditional or DNA vaccines, an RNA vaccine has several important benefits: (1) An RNA vaccine is not made with pathogen particles, so they are non-infectious, and the messenger RNA (mRNA) strand is rapidly degraded once the protein is made. (2) Unlike pDNA that relies on cell and nuclear membrane poration to reach the nucleus for transcription and further translation into proteins, it is sufficient for the RNA strand to gain access to the cytosol for translation. (3) DNA expression cassettes carry the theoretical risks of genome integration, insertional mutagenesis, long-term expression, and the induction of anti-DNA antibodies. (4) Some of the early clinical trial results indicate that an RNA vaccine can generate a reliable immune response and is well-tolerated by healthy individuals, with negligible side effects. (5) It can be produced more rapidly, and is more easily standardized, which improves responsiveness to emerging outbreaks.

Notably, most nucleic acid vaccines encode the S protein alone. Instead, provided herein, inter alia, is a multivalent (multi-antigen) vaccine strategy for the robust expression of mRNA encoding two or more surface antigens (e.g. S, N, M and E proteins) of SARS-CoV-2. Even though SARS-CoV-2 possesses significant homology with other coronaviruses, it also possesses substantial variations in some antigens. These variations are clearly reflected in SARS-CoV-2 by differences in the mode of its infection, pathogenicity, spread, and severity of the disease. Hence, prediction-based approaches of possible viral protein(s) for designing epitope vaccines may not be promising owing to their poor success rate. A multivalent mRNA vaccine expressing two or more surface antigens provides better success.

Provided herein, inter alia, are vaccines that can be therapeutic for infected individuals (e.g. by inducing immune antibodies while preventing further infection by blocking ACE2 receptors) and/or prophylactic for uninfected individuals. Engineering mRNA sequences has rendered synthetic mRNAs more translatable than ever before—the in vivo half-life of mRNA can be regulated through use of various base modifications and delivery methods. Thus, efficient in vivo delivery is achieved by formulating mRNA into/onto carrier vehicles, allowing rapid uptake and expression in host cell cytoplasm. In aspects, intranasal (IN) delivery is combined with a novel nanocarrier for a multivalent mRNA vaccine strategy against COVID-19 in the clinical setting.

Provided herein, inter alia, are efficient nanocarriers to deliver RNA vaccines via the IN route to express antigens against SARS-CoV-2. The use of an efficient delivery system for IN delivery can dramatically reduce the doses needed to generate potent immune responses, without an additional conventional adjuvant. Hence, described herein are nanoformulations carrying synthetic mRNAs encoding two or more of SARS-CoV-2 S, N, M, and E proteins or fragments thereof as independent transcripts, or two or more of S, N, M, and E proteins or fragments thereof. Loading mRNA and proteins on a biocompatible nanoparticle (NP) and coupling this with a clinically practical delivery method provides an easy, safe, minimally invasive, and tissue-specific method for successful expression of a multivalent SARS-CoV-2 vaccine for immunization against COVID-19.

We previously developed a molecularly targeted theranostic nanoformulation against the brain cancer, glioblastoma (GBM). This nanoformulation includes a 50 nm polyfunctional gold-iron oxide NP (termed polyGION) used to deliver therapeutic microRNAs to mouse GBMs via IN delivery.[21] PolyGIONs surface functionalized with cyclodextrin-chitosan (CD-CS) hybrid polymers provide an efficient platform for surface loading of negatively charged RNAs through electrostatic interactions.[21] Moreover, to be of value as therapeutic agents, the targeted delivery of polyGIONs, and visualization of their trafficking would be essential in pre-clinical studies, at least. Hence, we developed and experimentally validated the IN delivery of GION core-shells (that enable CT and MR imaging), coated with GBM cell-targeting T7 peptide, functionalized with conjugated CD-CS hybrid polymer, and pre-loaded with therapeutic miRNAs as an effective theranostic system against GBM.[21] We pre-clinically evaluated this nanoformulation after IN delivery in mice bearing orthotopically implanted GBMs, and found prominent suppression of GBM proliferation and concurrent improvement in animal survival rates.[21] Furthermore, the presence of polyGIONs enabled simultaneous multimodality imaging of IN delivery and trafficking to intracranial tumors.[21]

We found in our mouse studies that trafficking of the IN-administered polyGION-CD-CS NPs was determined by the breathing rate of mice at the time of treatment. When we administered polyGION-CD-CS NPs to mice under deep anesthesia, most of the delivered NPs stuck to the nasal mucosal and trafficked over time to pathological regions of the brain. In contrast, when we administered the NPs in awake mice, we found a predominant amount of NPs moved beyond the nasal cavity, into the airways, and then settled in the distal lungs. Capitalizing on this observation, the non-invasive respiratory mucosal targeted delivery of viral RNAs specific to each antigen using our polyGION-CD-CS nanoformulation provides a new anti-SARS-CoV-2 multivalent vaccine to directly target the airways and lungs-precisely the main initial target organs for COVID-19 disease, to activate pulmonary immune responses. A similar approach using recombinant adenovirus-based vaccine expressing S protein of MERS-CoV was found to induce significant immune responses when administered IN to BALB/c mice.[12] We demonstrated previously that gold NPs are non-toxic.[22-24]. In aspects, the iron oxide component from the polyGION-CD-CS nanoformulation can be removed.

The advantages of the IN and respiratory airway route (e.g., by nasal spray/drip, or oro-nasal nebulizer or inhaler) include avoidance of circulating blood, reduced systemic side effects and hepatic/renal clearance, creating airway and lung resident memory T cell responses, and the possibility of practical repeated or chronic vaccine administration. Moreover, its non-invasiveness, painless and convenient administration to individuals as a nasal spray or inhaler with high compliance, and rapid onset of action, provide novel features for an anti-SARS-CoV-2 vaccine.

Example 2: Results for IN Delivery of mRNA Loaded Nanoparticles

PolyGION-CD-CS NPs Serve as a Biocompatible Non-Toxic Platform for IN Delivery of Therapeutics.

Figure 2A:
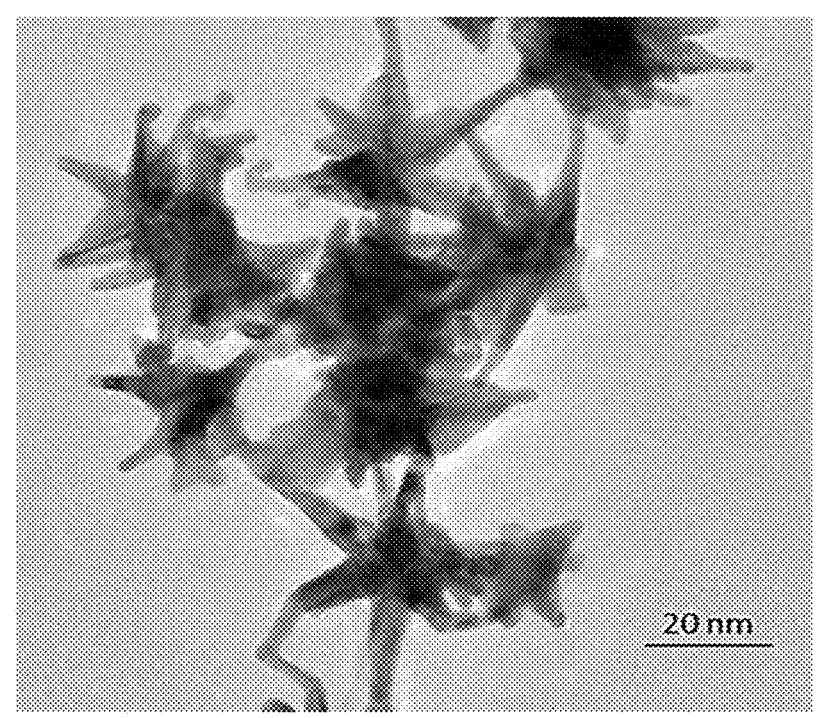
FIGS. 2A-2F present an exemplary in vitro evaluation of PolyGION-CD-CS nanoparticles, and their efficiency in delivering FLuc-mRNA in cells by functional expression analysis.
Figure 2B:
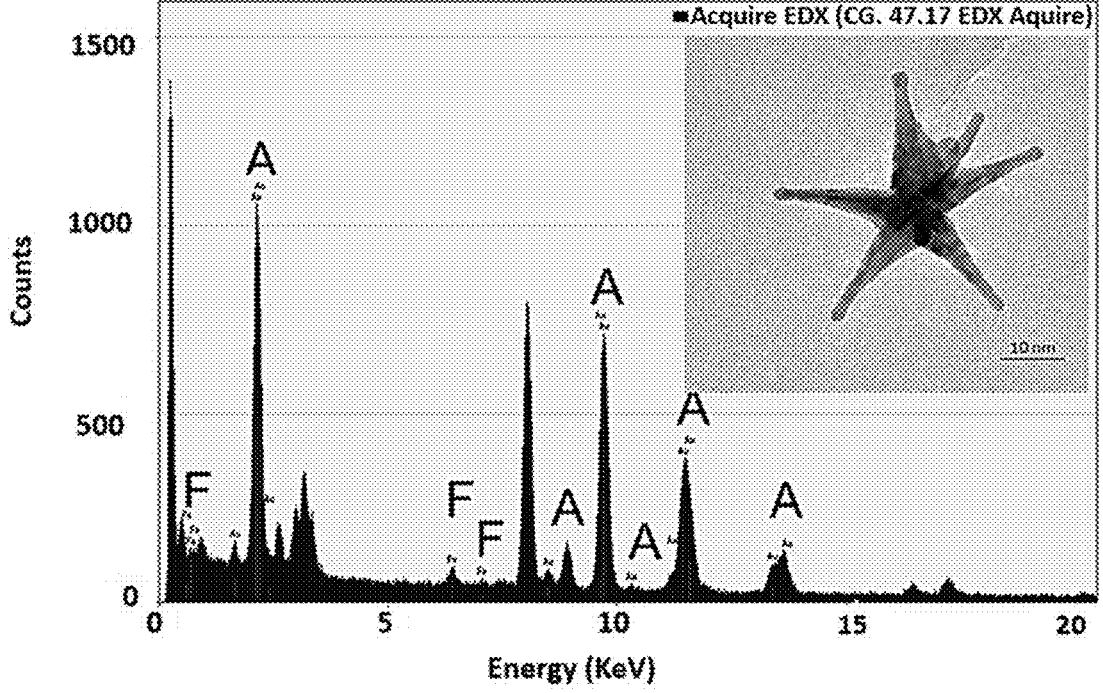
Figure 2C:
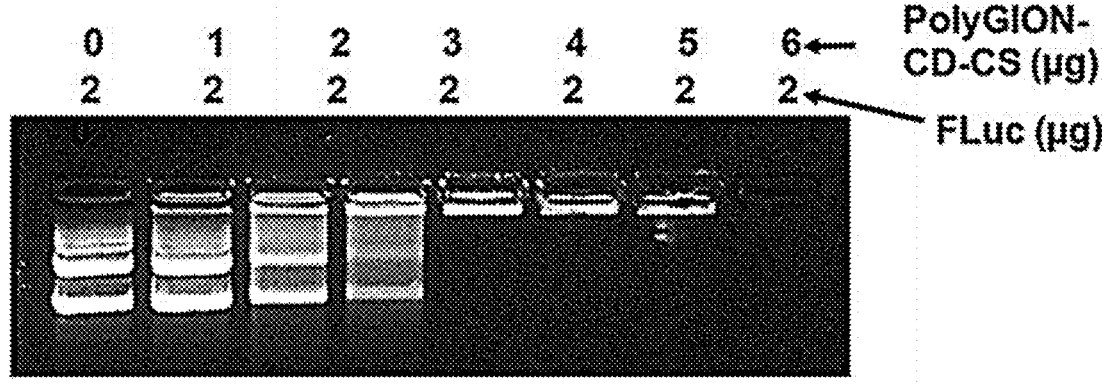
Figure 2D:
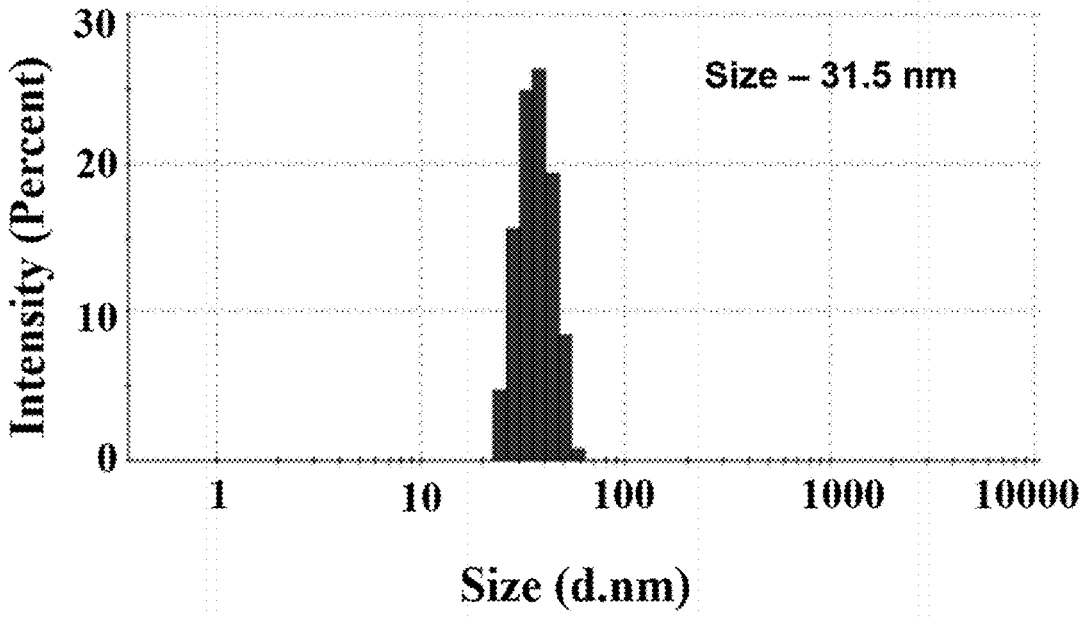
Figure 2E:
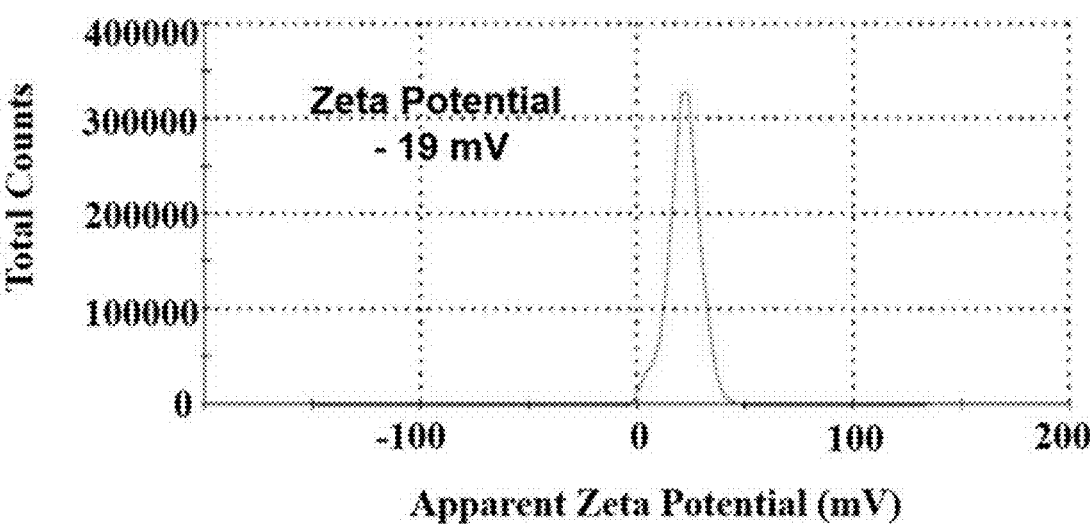
Figure 2F:
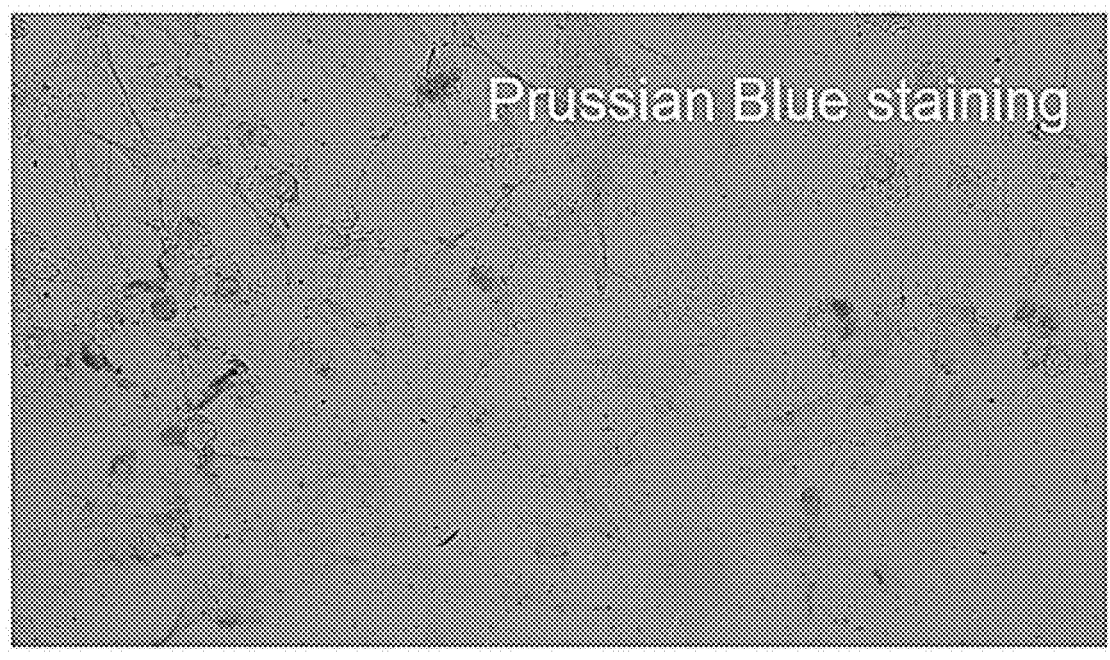

We tested the feasibility of delivering mRNAs encoding SARS-CoV-2 antigens to mouse lungs as vaccines to induce a respiratory mucosal and pulmonary immune response, using FLuc-mRNA as a reporter. FLuc-mRNA delivery facilitates monitoring delivery, stability, and expression of delivered RNA in lungs by using bioluminescence imaging (BLI). We tested the loading efficiency of FLuc-mRNA in PolyGION-CD-CS by measuring the N/P ratio (FIG. 2C), and the transfection efficiency in cells (HEK293 and A549 cells) using optical BLI. Our results showed a strong and mRNA dose-dependent expression of luciferase in both cell types. We also confirmed the presence of intracellular Poly-GIONs by using Prussian blue staining (FIG. 2F).

Figure 3:
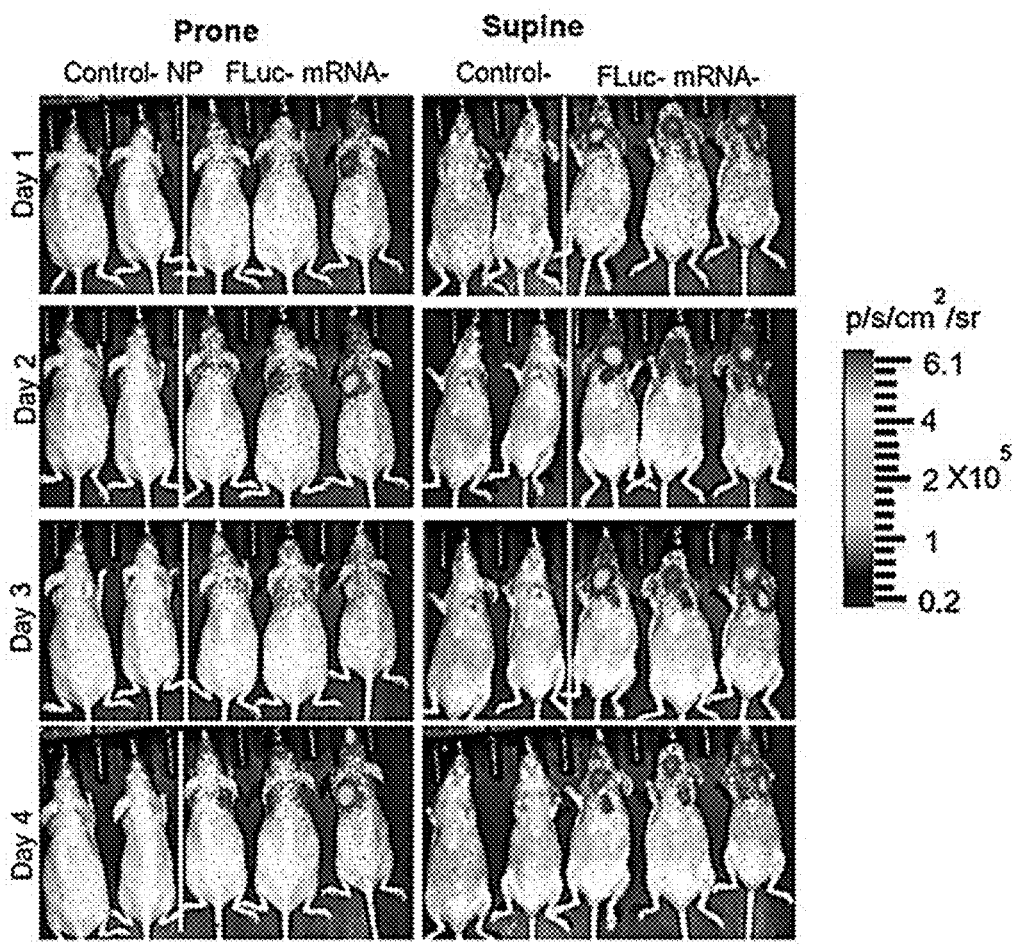
FIG. 3 shows optical bioluminescence imaging of animals delivered with FLuc-mRNA using PolyGION-CD-CS NPs. Mice treated with a dose of 2 µg of FLuc-mRNA every day and images acquired 24 h after treatment.
Figure 4A:
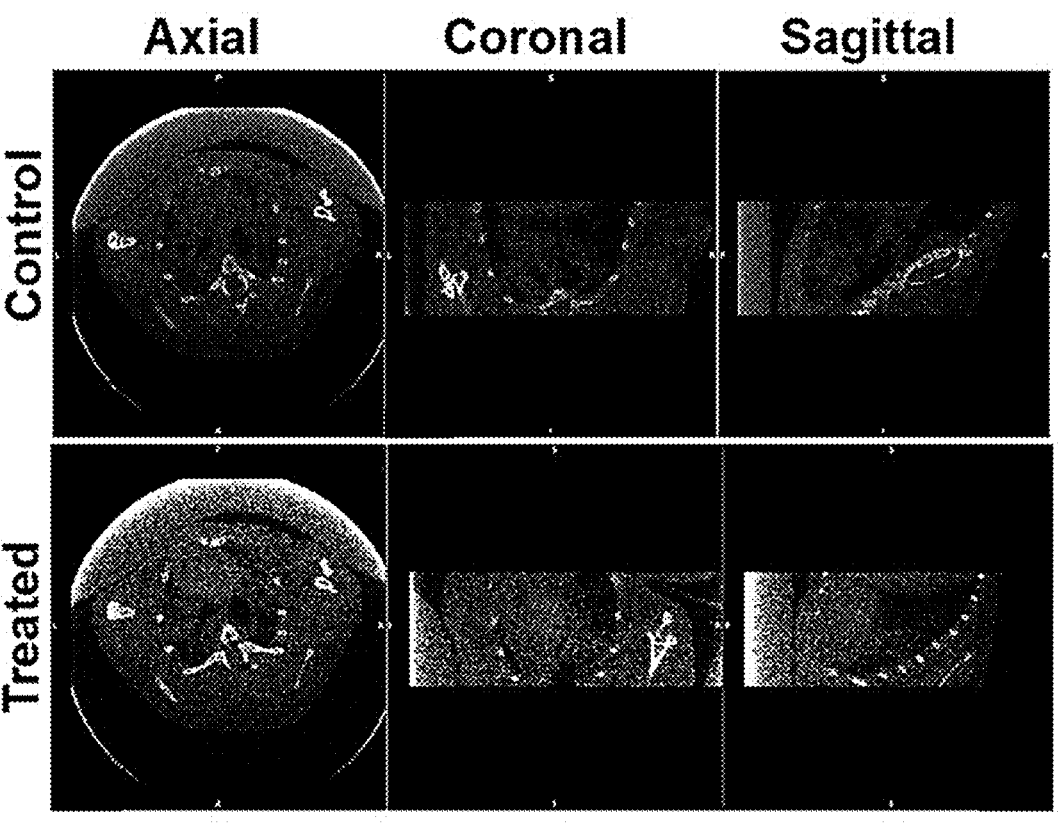
FIGS. 4A-4C present exemplary in vivo micro-computed tomography (microCT) and optical imaging, and ex vivo bioluminescence imaging (BLI) of tissues after five doses of PolyGION-CD-CS-FLuc-mRNA.
Figure 4B:
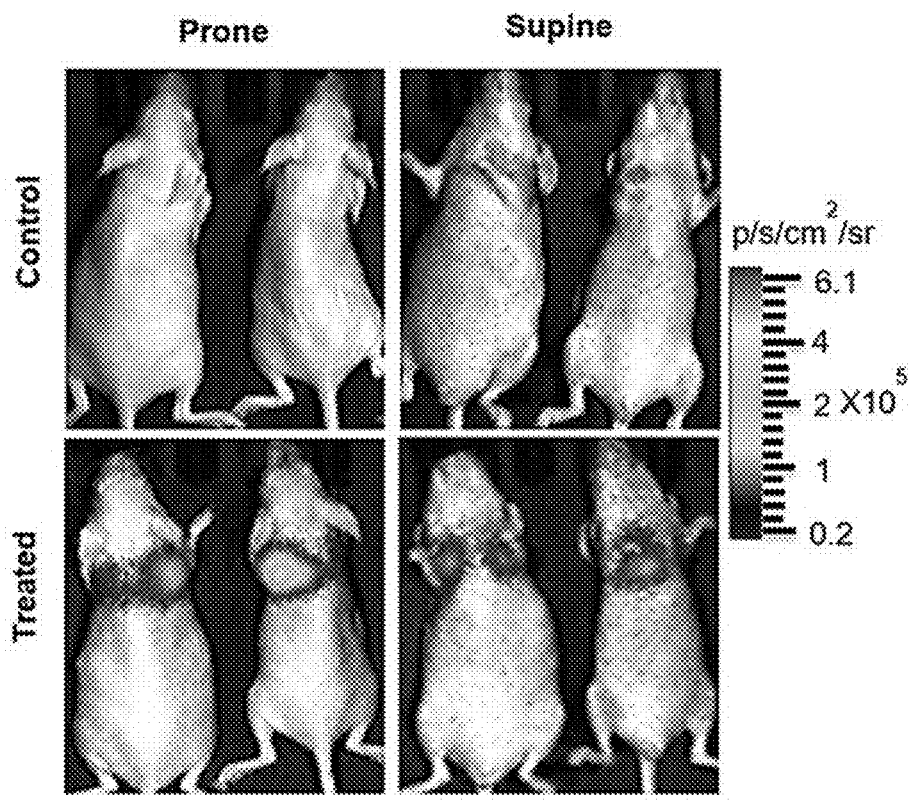
Figure 4C:
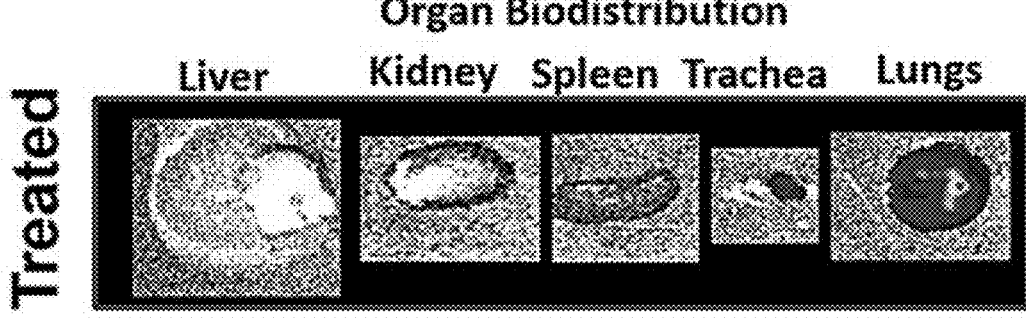
Figure 5:
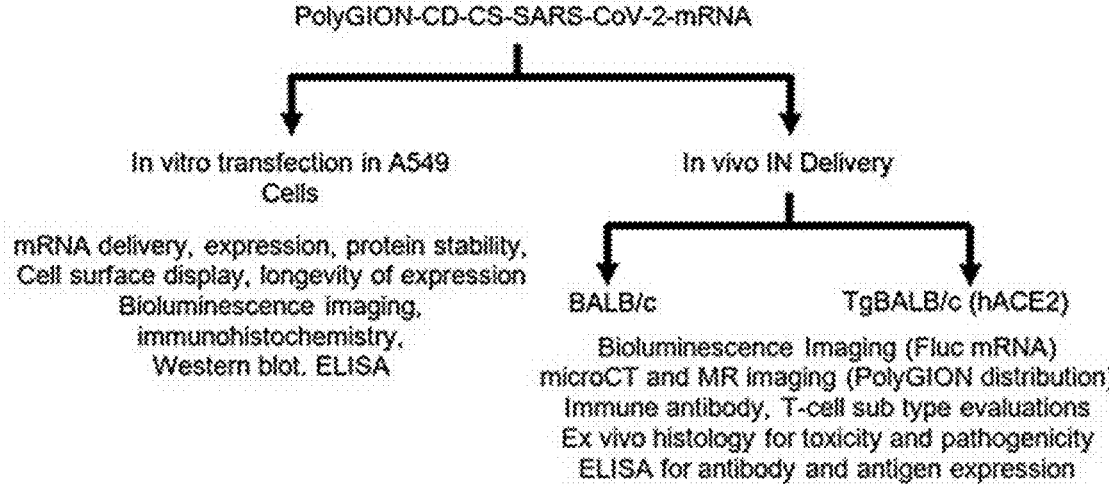
FIG. 5 is a schematic illustration of in vitro and in vivo experimental workflow with the assays proposed to assess transfection, immune response, and pathogenicity.
Figure 6:
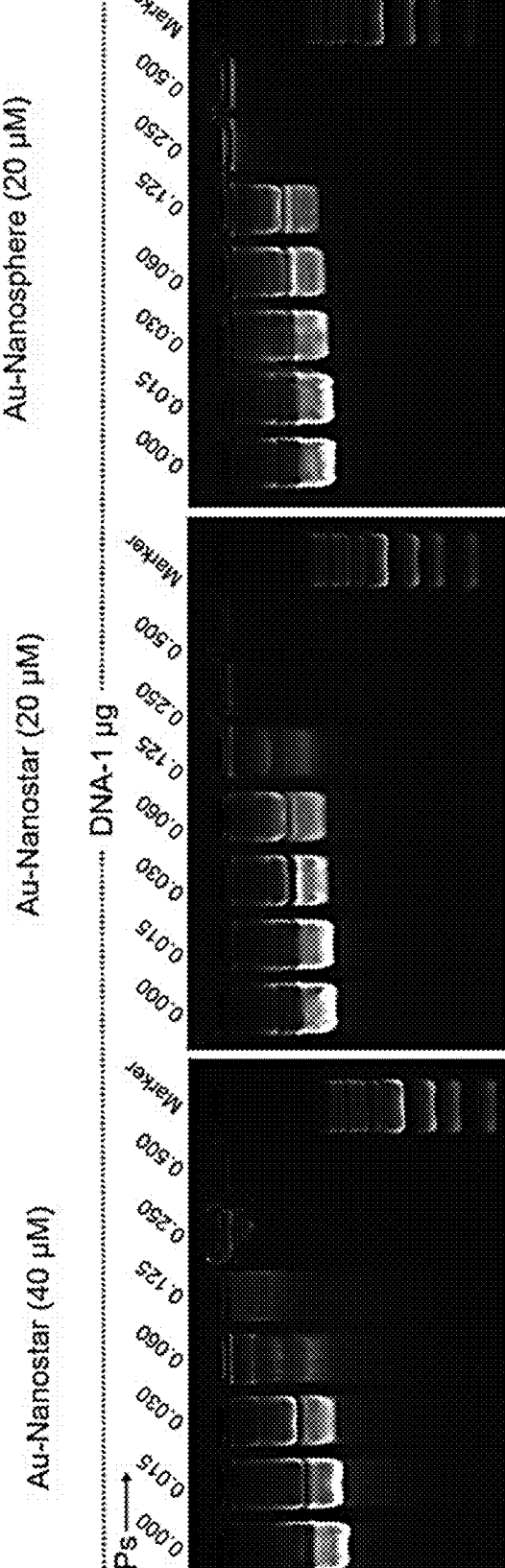
FIG. 6 illustrates the DNA loading efficiency of Au-Chitosan Nanoparticles of various shapes and sizes. The left and middle panel show data for Au-Nanostar nanoparticles between 0.015 and 0.5 nm in diameter and the right panel shows data for Au-Nanosphere nanoparticles between 0.015 and 0.5 nm in diameter.
Figure 7A:
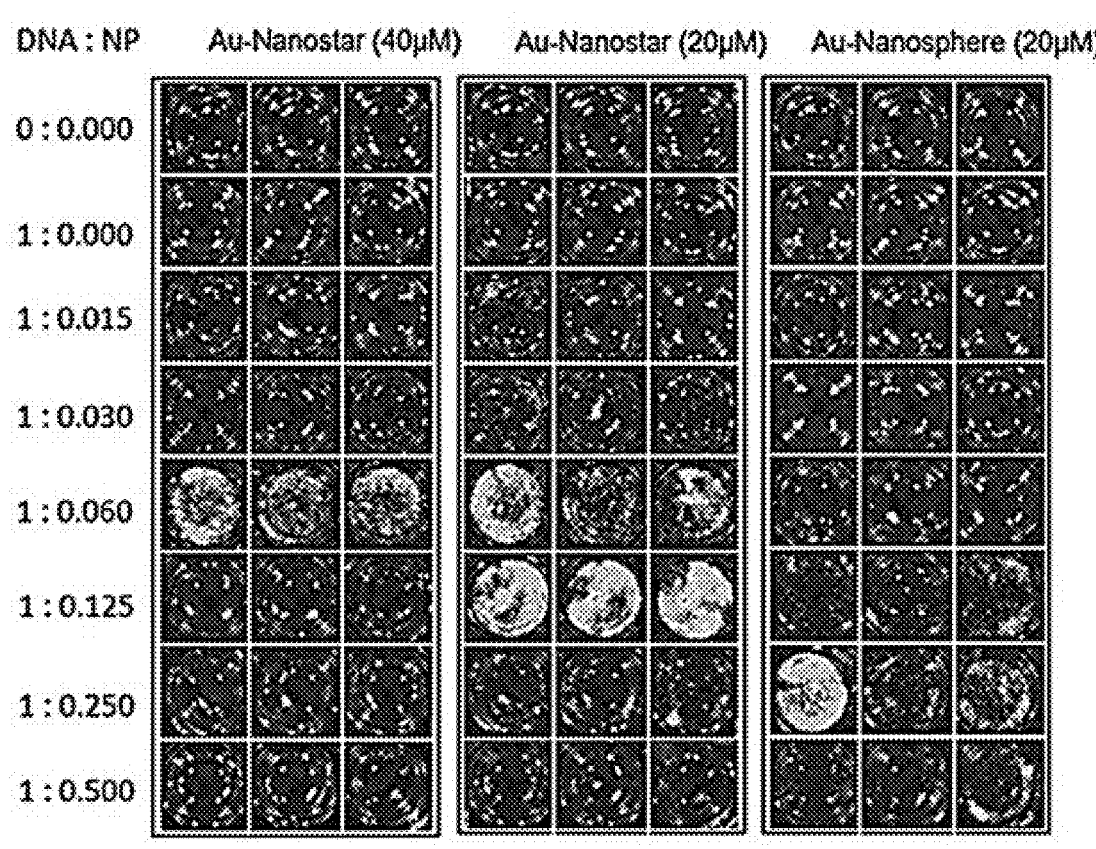
FIGS. 7A-7B shows the transfection efficiency of Au—CH Nanoparticles of different sizes and shape into cells.
Figure 7B:
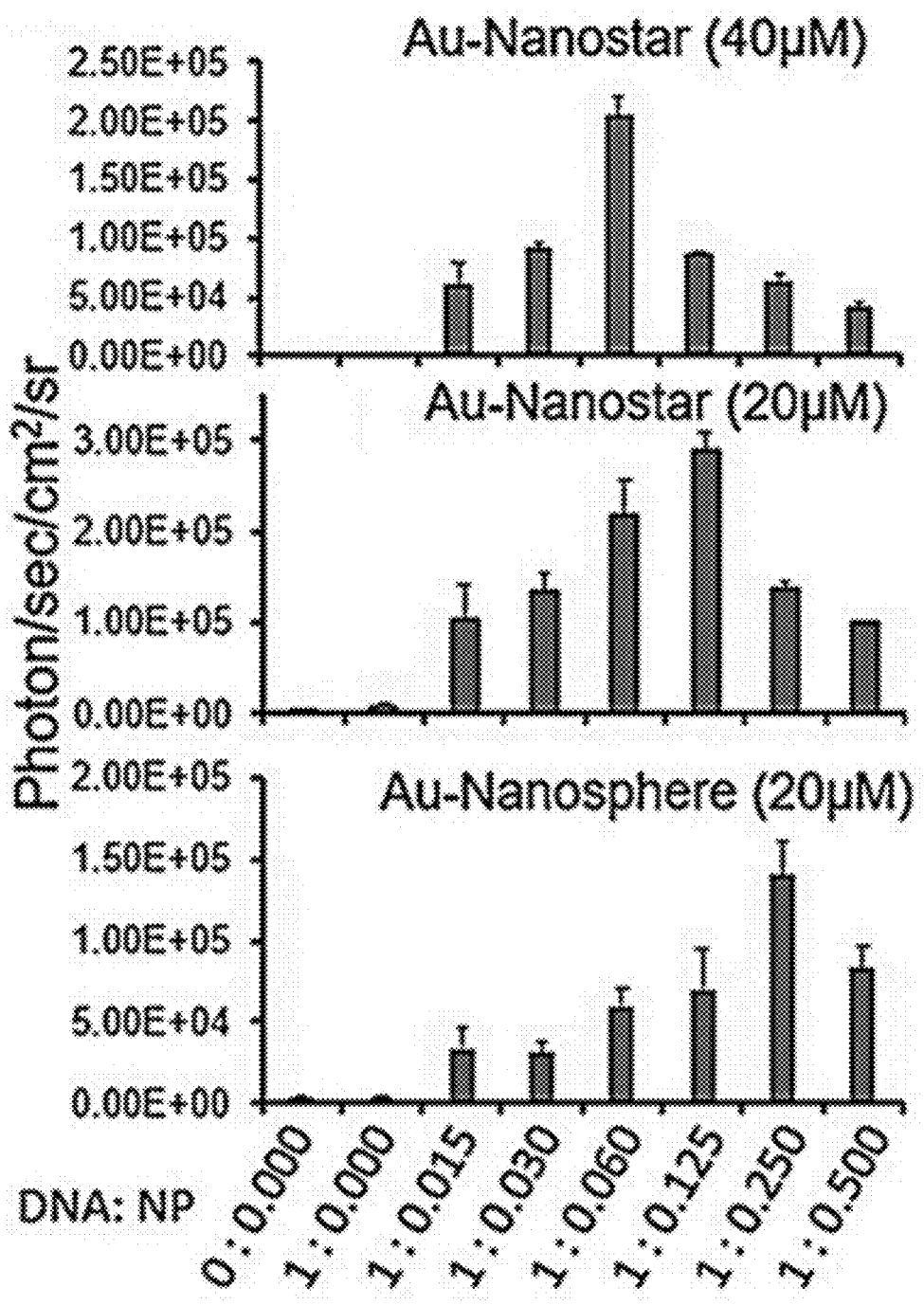
Figure 8A:
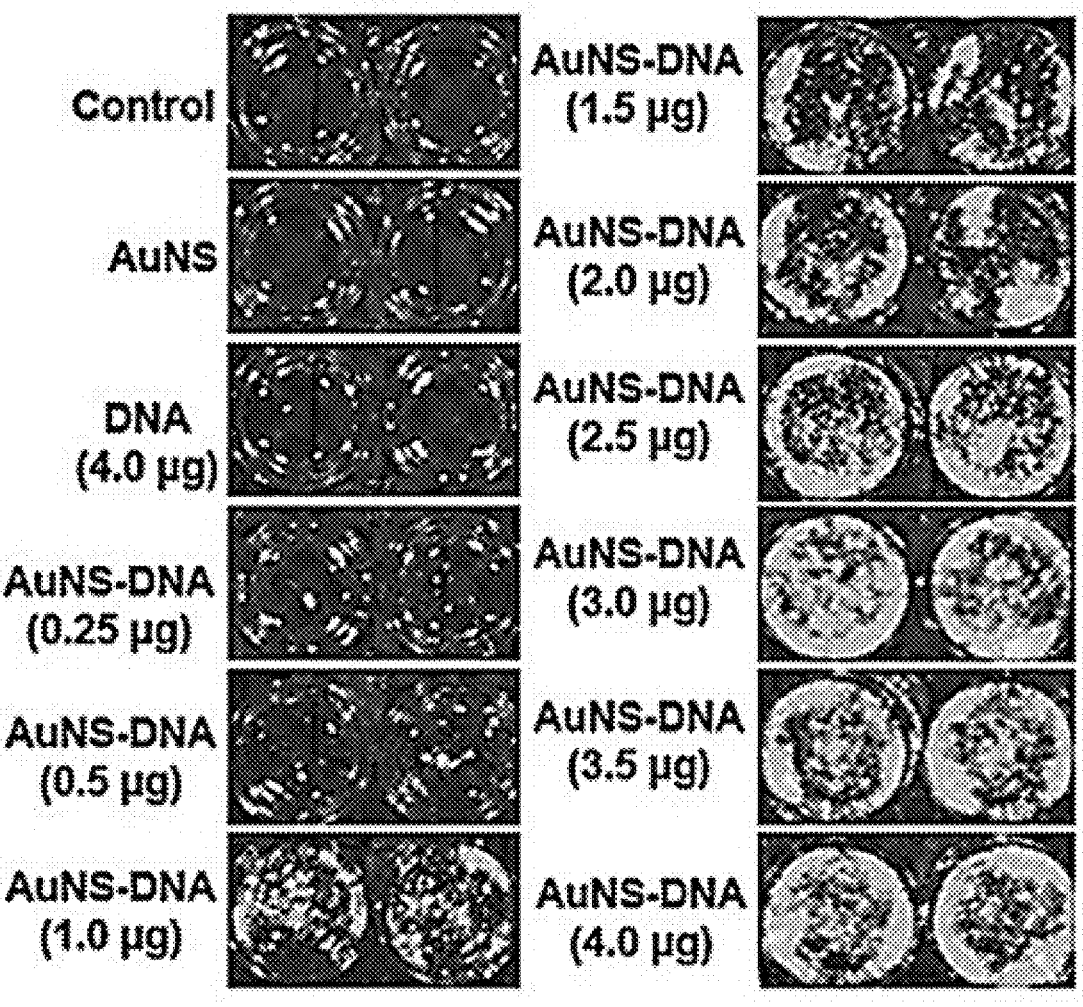
FIGS. 8A-8C illustrate DNA dose dependent transfection by Au—NS Nanoparticles in Mammalian Cells.
Figure 8B:
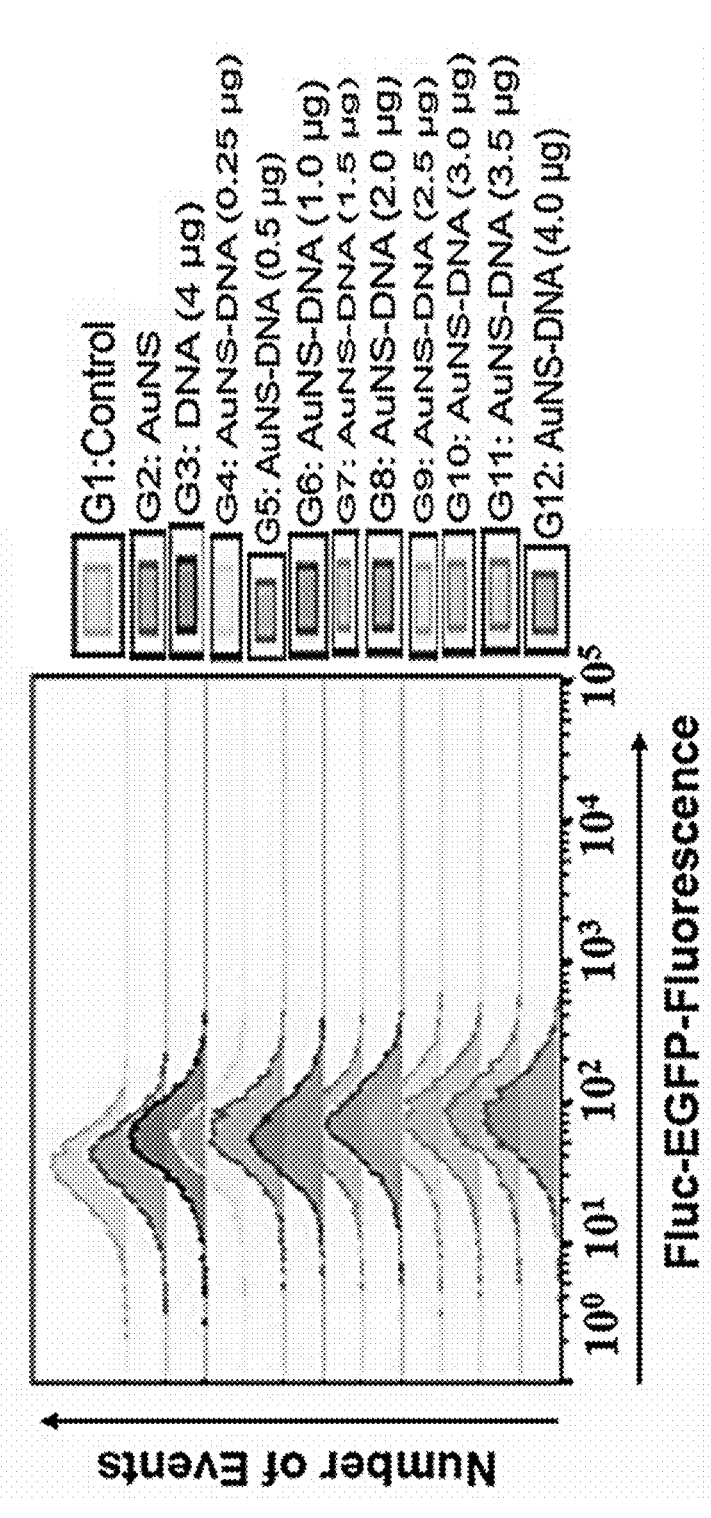
Figure 8C:
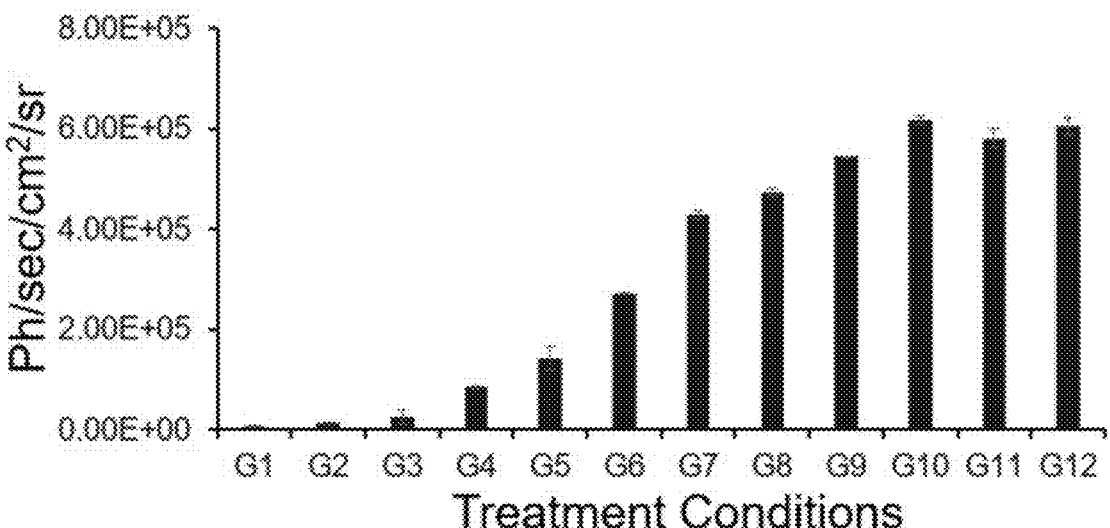

Monitoring of PolyGION-CD-CS NP-Mediated IN Delivery of FLuc-mRNA Expression and Lung Resident GIONs Using BLI The PolyGION-CD-CS-FLuc-mRNA complex was investigated for IN delivery to mice. 5 µl of NP complex was administered 4 times in each nostril (a total of 20 µl for each dose; 2 µg of mRNA equivalent). The NP complex was delivered in awake mice. BLI was obtained at 24 hr time points after delivery, and dosage administration was continued each day. After 6 days, mice were BLI imaged in vivo and ex vivo after sacrifice. The mice showed strong BLI signals in the trachea after the first dose, and strong signals in the lungs 48 hr later. The signals in the lungs were strikingly strong after five doses (FIG. 3). Pre-sacrifice BLI showed localized signals in the lungs (FIG. 4B). Ex vivo analysis (lung, spleen, liver, trachea, and kidneys) showed strong BLI signals in lungs and tracheobronchial junctions. There was no signal in other organs, including spleen (FIG. 4C).

Example 3: Research Design and Methods

Identification of the Optimal Ratio of the SARS-CoV-2 mRNAs by Evaluating their Expression, Cell Surface Display, and Antibody Recognition after Transfection in Mammalian Lung Cells Using IN Compatible PolyGION-CD-CS Hybrid Polymer NPs.

The expression of viral antigens by mRNAs anywhere in host tissues can deliver antibody responses to the viral proteins and protect patients against infection. However, pulmonary immune responses are also important for pathogens that infect the respiratory tract, especially to allow rapid recovery or to prevent disease development. A respiratory mucosal immune response would also retain lung resident memory B and T cells that provide long-lasting neutralizing immunity to the virus.[21] Since there were no clinical immunological data to help us identify the epitopes of SARS-CoV-2 antigens that can be effective in inducing host humoral and cellular immune responses while producing neutralizing antibodies, we delivered all surface proteins of the virus as antigens to induce antibody responses as a tactic to rapidly develop an anti-COVID-19 vaccine. While not wishing to be bound by theory, expression of at least two antigens (S, N, E and M proteins) of SARS-CoV-2 could produce a multivalent immune response that includes memory B and T-cell responses. This can be more effective if the antigens are expressed in respiratory mucosa and the lungs.

As a first step towards achieving this goal, we will evaluate the mRNA-mediated expression of antigens in cell culture studies for their robustness, protein stability, and the ratio of different mRNAs required to achieve near equivalent levels of all the antigens, before expanding them into in vivo studies. The use of mRNAs with C-terminal signal peptide derived from human PDGF receptor (PDGFR) allows display of antigens on the surfaces of transfected cells, and therefore to more effectively induce immune responses in vivo.[26-27] This may facilitate their later applications in humans compared to plain antigens that more likely remain intracellularly and, therefore, are less effective for immune cell recognition.

Evaluation of the Stability, Antigen Expression, and Surface Display of mRNAs in Cells Using C-Terminal PDGFR Signal Peptide Coding Sequence Tagged SARS-CoV-2 Antigens In Vitro in Lung Cells after Transfection Using Poly-GION-CD-CS Hybrid polymerNPs.

Since we use the C-terminal peptide sequence of human PDGFR in clinical applications to display the antigens on cell surfaces, it is important to evaluate the effect of antigen(s) surface display on targeted cells. Here, we optimize the expression, stability, and surface display of antigens by in vitro transfections of lung cells. We also use Firefly luciferase (FLuc) reporter mRNA for co-transfection experiments to evaluate transfection efficiency and normalization by using BLI.

Experimental Methods

We use full length spike protein (1273 aa), nucleoprotein (479 aa), envelope protein (75 aa) and membrane protein (222 aa) as antigens to design mRNA transcripts. We produce hybrid mRNAs with C-terminal signal peptides derived human PDGFR receptor as coding sequences for all four antigens by in vitro transcription. We use A549 lung cancer cells to evaluate in vitro expression. The cells transfected independently using 0.5 µg/well of mRNA in 12-well culture plates for each antigen using PolyGION-CD-CS hybrid polymer NPs, are analyzed for viral antigens display on cell surfaces using immunostaining and mouse monoclonal antibodies produced against the full-length proteins of all four antigens. We also analyze cell lysates using western blot. Further, we use 100 ng of mRNA synthesized against FLuc reporter gene in co-transfection experiments to evaluate the transfection efficiency by BLI. The cells are longitudinally monitored for three passages after transfection to check the length of expression, which provides information for subsequent in vivo experiments, where the transfections are repeated to express antigens at sufficient levels that induce host immune responses.

Evaluation of the Functional Efficiency of SARS-CoV-2 Antigens Expressed by this New mRNA Vaccine in Binding to Respective Antibodies Using an ELISA Assay.

As well as evaluating the cell surface display, and the stability and quantity of protein expression, we evaluate the extent of these properties for all four SARS-CoV-2 antigens. Using an ELISA assay we characterize the antigens for these properties.

Experimental Methods

We use a transfection protocol similar to that adopted for evaluation of antigen expression and surface display of mRNA in A549 lung cancer cells. We quantify the cell lysates isolated 48 h post-transfection for total protein concentration and use equal amounts of whole cell lysates for ELISA assays. We use 10 μg/ml antibody concentration to coat the Maxisorb ELISA plate by diluting the antibody in 100 mM sodium bicarbonate buffer solution by incubating at 37° C. for 4-6 h. The plate is blocked using Miltenyi blocking buffer for 1 h before capturing the cell lysate containing SARS-CoV-2 antigens. We use anti-PDGFR antibody raised against the C-terminal tag as a sandwiched secondary antibody with HRP as a second antibody for detection. We follow the standard protocol for ELISA assay.

Discussion

The four antigens transfected using mRNA vaccines in lung cells are evaluated by immunohistochemistry and western blot analysis. Since we use human PDGFR transmembrane signal peptide as a C-terminal fusion with each of the viral antigens, the antigens are expected to displayed on the membrane of the transfected cells. The continuous evaluation of cells after a single transfection is expected to validate the longevity of cellular expression. Further, the use of PolyGION-CD-CS for transfection provides confidence in its in vivo applications for evaluation of immunization from IN-delivered mRNA vaccines. The use of FLuc mRNA co-transfection based BLI is expected to provide additional quantitative information on transfection efficiency. By completing these experiments, we identify the optimal concentration of each of the four mRNAs needed to achieve near equivalent levels of expression of different surface antigens for the in vivo studies proposed herein.

Example 4: Evaluation of IN Delivery of mRNA Vaccines of Surface Antigens (S, N, E and M) of SARS-CoV-2 Using PolyGION-CD-CS Hybrid Polymer NPs and Immune Response In Vivo in BALB/c Immunocompetent Mice PolyGIONs coated with CD-CS hybrid polymer showed effective loading of nucleic acids. We have previously shown that this strategy effectively IN delivers therapeutic miRNAs to GBMs in mouse models.[21] The delivery of therapeutic nucleic acids via the IN route can be controlled by regulating the breathing rate of the animals at the time of delivery. NPs delivered to animals breathing normally (without anesthesia) result in a predominant portion of NPs entering the trachea and reaching the lungs. Since Poly-GION-CD-CS possess a strong propensity towards transfecting cells, the coated mRNAs would be expected to enter into lung cells. Upon displaying SARS-CoV-2 antigens on lung cells, recruitment of immune cells would takes place to result in activation of pulmonary immune responses, and the production of innate and cell mediated immunity. Also, long-term memory cells could maintain protective immunity against the virus.

We evaluate the immunization against IN-delivered mRNA vaccines of all four surface antigens of SARS-CoV-2 in BALB/c parental strain, and transgenic BALB/c mice engineered to express human ACE2 receptor, since this receptor is important for viral entry into cells during infection, disease development, and progression.

Evaluation of IN Delivery of mRNA Vaccines of SARS-CoV-2 Using PolyGION-CD-CS Hybrid Polymer NPs and Immune Response In Vivo in Immunocompetent BALB/c Mice.

For IN delivery in vivo, we use the optimal concentration of all four mRNAs identified for the near equal levels of expression. We deliver PolyGION-CD-CS-SARS-CoV-2-mRNAs to active mice without anesthesia. We apply 5 μl NP-mRNA complex within each nostril by holding the mouse in a supine position at a 700 angle to facilitate IN application. We administer 20 μl volume of NP-mRNA complex at each application. Each 20 μl complex contains 500 ng of each mRNA+PolyGION-CD-CS containing 58.9 μg of CD-CS and $2.0 \times 10^9$ GION NPs). We also supplement 500 ng of FLuc-mRNA to facilitate BLI, to evaluate the efficiency of in vivo transfection and location of transfection. To track the PolyGIONs' distribution, we perform whole body microCT and MR imaging. We detect any possible trafficking of NPs to the brain as we focus on the lungs to observe the intended mRNA delivery.

After completing the initial imaging evaluation of delivery, we study the immune response in three mouse groups: G1: Control without any treatment; G2: PolyGION-CD-CS-Scrambled-RNA; and G3: PolyGION-CD-CS-SARS-CoV-2-mRNAs. We treat the animals every day for four IN doses (based on preliminary results) before collecting blood samples for immune evaluation. We collect 200 μl of blood every week using a submandibular blood collection method. We separate serum from blood and use an ELISA assay for antibody titration against each of the viral antigens used for immunization. We follow the same protocol as previously described herein. We also deliver additional booster doses as needed based on our initial results. The animals delivered with scRNA coated PolyGION-CD-CS and those not treated serve as controls. Once we reach the highest blood levels of antibody titers against all four antigens (a maximum of three booster doses in one-month intervals), we stop booster doses and monitor the antibody titers in the mice for the next six months by bi-weekly assessments. We have a separate group of animals where we will test immune cell subtypes to understand the changes in activated T and B cell types one week after delivering the last booster. We perform a similar evaluation in mice after six months. This allows us to assess both antibody levels and immune cell distributions in the animals for long-term immunoprotective effects. We also perform ex vivo histology of various tissues (kidneys, lungs, liver, spleen, pancreas, and brain) to evaluate for any antigen and NP delivery associated pathological effects.

Evaluation of IN Delivery of mRNA Vaccines of SARS-CoV-2 Using PolyGION-CD-CS Hybrid Polymer NPs and their Immune Response and Pathogenicity In Vivo in Transgenic BALB/c Mice Expressing Human ACE2 Receptor.

Experimental Methods

We follow the same strategy as described for the IN delivery of mRNA vaccines while using the BALB/c transgenic mice expressing human ACE2 receptor. We breed male and female homozygous TgBALB/c (K18-ACE2) 2Prlmn mice from the Jackson Laboratory to obtain homozygous offspring mice. Since the expressed antigens, especially spike protein antigen, can show differential response in these animals owing to their strong binding affinities to ACE2 receptor, we carefully monitor the animals for any pathological effects and adjust the treatment schedule as needed based on health conditions of mice.

Discussion

The evaluation of SARS-CoV-2 neutralizing antibody in the serum of BALB/c and BALB/c-hACE2 transgenic animals receiving mRNA vaccine is expected to show similar effects, but we anticipate observing severe pathological effects with poor survival rates in BALB/c-hACE2 compared to BALB/c animals under similar conditions. We expect long-lasting circulating antibodies along with B and T cell responses that are much higher in transgenic animals compared to the parental BALB/c strain.

Example 5: Gold-Nanostar-Chitosan Mediated Delivery of a SARS-CoV-2 DNA Vaccine for Respiratory Mucosal Immunization The COVID-19 pandemic is caused by the coronavirus SARS-CoV-2 (SC2). A variety of anti-SC2 vaccines have been approved for human applications, including those using messenger RNA (mRNA), adenoviruses expressing SC2 spike (S) protein, and inactivated virus. The protective periods of immunization afforded by these intramuscularly administered vaccines are currently unknown. An alternative self-administrable vaccine capable of mounting long-lasting immunity via sterilizing neutralizing antibodies would be hugely advantageous in tackling emerging mutant SC2 variants. This could also diminish the possibility of vaccinated individuals acting as passive carriers of COVID-19. Here, we investigate the potential of a novel intranasal (IN)-delivered DNA vaccine encoding the S protein of SC2 in BALB/c and C57BL/6J immunocompetent mouse models. The immune response to IN delivery of this SC2-spike DNA vaccine transported on a modified gold-chitosan nanocarrier shows a strong and consistent surge in antibodies (IgG, IgA and IgM), and effective neutralization of pseudoviruses expressing S proteins of different SC2 variants (Wuhan, South African, and D614G). Immunophenotyping and histological analyses reveal chronological events involved in the recognition of SC2 S antigen by resident dendritic cells and alveolar macrophages, which prime the draining lymph nodes and spleen for full-blown SC2-specific cellular and humoral immune responses. The attainable high levels of anti-SC2 IgA in lung mucosa and tissue-resident memory T cells can efficiently inhibit SC2 and its variants at the site of entry, and also provide long-lasting immunity.

Introduction

The coronavirus disease 2019 (COVID-19) pandemic has affected billions of people around the world. The causative pathogen, the severe acute respiratory syndrome coronavirus 2 (SARS-CoV-2, or SC2), belongs to a family of beta coronaviruses.[1] Coronaviruses are enveloped, single-stranded positive-sense RNA viruses that infect humans and mammals. Since this virus is aggressive and spreads uncontrollably, a rapid, high-priority approach has been adopted during vaccine development and approval under emergency use authorization.[2] There are several strategies currently considered for SC2 vaccine development, including mRNA, DNA, inactivated virus, adenovirus expressing SC2 spike (S) protein, and peptide vaccine varieties.[3] Most vaccines are currently targeted against the S protein of SC2 as the primary antigen, such as mRNA-1273 by Modema, or mRNA-BNT162b2 by Pfizer.[4] Inactivated virus (Covaxin) and adenovirus expressing SC2 S protein (Covishield and Sputnik) vaccines are also administered in humans.

mRNA vaccines are developed from synthetic in vitro transcribed RNA sequences coding for viral protein, but the variations between vaccines are based on the stability of these synthetic mRNAs and that of their nanoformulation vehicles.[5] Although intramuscular (IM) vaccination induces systemic humoral and cell-mediated immune responses that protect the lungs against infection and pathology, it does not confer sterilizing immunity. Moreover, inadvertent injection of a vaccine into the subcutaneous fat layer with poor vascularity can result in slow mobilization and processing of antigen leading to vaccine failure. Hence, whether adequate long-lasting active immunity develops or not after IM vaccination is still unknown.[6,7] An optimal vaccination strategy would aim for sterilizing vaccines to result in long-lasting immunity. An advantage of both DNA and mRNA constructs coding for antigens is that they are simpler and faster to produce than developing inactivated viruses or making recombinant proteins, and the risks of working with live virus/pathogen can be avoided.[8]

In contrast to IM injection, intranasal delivery (IN) of vaccine is preferred for respiratory infections to achieve both humoral and innate immune responses, while also producing sterilizing immunity in the respiratory tract and lungs. However, IN delivery requires a nanocarrier that can transport the loaded nucleic acid vaccine across the nasal cavity and down into lungs. An efficient nanoparticle (NP) delivery system is also key to mount an effective DNA/RNA vaccine immune response. Any ideal delivery system needs to demonstrate a combination of high loading capacity, stability, and biocompatibility. In that respect, apart from liposomes, a cationic polysaccharide and natural biopolymer, such as chitosan, has been used as an adjuvant in vaccine delivery systems.[9] Chitosan is a nontoxic, bioadhesive, biodegradable, and biocompatible polymer that can penetrate across mucosal surfaces of epithelial cells and their tight intercellular junctions for vaccine delivery.[10, 11] While chitosan provides effective loading and delivery of nucleic acids across cell membranes as well as an effective transfection into lungs, it requires coating onto the surface of a biocompatible solid nanocarrier to provide mobilization across the nasal cavity into lungs. Here, we develop and evaluate a gold-nanostar-chitosan (AuNS-chitosan) nanoformulation for IN delivery of a DNA vector expressing S protein of SC2, plus mRNA coding for Firefly luciferase reporter protein.

Recent studies have shown that in the absence of mucosal immunity, the nasal cavity may become a reservoir for SC2, placing patients at risk for reinfection or disease transmission to others.[13] IN vaccination can overcome this drawback as it can serve to stimulate broad immune responses via neutralizing IgG, mucosal IgA, and T cells, which can instigate a local mucosal immunity in the nasal cavity critical for blocking both infection and spread from this reservoir. The lungs share many features with other mucosal sites, but preservation of its delicate histomorphological integrity requires a fine interplay between pro- and anti-inflammatory responses in the face of external insults. Well-timed, appropriately located, and tightly regulated T and B cell responses are essential to protect from infection, whereas poorly regulated inflammation contributes to tissue damage and disease development.[14] There are many other advantages to IN delivery, including the avoidance of injections, and likely high tolerance and compliance in use by humans. Furthermore, respiratory tract immunization via the IN route can target a large surface area for immune response induction, including the establishment of abundant antigen presenting cells. IN vaccination triggers upper and lower respiratory tract mucosal and sub-mucosal surfaces for protective humoral and cellular pathogen-specific immune responses that also remain at high levels at the port of entry for these pathogens.

Alveolar macrophages (AMs), dendritic cells (DCs), epithelial M cells, intraepithelial lymphocytes, as well as lymph nodes and lymphoid tissues of the upper respiratory tract and the bronchial tree all help in mediating a strong immune response to vaccines.[16] Tissue resident and circulatory leukocyte migration through the lungs plays a vital role in IN vaccination. To track this dynamic interaction, we evaluate this vaccination approach in C57BL/6J transgenic mice with $Ccr2^{RFP}Cx3cr1^{GFP}$ dual-reporter (C57BL/6J-DR), as well as BALB/c mice. The CX3CR1+ receptor is predominantly expressed in leukocytes such as CD8+, CD4+, and $\gamma\delta$ T lymphocytes, as well as natural killer (NK) cells, DCs, and monocytes/macrophages. On the other hand, engineered CCR2-RFP enables the tracking of resident monocytes and AMs.[17]

Antigens formulated onto/into NPs can reach the respiratory mucosa in the airways and lungs for uptake by relevant immune cells.[18] With growing concerns over IN administration of live-attenuated viral vaccines, NP-based carriers are a promising alternative to generate safer mucosal immunity. We thus investigate in mice the potential of AuNS-chitosan for IN delivery of a SC2 vaccine delivered to the upper and lower respiratory tract mucosa. Gold NPs have recently been used as antigen carriers and immune cell activators for vaccination.[19] These NPs are non-toxic and have been used in various applications.[20] Gold NPs formulated for IN administration have been shown to diffuse into lymph nodes to trigger robust antigen-specific cytotoxic T cell immune responses.[21] With this in mind, we test DNA (expressing the S protein of SC2) vaccine-mediated antibody production using AuNS-chitosan as a carrier for IN delivery in mice. Additionally, we test the feasibility of IN delivery of AuNS-chitosan carrying mRNA coding for luciferase reporters to target the respiratory airways and as a proof-of-concept and model platform for future adaptation of our strategy to delivery of a SC2 mRNA vaccine. The eventual clinical translation of this approach should be a seamless extension of current mRNA vaccines.

Avoidance of using pathogen particles confers a distinct advantage to current mRNA vaccines, as they are non-infectious in nature. An mRNA strand is rapidly degraded once the protein is made. Unlike pDNA, which relies on cell and nuclear membrane poration to reach the nucleus for transcription and further translation into proteins, it is sufficient for an mRNA strand to gain access to the cytosol for translation. Some of the early clinical trial results indicate that an RNA vaccine can generate a reliable immune response and is well tolerated by healthy individuals, with negligible side effects. On the other hand, DNA is a more stable molecule than mRNA, and use of DNA may yield a robust vaccine with a longer shelf life suitable for worldwide distribution. However, DNA expression cassettes carry the theoretical risks of genome integration, insertional mutagenesis, long-term expression, and the induction of anti-DNA antibodies. Given the many pros and cons of these two nucleic acid vaccines, we here initially develop and pre-clinically evaluate an IN administered anti-SC2 DNA vaccine using our AuNS-chitosan delivery vehicle. Conceptually, we aim to establish proof-of-principle for our IN delivery platform using this DNA vaccine by firstly validating its stability and successful organ specific expression (using in vivo imaging of simultaneously delivered luciferase reporter mRNA), and to establish the presence of an ensuing robust vaccine-mediated immune effect in mice. We extend this same strategy to create and evaluate a similar IN administered anti-SC2 mRNA vaccine, and will conduct comparative studies of these two nanotechnologies prior to clinical translation. However, a critical pre-requisite applicable to both proposed vaccines is whether sufficient SC2 nucleic acids can be transferred across cell membranes using our AuNS-chitosan NPs. Since electroporation is normally required for DNA uptake across cell and nuclear membranes, we reasoned that initial testing of an anti-SC2 DNA vaccine would be useful to establish the ability of this NP vehicle to replace electroporation. Moreover, if AuNS-chitosan alone can robustly deliver sufficient DNA into the cytosol and then nucleus for subsequent S protein expression, it would suggest that a similar future strategy using mRNA alone, which requires gaining access only to the cytosol for S protein translation, would most likely succeed.

It is well established that S protein mediates viral transduction via interaction with angiotensin-converting enzyme 2 (ACE2) receptors followed by endocytosis. Thus, vaccines based on the S protein could induce antibodies to block virus binding and fusion with respiratory airway columnar ciliated cells (and their progenitor cells) expressing ACE2 receptors, or neutralize the virus infection.[22] Moreover, compared to all structural proteins of SC2, the S protein appears to be the main immunogenic protein to induce both cellular and humoral immunity against virus infection.

As compared to the short half-life of injected protein antigens, DNA vaccines can provide tissue specific expressions of antigens over much longer periods, thereby better priming the immune system.[23] We therefore designed AuNS-chitosan to IN deliver a SC2 DNA vaccine to stimulate a broad immune response, including both systemic (neutralizing IgG) and local immunity (mucosal IgA, and T cells) in the nasal cavity and respiratory tract. We find that this IN-vaccination strategy also achieves prominent levels of anti-SC2 IgA in the lung mucosa and tissue-resident memory (TRM) T cells that efficiently neutralize SC2 pseudovirus and its variants, thus providing long-lasting immunity.

Results and Discussion

In vitro characterization of gold nanostar synthesis, physicochemical properties, stability, chitosan coating, and DNA loading efficiency at different molar ratios.

Figure 9A:
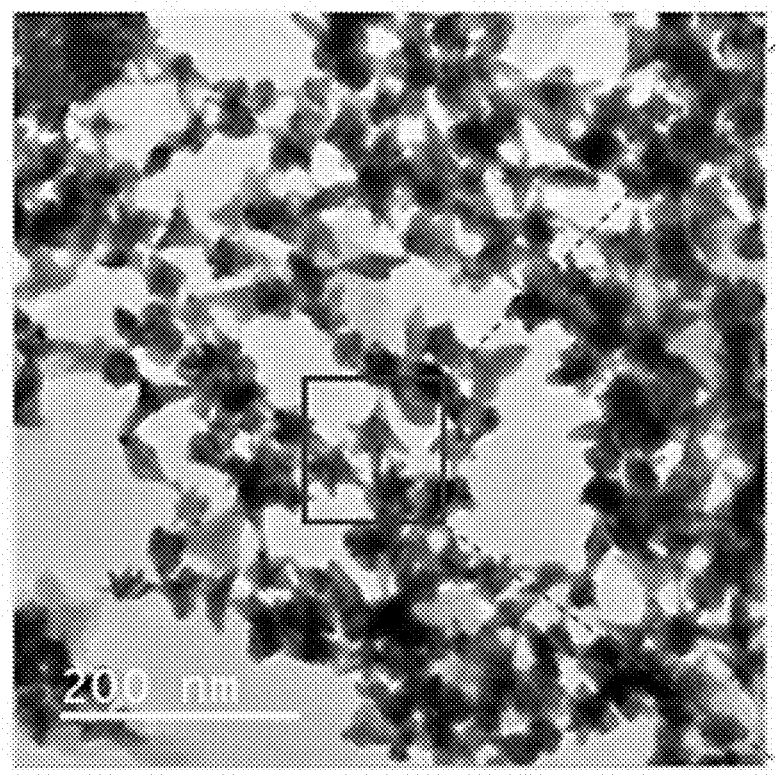
FIGS. 9A-9H show in vitro characterization of SC2 DNA vaccine loaded on AuNS—CS NPs.
Figure 9B:
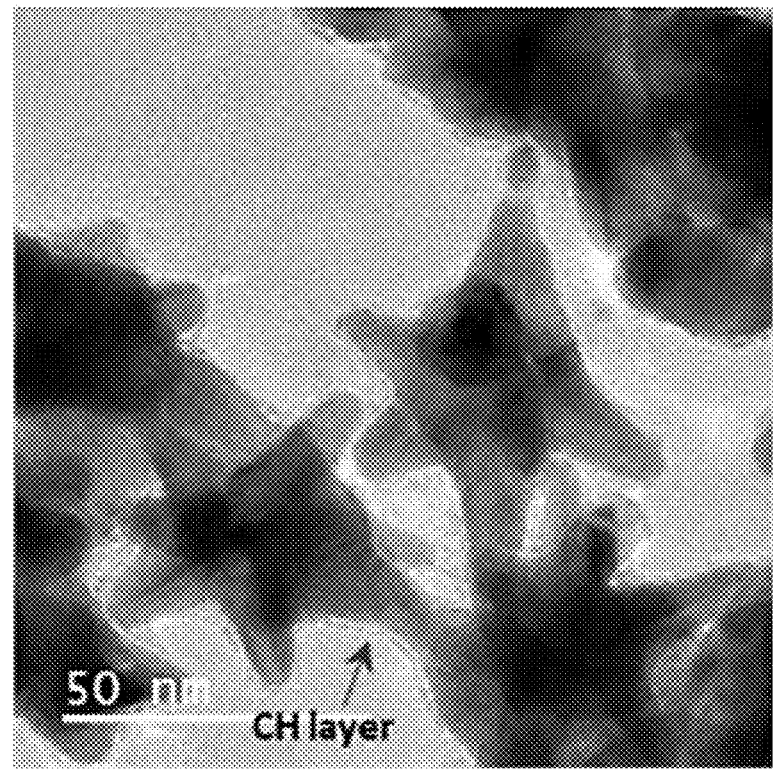
Figure 9C:
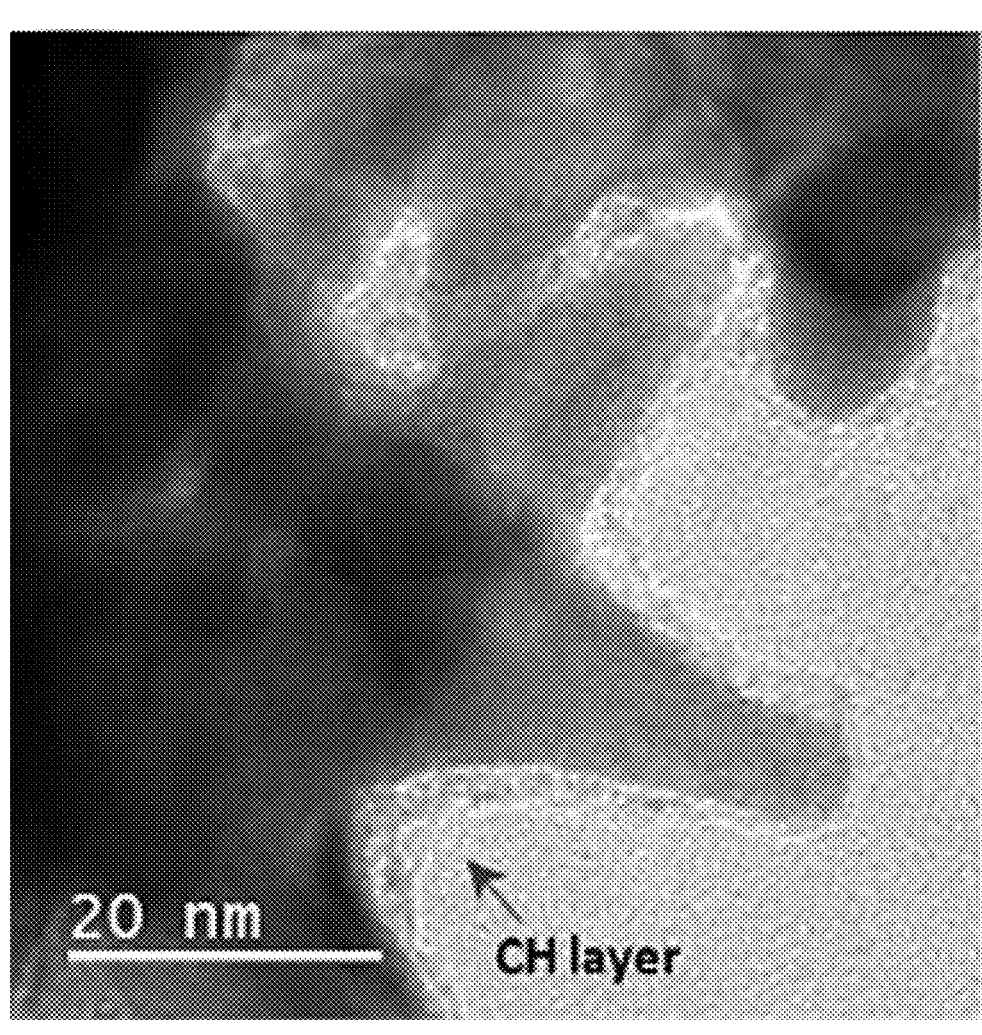
Figure 9D:
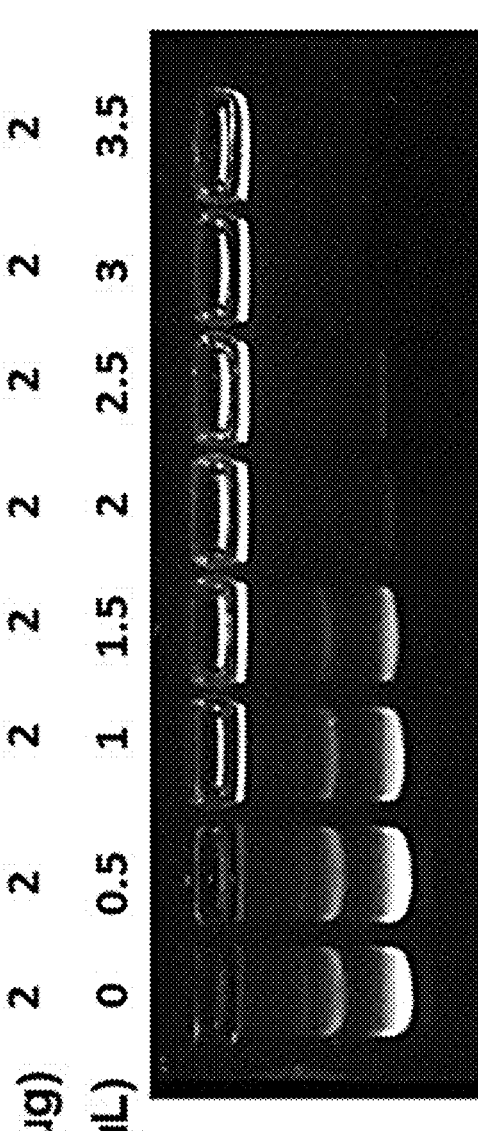
Figure 9E:
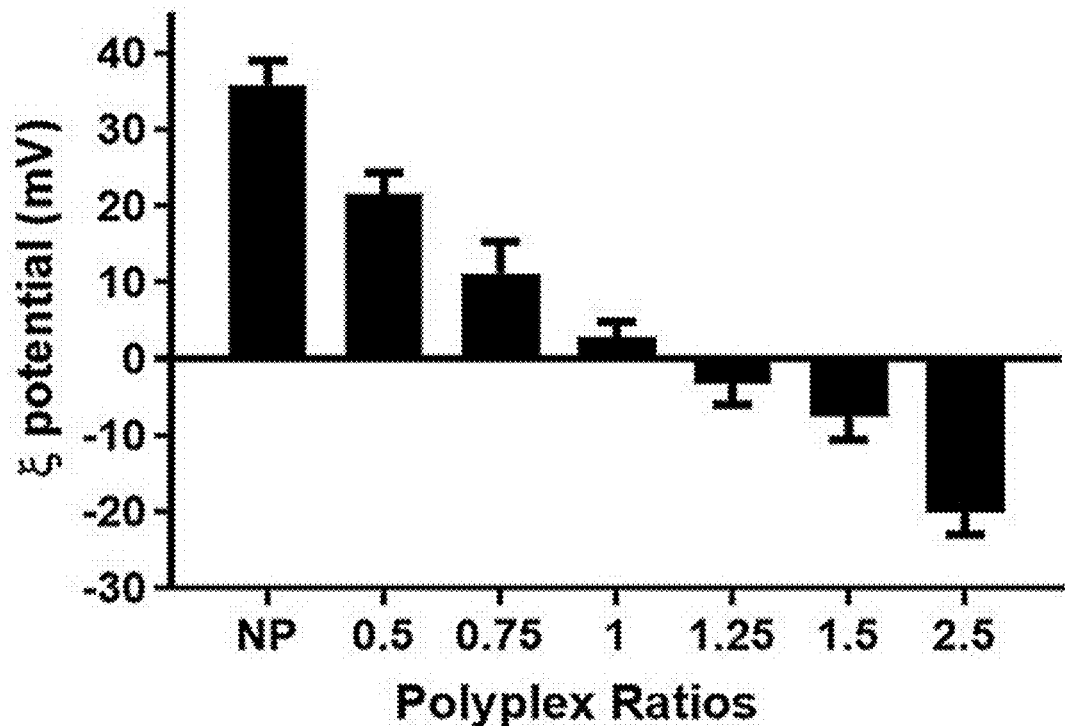
Figure 9F:
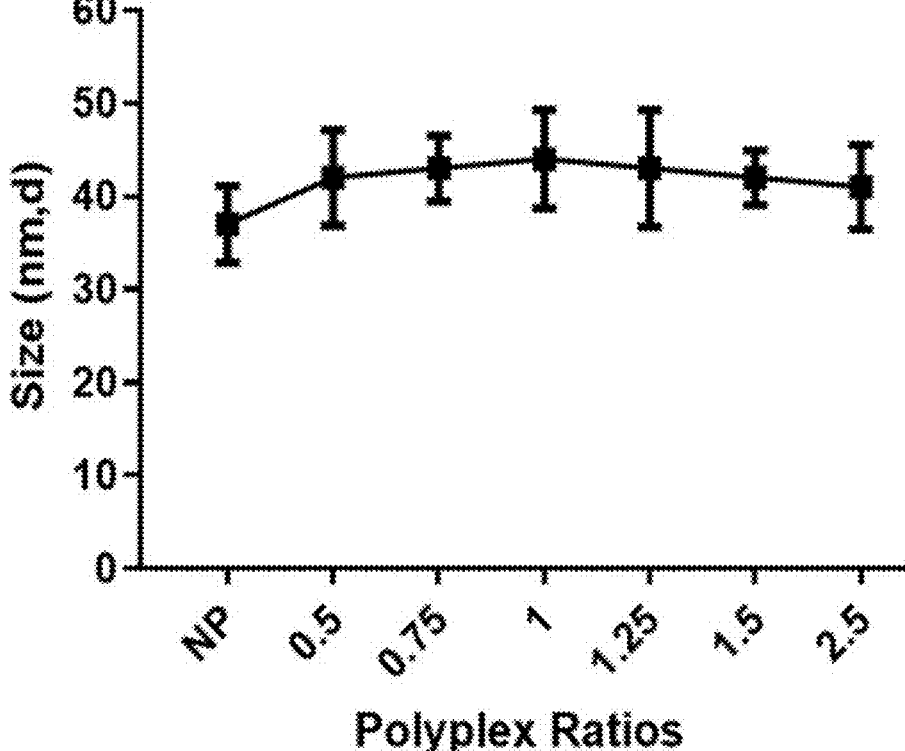
Figure 9G:
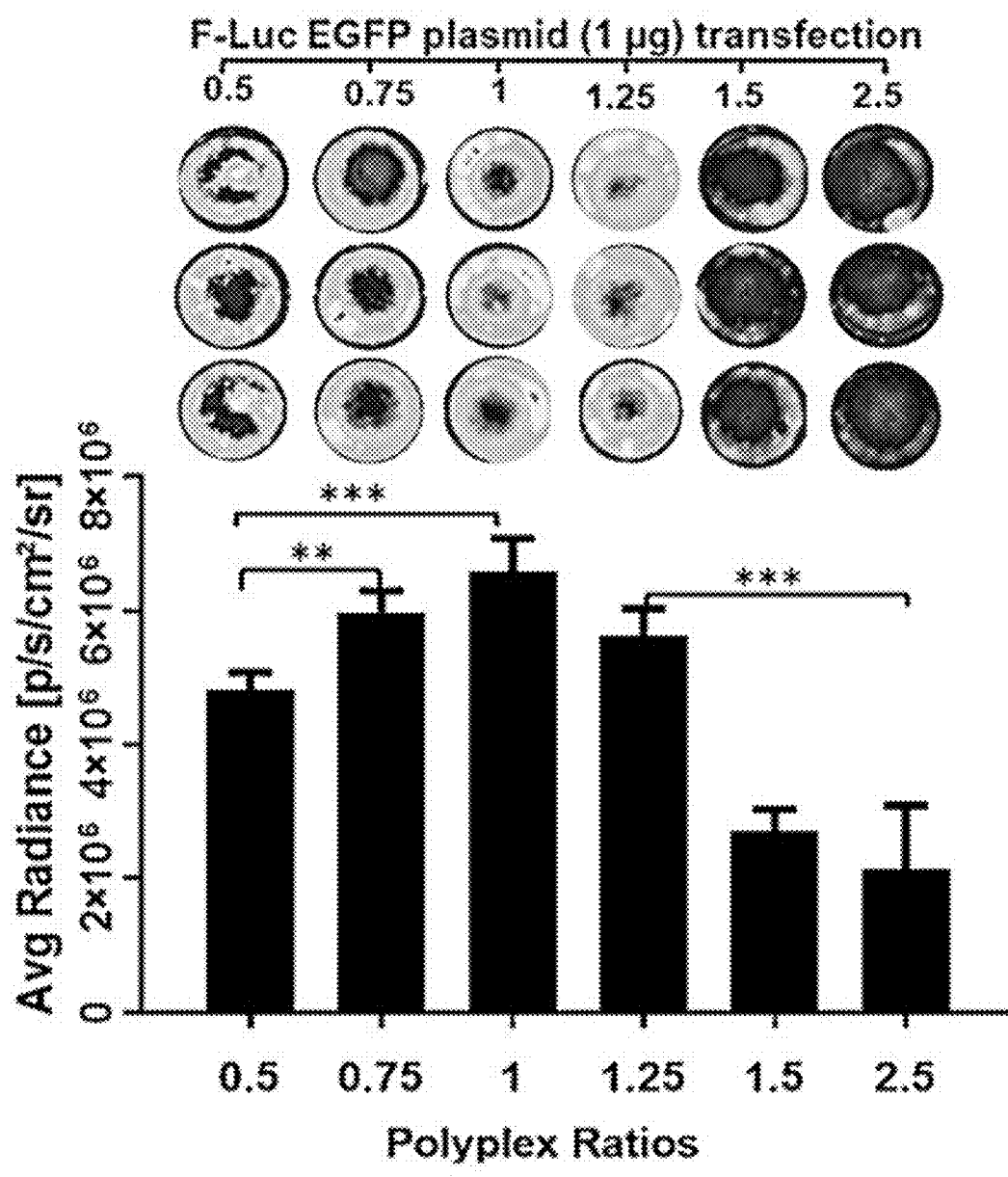
Figure 9H:
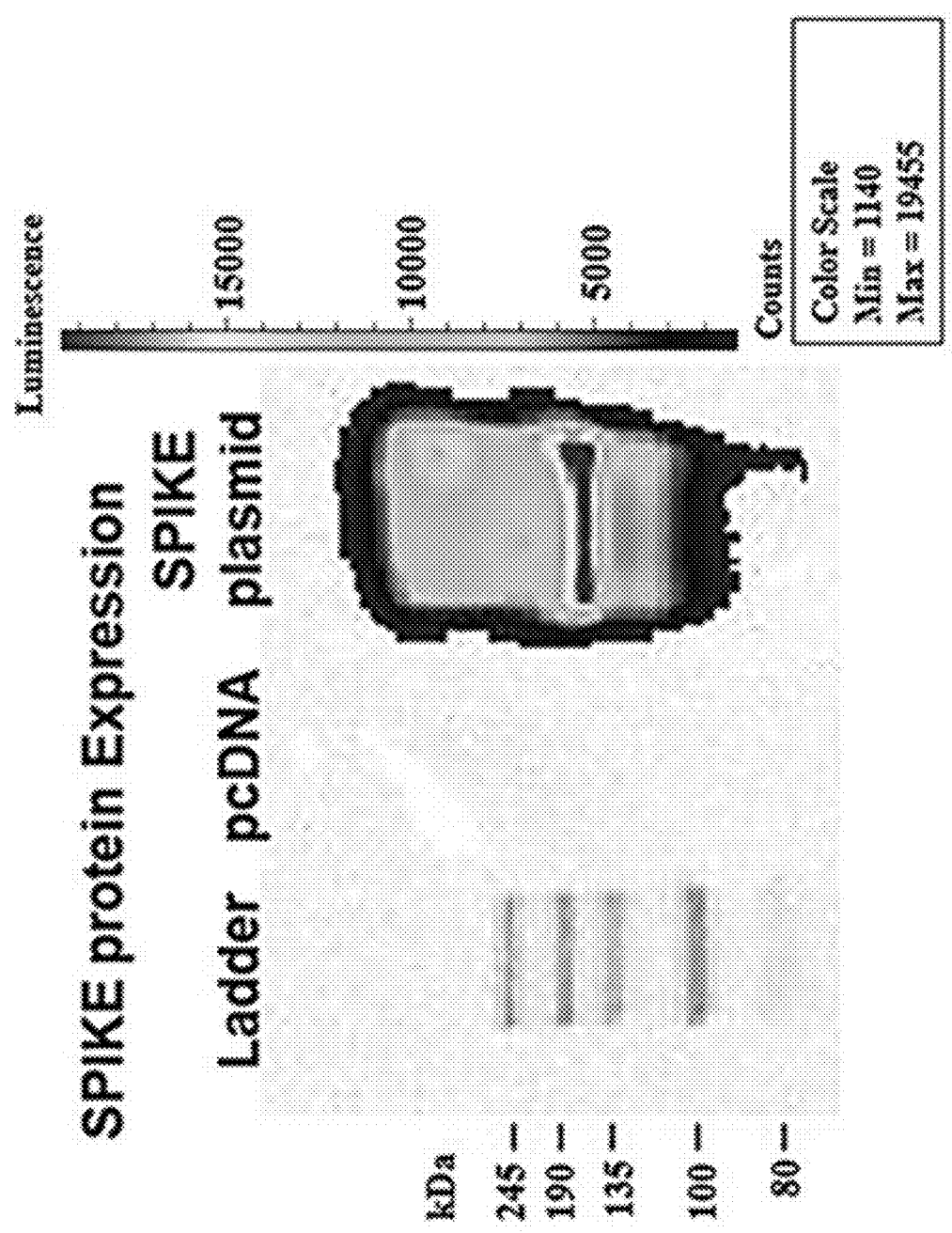

We prepared AuNS-chitosan using a modified procedure that we outlined previously.[20] which is incorporated by reference herein in its entirety and for all purposes. We optimized the reaction conditions to generate gold nano-octopods that provide ample surface area for incorporating the payload. The surfaces of as-prepared AuNSs were modified using cationic biopolymer chitosan to improve their biocompatibility, colloidal stability, and to achieve sufficient surface potential for loading anionic nucleic acids. The uniform monolayer of chitosan on the modified AuNS was evident on high resolution transmission electron micrographs (TEM), which also correlated with evident changes in NP surface potential measurements. TEM revealed a narrow size distribution of NPs, with an average size of the NP core as 20 nm and protruding spikes of ~20-30 nm (FIGS. 9A-9C). The pristine AuNS had a surface potential of ~5.6 mV (+2.89 mV) that shifted to a cationic surface potential of +35.8 mV (+3.59 mV) upon capping with cationic chitosan polymer. We estimated the pDNA (the coding sequence of SC2 S protein) loading efficiency for AuNS-chitosan using a gel retardation assay. We complexed the SC2 plasmid (2 µg) with increasing amounts of AuNS-chitosan and the resultant polyplexes demonstrated a consistent increase in encapsulated pDNA. The polyplex amount of 2.5 μL AuNS-chitosan encapsulated 2 μg of pDNA-SC2 plasmid in the NPs, resulting in pDNA being completely retained in the well during electrophoresis in the gel retardation assay (FIG. 9D). We also evaluated the polyplexes for hydrodynamic size using dynamic light scattering (DLS) and surface zeta potential measurement, which also agreed with the gel electrophoresis findings. With increasing amounts of SC2 plasmid in polyplexes with AuNS-chitosan, pDNA was increasingly trapped on the surface of NPs by electrostatic interactions, and as a result of which the zeta potential declined to a nearly net neutral surface potential of +2.12 (±3.4 mV) at a polyplex ratio of 1 μL NPs with 1 μg of SC2 plasmid, indicating the maximum loading efficiency of AuNS-chitosan. Likewise, at polyplex ratios with more than 1 μg pDNA, the surface zeta potential diminished further to a negative surface potential indicating an excess of loosely bound pDNA on the surface of NPs, which was also clearly evident in the gel retardation assay. Although each ratio of polyplexes displayed different surface potentials, the size of the pDNA loaded AuNS-chitosan was constantly in the range of 35-48 nm (FIGS. 9E-9F). In order to determine the optimum polyplex ratio for plasmid delivery, we loaded AuNS-chitosan with a pcDNA-FLuc-eGFP plasmid and evaluated it for transfection efficiency in A549 (non-small cell lung carcinoma) cells using bioluminescence imaging (BLI). In agreement with the gel retardation assay and zeta potential measurements, we observed maximum transfection efficiency with a combination of 1 μg of plasmid and 1 μL of AuNS. To evaluate S protein expression using pcDNA-SC2 plasmid (the DNA vaccine), we transfected HEK293T cells with different variants of SC2 plasmid (Wuhan, SA, and D614G) using AuNS with the optimal ratio, and the cell lysates were probed for expression of S protein using anti-rabbit SC2-spike antibodies. We also assayed the CoV-2 and CoV-1 proteins using an anti SC2 antibody to validate their implications in subsequent dot blot and ELISA immunoassays (FIG. 9H). Overall, the proposed DNA vaccine formulation comprised of three components: AuNS, chitosan polymer, and plasmid DNA.

Intranasal administration of AuNS-chitosan loaded with SC2 DNA vaccine manifests S antigen specific immune responses in transgenic C57BL/6J-DR and BALB/c mice.

Figure 10A:
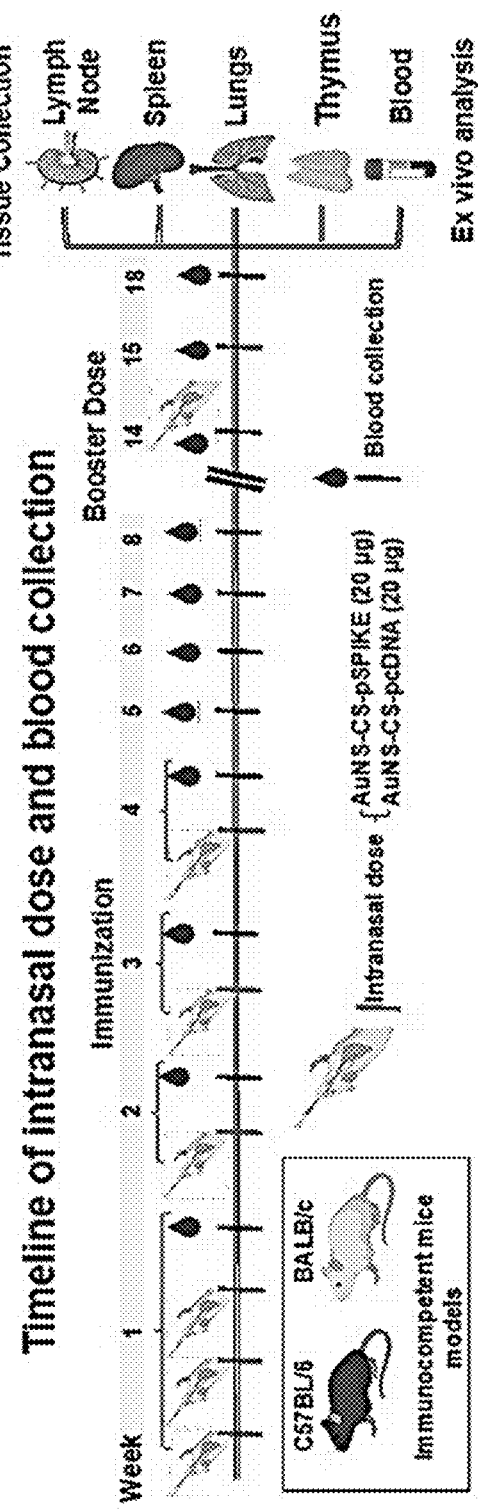
FIGS. 10A-10D illustrate (FIG. 10A) a Schematic representation of the experimental design: Five-weeks-old BALB/c mice and C57BL/6J mice were immunized with AuNS-chitosan loaded with control DNA or SC2-S DNA vaccine administered via the IN route, the serum was collected every week and assessed for anti-SC2 antibody against purified proteins of CoV-1 and CoV-2.
Figure 10B:
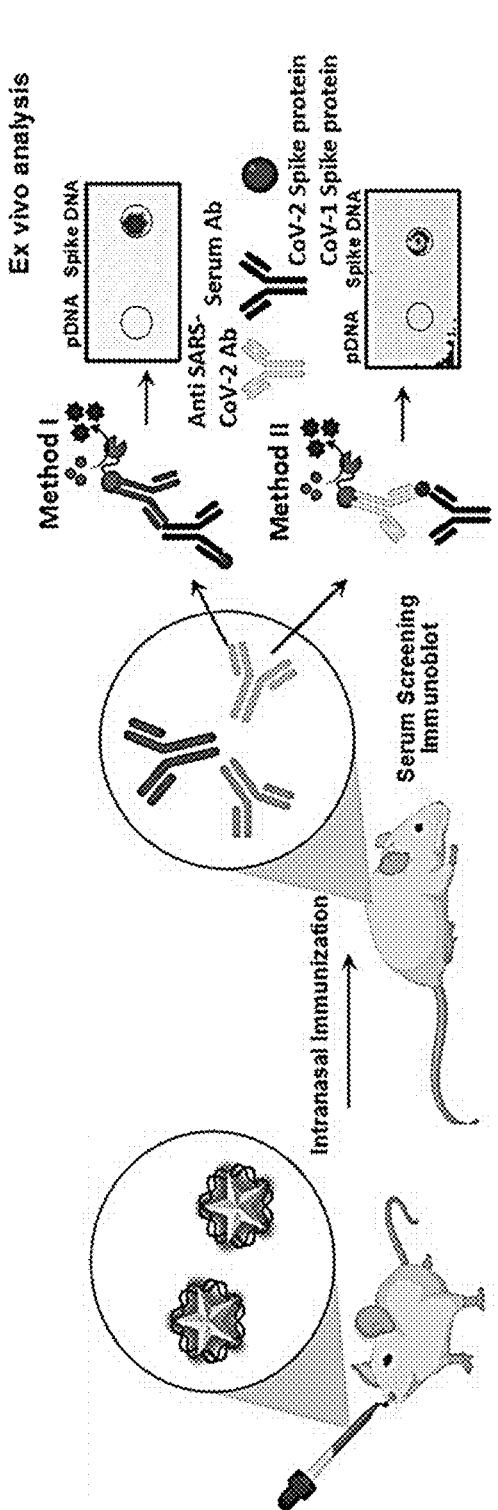

Described herein is the development and proof-of-principle of a IN DNA vaccine platform as the groundwork for an IN mRNA vaccine. It has been shown that a subunit vaccine of SC2 S protein, along with a liposomal STING agonist as an adjuvant, can induce a strong mucosal immunity upon IN delivery in a mouse model.[13] However, a subunit vaccine may not elicit neutralizing antibodies sufficient to cover protection against the wide range of variants currently spreading across the globe. Hence, we evaluated our IN-DNA vaccine against SC2 S protein, and this strategy can be extended to mRNA vaccines coding for different SC2 structural proteins (S, N, E, and M) to elicit immunity that can protect from all different variants in all viral proteins. We used BALB/c and C57BL/6J-DR transgenic mice to validate the broad immunization capabilities of this IN delivered vaccine, while the C57BL/6J-DR transgenic mice allowed more specifically for evaluation of T cell activation and trafficking using the engineered fluorescence proteins. To evaluate the efficiency of IN delivery of the SC2 DNA vaccine, we delivered pDNA expressing S protein loaded onto AuNS-chitosan via IN delivery in BALB/c and C57BL/6J-DR mice (N=10, each). Mice were given 10 μg of DNA at the intervals shown in FIGS. 10A-10B.

The reactivity of sera from SC2-vaccinated mice with the S protein of SARS-CoV-1 and SC2 determined using S protein-based dot blot assay.

Figure 10C:
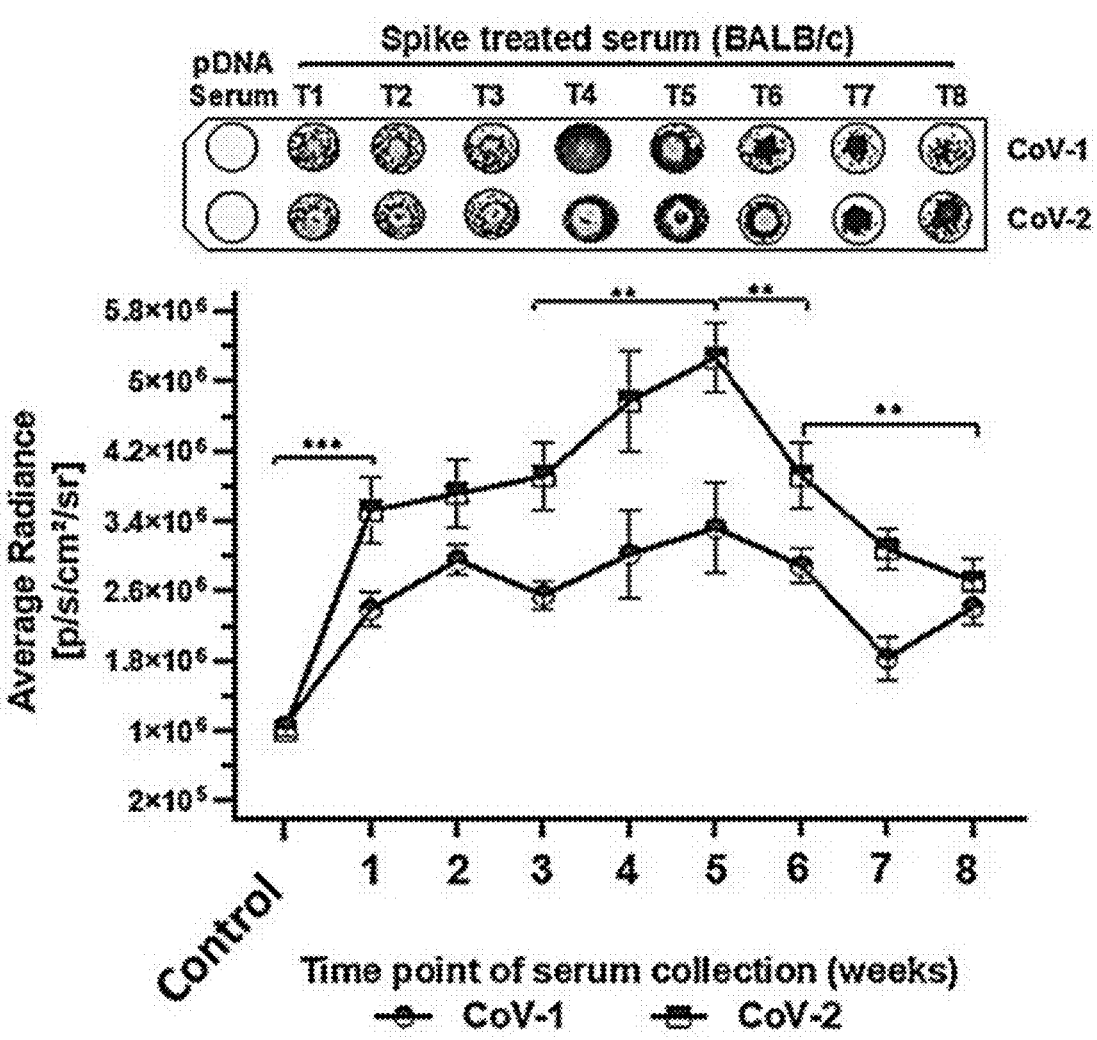
Figure 10D:
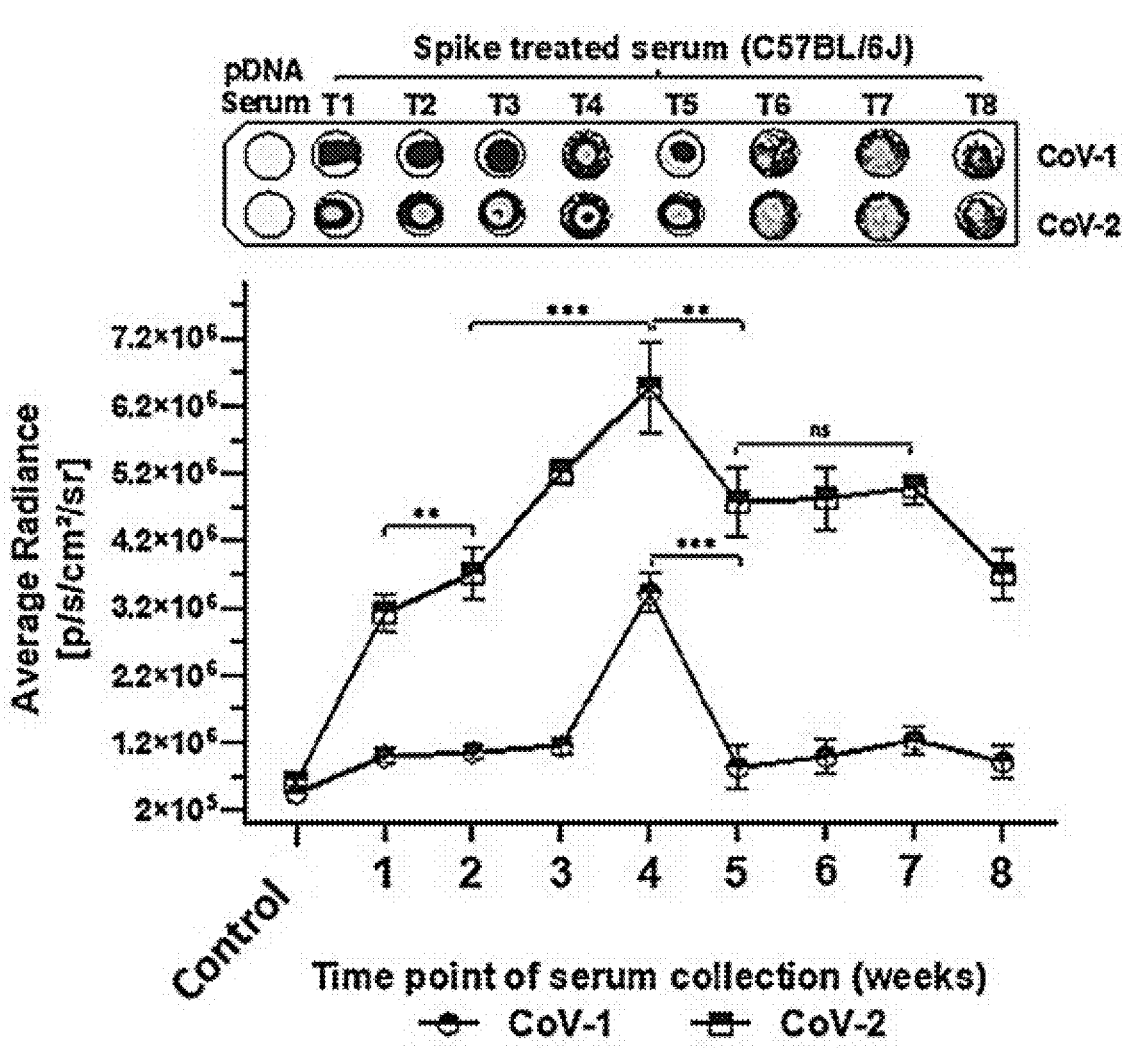

With the established evidence of anti-SC2 specific immunoglobulins generated in mice upon vaccination, we further investigated the sera cross-reactivity with the Si subunit of SARS-CoV-1 (SC1) from the 2003 SARS outbreak.[26] We tested sera collected at different time points from both control and SC2 vaccinated BALB/c and C57BL/6J-DR mice for the anti-S protein antibody against purified S protein from SC1 and SC2 using a chemiluminescence dot blot assay. We clearly observed that the antibodies to the delivered DNA vaccine were produced in as early as two weeks after vaccination (FIG. 10C). Even though the S protein of SC1 shows significant homology with that of SC2, the serum of mice induced using the SC2 vaccine showed less sensitivity to the SC1 S protein compared to SC2. Evaluation of serum collected from both BALB/c and C57BL/6J-DR mice at all time points indicated that the sensitivity of SC2 protein detection was much higher compared to SC1, and was also consistent in both mouse models (FIG. 10C). The SC1 detection signal was nearly 40-60% less effective than that of SC2 indicating significant cross reactivity, which is consistent with earlier findings that the vaccination approach outlined here can potentially provide protection against related viruses of the sarbecovirus subgenus, with similar efficiency compared with SC2.[27] The C57BL/6J-DR mice had slightly higher titers of antibody compared to BALB/c mice at all the time points studied, which may be related to variations in their genetic and immune background. Overall, the trend in serum detection levels followed the same pattern as observed in the ELISA assay, with the highest serum levels of anti-SC2 S protein antibody peaking at Weeks 4 and 5 of treatment in C57BL/6J-DR and BALB/c mice, respectively. This provided the evidence for a B cell-mediated humoral immune response triggered upon DNA vaccination (FIG. 10D). Although the trend was consistent in both mouse models, the peak antibody levels in serum of C57BL/6J-DR was ~25% higher than in BALB/c mice. The observed difference in serum antibody levels and their time to peak values were possibly owing to immunological differences in these two inbred mouse strains.[28, 29] However, the vaccination efficacy and pattern in humoral immune response was prominent in both models.

Intranasal vaccination boosts cross-variant humoral immune response against mutant variants of SC2.

Figure 11A:
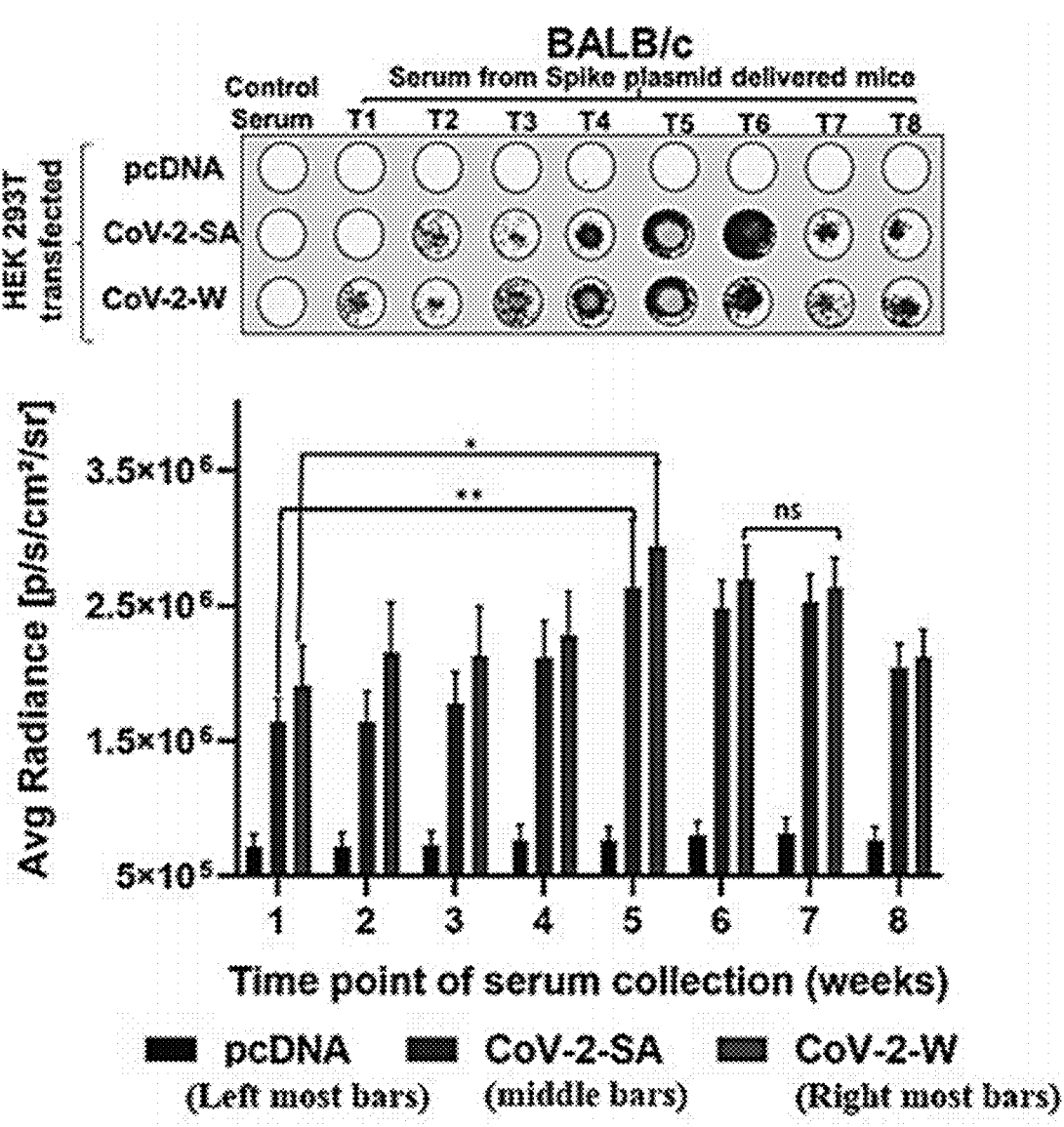
FIGS. 11A-11G illustrate dot blot immunoassay for screening anti-SC2 antibody levels in (FIG. 11A) BALB/c and (FIG. 11B) C57BL/6J mice at different time points of treatment. The serum was probed against the cell lysate of HEK-293T cells transfected with plasmid encoding S protein of SC2-SA-mutant and SC2-Wuhan variant to determine the efficacy of vaccination strategy in mounting an immune response against different variants of SC2.
Figure 11B:
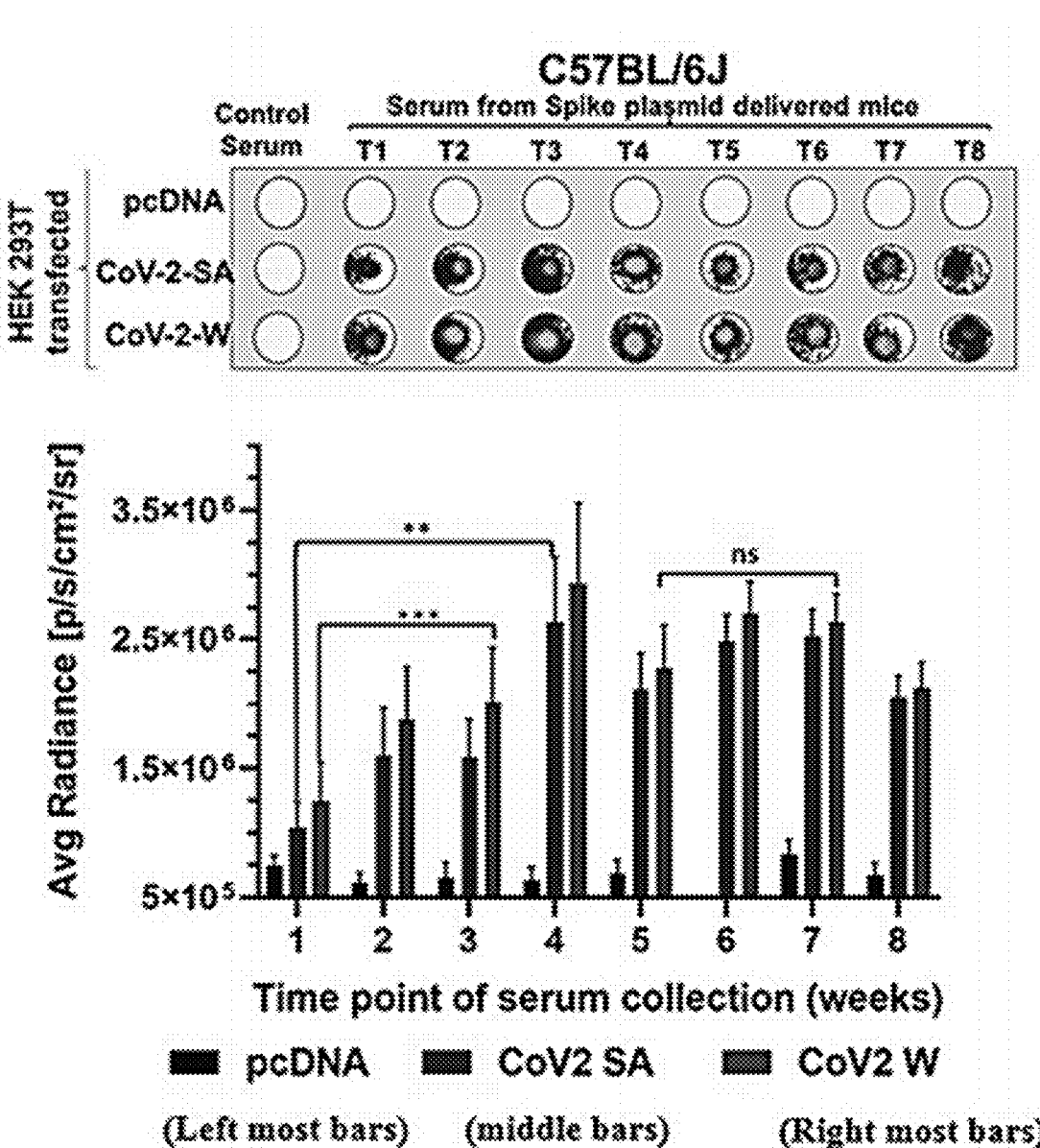
Figure 11C:
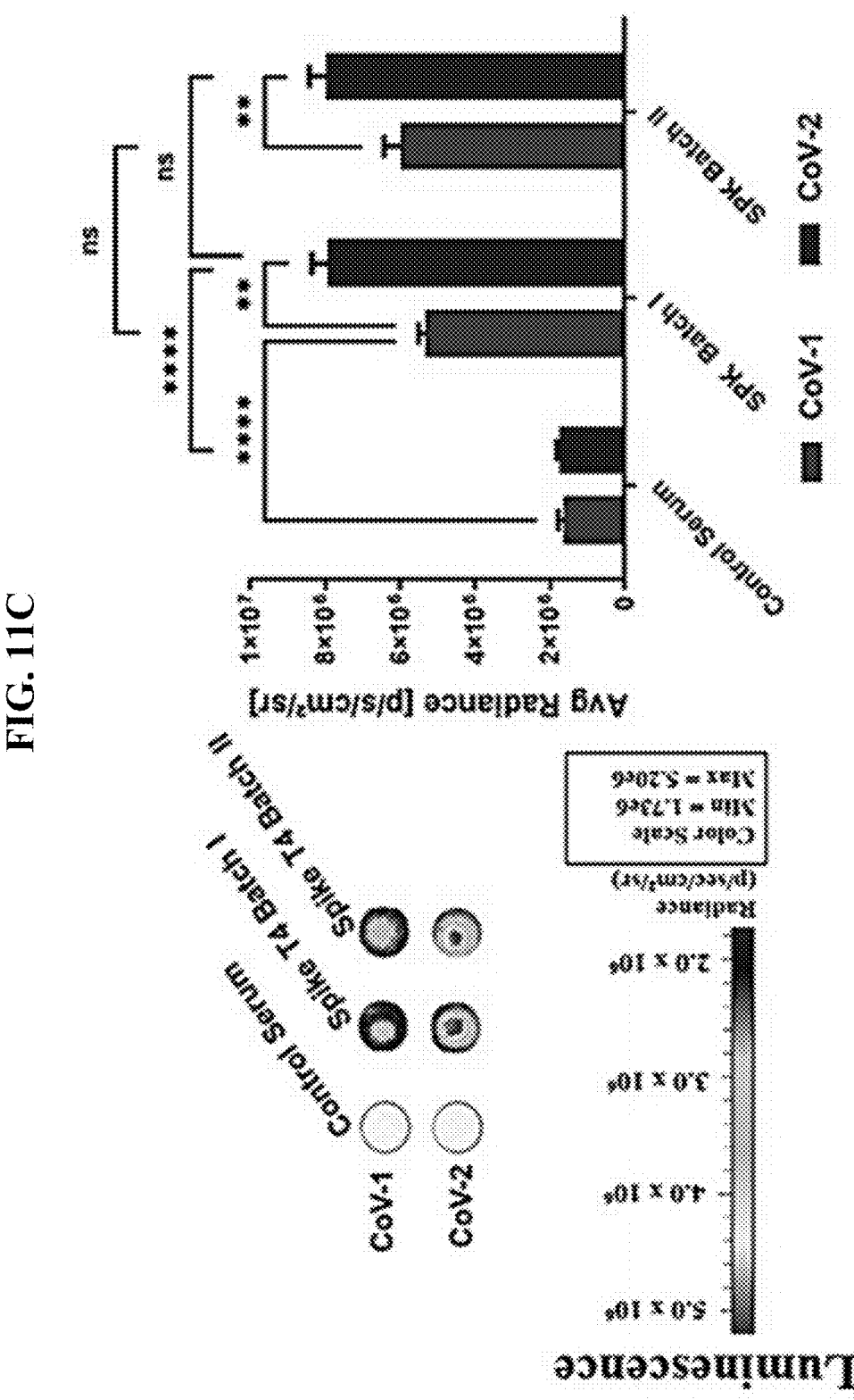

With the global surge in SC2 infections, the viral susceptibility to undergo mutations also increases with spread and time, which results in emergence of new mutant variants.[30] Emerging SC2 variants have raised concerns because of resistance to neutralizing antibodies elicited by previous infection or vaccination. Mutations found in emerging S protein variants decrease the sensitivity to neutralization by monoclonal antibodies, convalescent plasma, and sera from vaccinated individuals.[31] As a result of such growing concerns, we further evaluated whether IN SC2 (Wuhan) vaccinated mice sera could show cross-reactivity with other emerging variants of SC2. We used an immunoblot assay with total cell lysates of HEK-293T cells transfected with plasmids encoding SC2-Wuhan S protein and SC2-South Africa (SA)-mutant S protein to probe serum collected from BALB/c and C57BL/6J-DR mice for cross-variant neutralizing antibodies against SC2-SA-mutant. We found that both SC2-Wuhan and SC2-SA-mutant S proteins were equally detected by serum collected at all time points (FIGS. 11A-11B). These findings were consistent in both mouse models, and they strongly indicate the efficacy of our vaccination approach against new strains of SC2. On the other hand, these results also point out the importance and need for future vaccination of both uninfected and previously infected subjects to elicit cross-variant neutralizing antibodies when using our proposed strategy.[32] We verified the trend in serum levels of SC2 S antigen specific immune response by using different assays. Moreover, in order to establish the consistency of this vaccination approach, we compared serum levels of neutralizing antibody from two independent studies with a batch of five C57BL/6J-DR mice in each group (FIG. 11C). Comparative immunoblot analyses of serum collected four weeks after immunization were evaluated against purified SC2 and SC1 proteins, and the results indicated similar serum levels of neutralizing antibodies in both batches, supporting the reproducibility of this IN immunization approach.

Figure 11D:
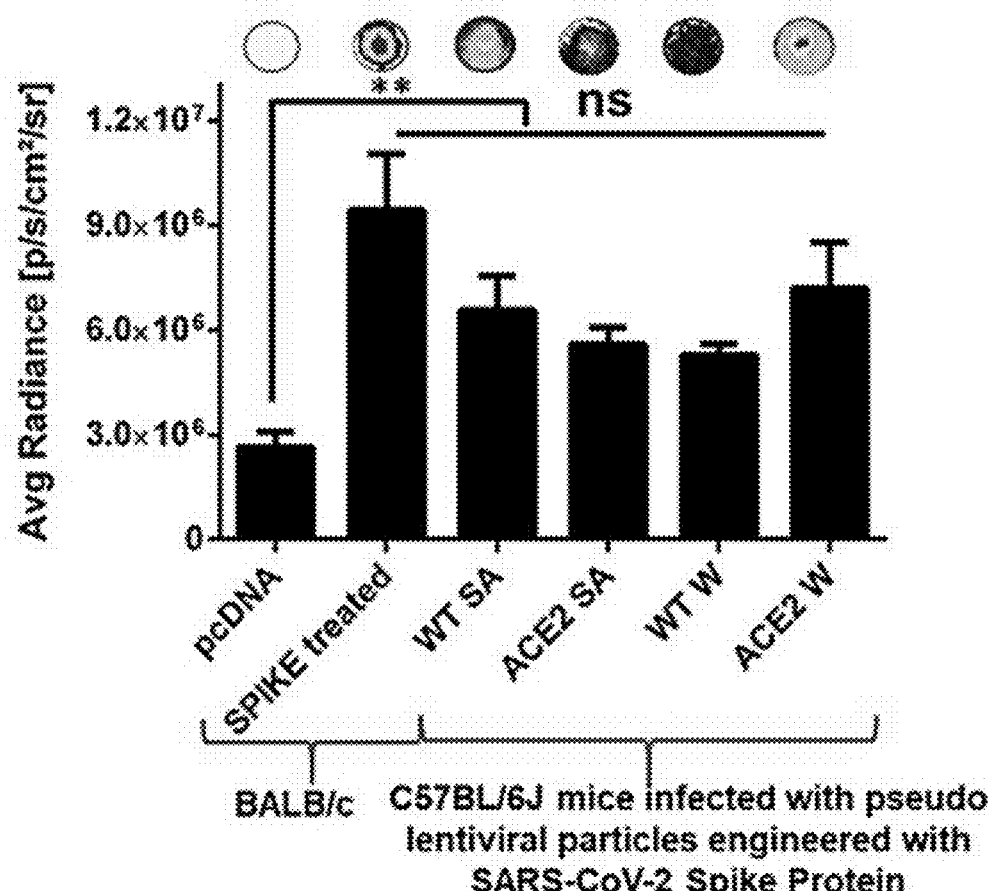

To draw comparisons between DNA vaccine-mediated immunity and actual infection-mediated immunity, we investigated immune responses of transgenic mice expressing human ACE2 receptor along with respective control strains (C57BL/6J and C57BL/6J-ACE2) to SC2 pseudovirus delivered via the IN route. We tested two different variants of pseudoviruses corresponding to SC2-Wuhan and SC2-SA-mutant in wild type and ACE2 engineered C57BL/6J mice. Evaluation of serum collected from mice five days after pseudovirus infection showed significant (p<0.01) levels of anti-SC2 antibody in both wild type and ACE2 transgenic mice (FIG. 11D). By way of comparison, the results indicate that the extent of humoral immune response generated by IN administration of our SC2 DNA vaccine loaded onto AuNS-chitosan NPs was nearly 30% higher than that achieved by pseudovirus-mediated transduction at the similar time point of the study (5 days post treatment of 3 doses of SC2 DNA vaccine or SC2-Wuhan and SC2-SA pseudoviruses).

Intranasal delivery of DNA vaccine expressing SC2 S protein using AuNS-chitosan showed effective activation of humoral pulmonary immunity.

The entry of SC2 into cells is initiated by interaction of the receptor-binding domain (RBD) of the viral S glycoprotein with ACE2, which acts as a receptor for the virus on the target cell surface.[33] Antibodies generated against SC2 S antigen can be screened using S protein-based ELISA. Mucosal immunization through the IN route can elicit local immune responses, including secretory IgA antibodies to confer protection at or near the site of initial entry of respiratory pathogens.[34] To assess the immunogenicity and protective efficacy of AuNS-chitosan loaded with SC2 S DNA vaccine, we used two different mouse strains, BALB/c and C57BL/6J-DR.

Figure 11E:
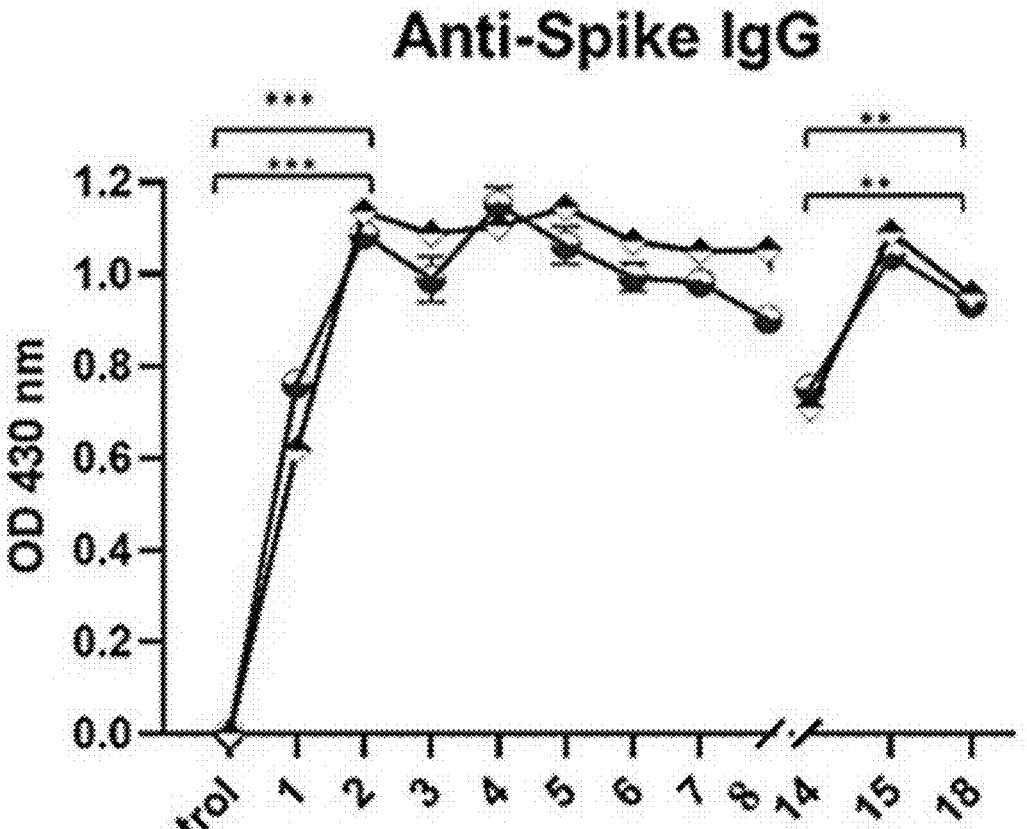
Figure 11E:
Figure 11F:
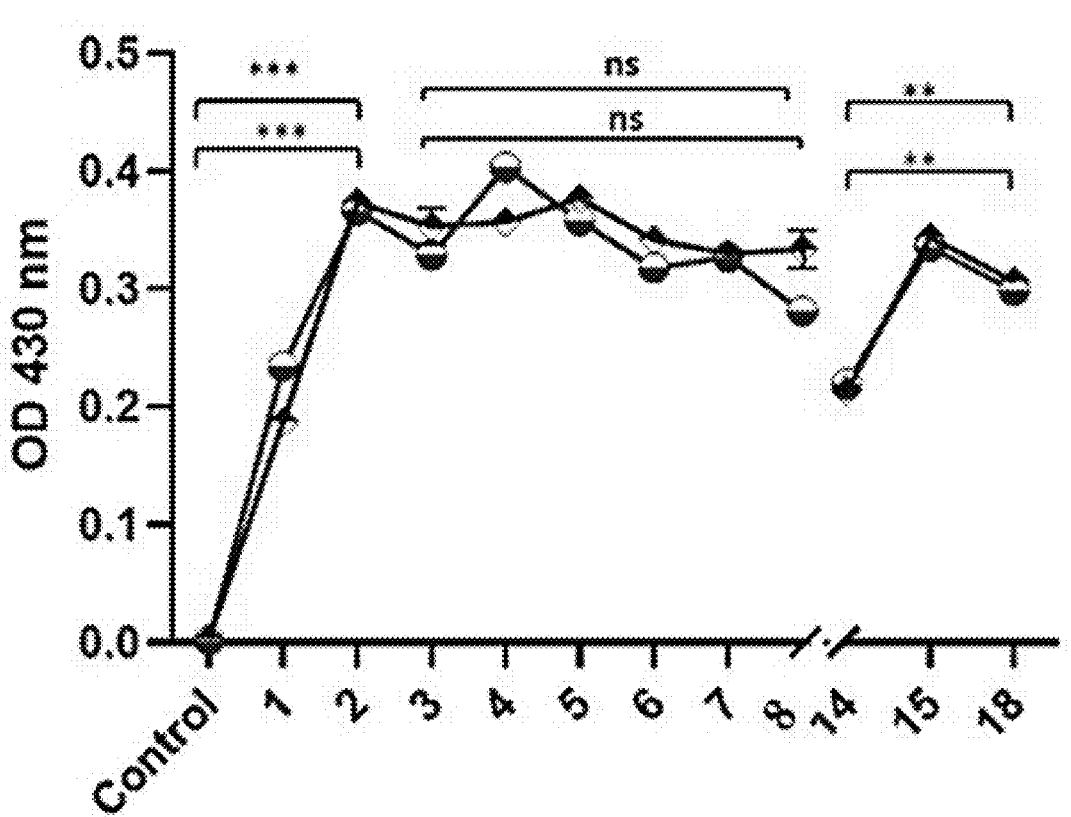

We IN administered 10 μg of SC2-DNA vaccine after encapsulation onto AuNS-chitosan at the optimized ratio. Three doses of DNA vaccine were administered to mice in the first week, followed by one dose for three consecutive weeks. We continued blood collections for eight weeks after the first dose, as shown in the schematic in FIG. 10A. We analyzed the S protein antibody responses in serum at different time points to determine SC2 S protein specific IgA, IgG and IgM titers in vaccinated mice as compared to control mice. As indicated in the ELISA results, IN immunization of AuNS-chitosan-SC2-spike, but not control DNA loaded AuNS-chitosan, induced high levels of S protein specific IgG, IgA and IgM antibodies in serum (FIG. 11A-11G). We measured vaccine induced IgG, IgA and IgM in serum serially, up to eight weeks in both BALB/c and C57BL/6J-DR mice using an ELISA assay. S antigen-specific IgG levels rose exponentially in both mice strains as early as in the first week (after three doses) and remained at the peak for eight weeks, independent of further doses of vaccination (FIG. 11E). The animals were maintained for 14 weeks without any further doses. In the 14th week, we collected blood samples and given an additional booster dose. Upon administration of the booster dose in Week 14, IgG levels increased further, reaching a maximum on Week 15, and remained elevated for subsequent weeks (FIG. 11E). Likewise, AuNS-chitosan-SC2-spike DNA vaccination also elicited S antigen-specific IgA with similar kinetics of induction and time-to-peak levels (FIG. 11F). It also exhibited a sustained peak plateau in serum for two to eight weeks, which is not usually observed after 1M vaccination, especially because of its short half-life and seroconversion pattern.

This distinct pattern of consistently higher levels of IgA generated over the course of treatment can be regarded as a critical advantage, specifically because of the spatial distribution of IgA on mucosal surfaces and the IN route of administration used in this research. Multiple studies have found that IgA possesses superior antiviral properties when compared to the IgG for influenza and for SC2. Sterlin et al. recently suggested IgA dominates the early neutralizing response to SC2 and they deduced that serum IgA is 7-fold more potent than serum IgG in viral neutralization;[35] these advantages could be effectively harnessed by the vaccination strategy adopted in our study. Our finding of the heightened mucosal immunity via IgA could confer an important advantage in preventing SC2 infections, given that the virus attacks respiratory epithelial cells by docking to ACE2 protein on the surface of type-2 alveolar cells.[36, 37]

Figure 11G:
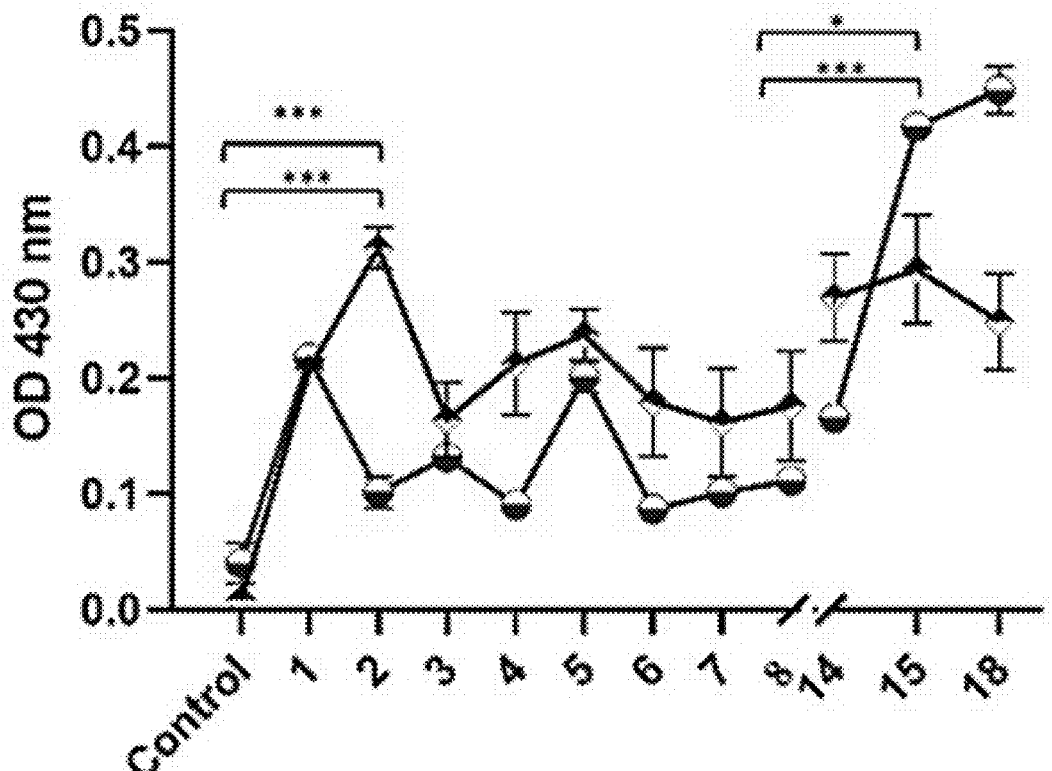
Figure 11G:
Figure 12A:
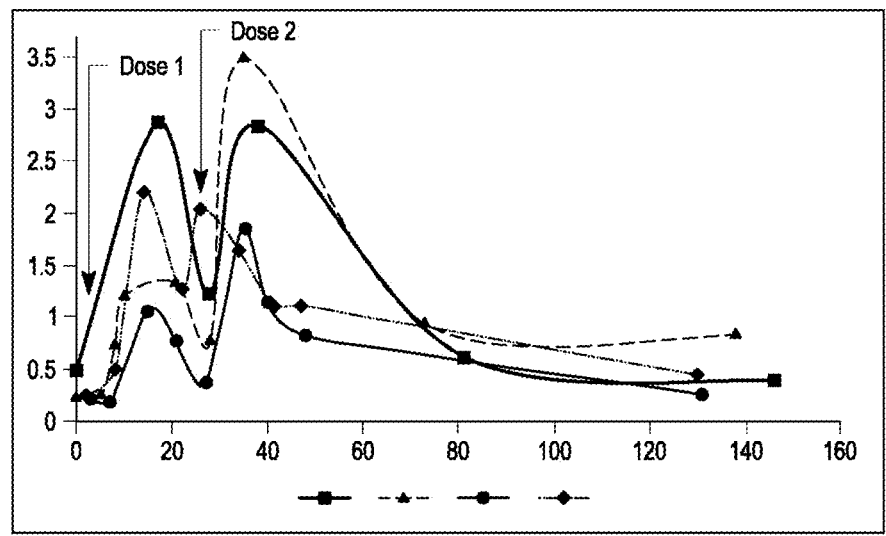
Figure 12A:
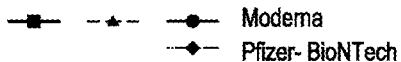
Figure 12B:
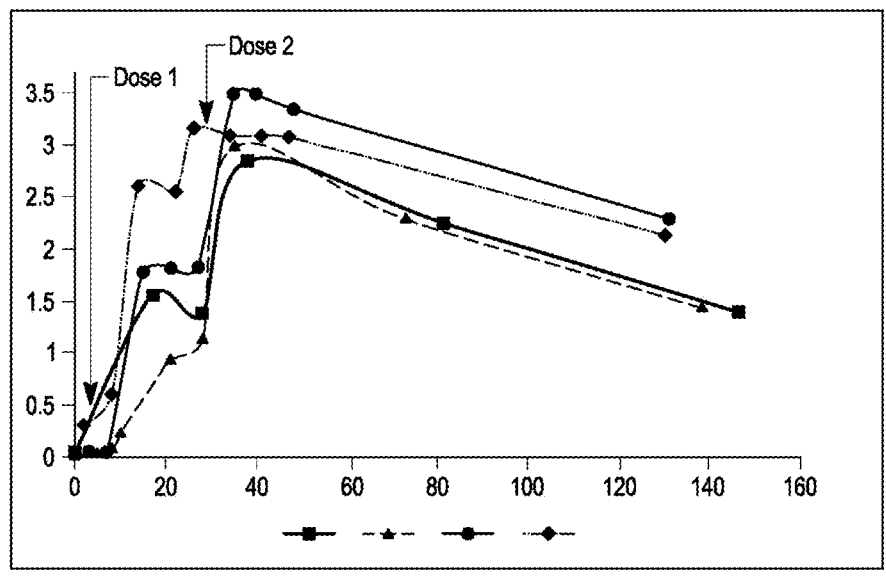
Figure 12B:

On the other hand, existing evidence indicates good correlations between serum and salivary IgM and IgG antibody levels, whereas there is a much weaker correlation between serum and salivary IgA antibodies. This is not unexpected, as salivary IgM and IgG are largely derived from the circulation, whereas salivary IgA is mostly generated locally in the salivary glands.[38] Thus, it can be inferred with confidence that the levels of S antigen specific IgA in the bronchoalveolar lavage and saliva of vaccinated mice would be much higher than the values determined from serum. SC2 specific IgM and IgA were generated as early antibody responses followed by SC2 specific IgG antibodies.[35] The IgG levels are assumed to continue lifelong as protective antibodies against SC2. However, onset of seroconversion also determines respective levels of immunoglobulins, including IgG and IgM synchronous seroconversion; IgM seroconversion earlier than IgG, and IgM seroconversion later than IgG.[39] IgG and IgA sustained their levels till Week 14 and rose even higher with a single booster dose (FIGS. 11E-11G). The quick surge in levels of IgG, IgA, and IgM following a booster dose in Week 14 also represents clear evidence of long-lasting memory B and T cells that are able to trigger a rapid recall response. Humoral immune responses are typically characterized by primary IgM antibody responses followed by secondary antibody responses associated with immune memory, composed of IgG, IgA, and IgE. Here, we observed humoral responses to SC2 in the form of SC2-specific neutralizing antibodies in the blood pool. Overall, our findings demonstrate that AuNS-chitosan-SC2-spike DNA vaccines effectively induce S antigen specific IgG, IgA, and IgM responses in immunocompetent mice, with marked differences in their persistence in serum.

Intranasal delivery of DNA vaccine expressing the S-protein if SC2 using AuNS-chitosan showed efficient activation of pulmonary immunity with neutralizing antibodies.

Figure 13A:
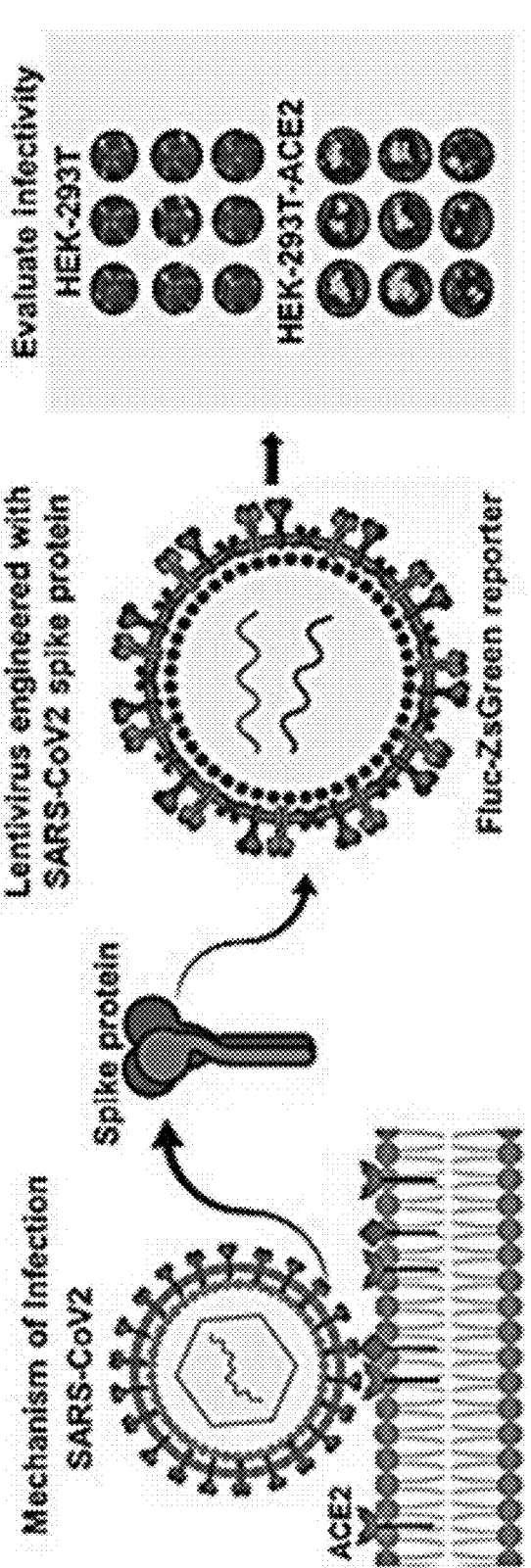
Figure 13B:
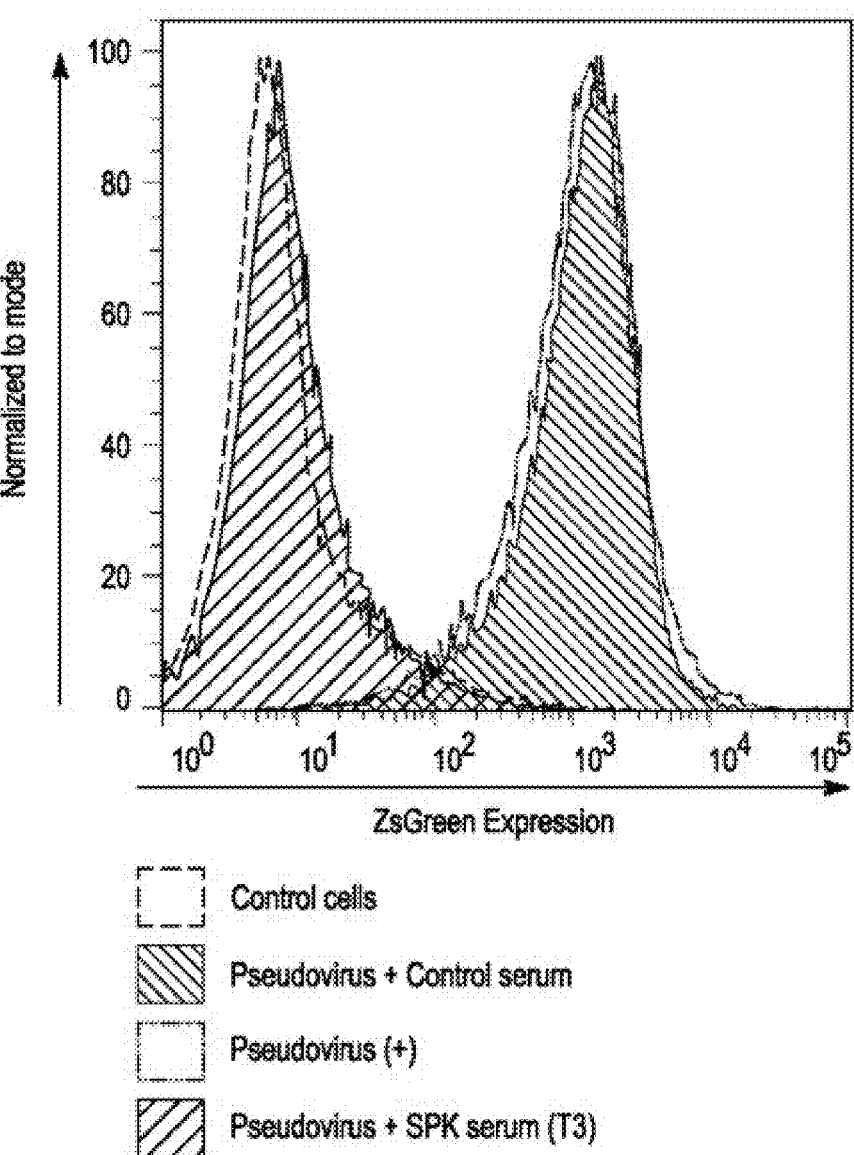
Figure 13C:
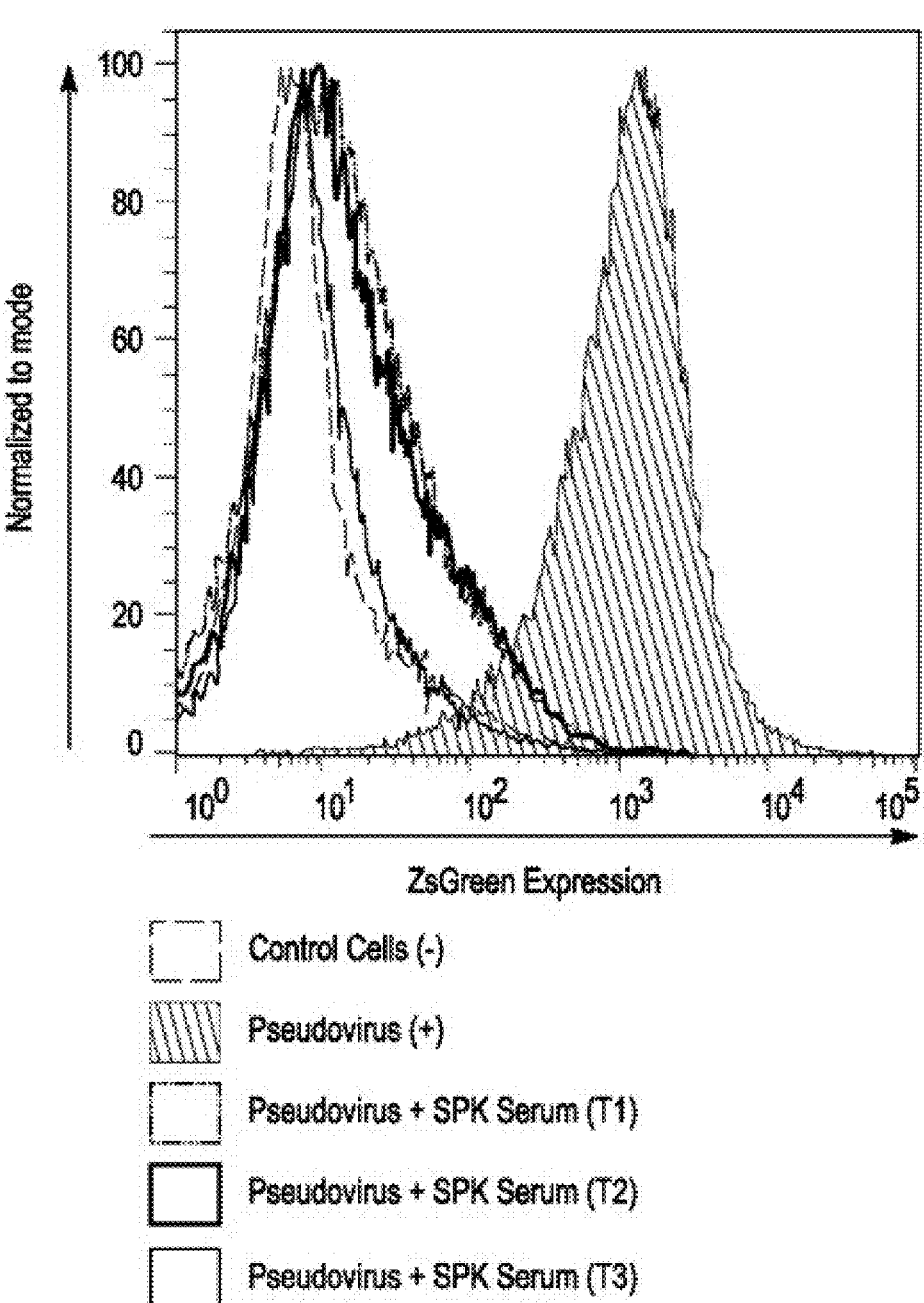
Figure 13D:
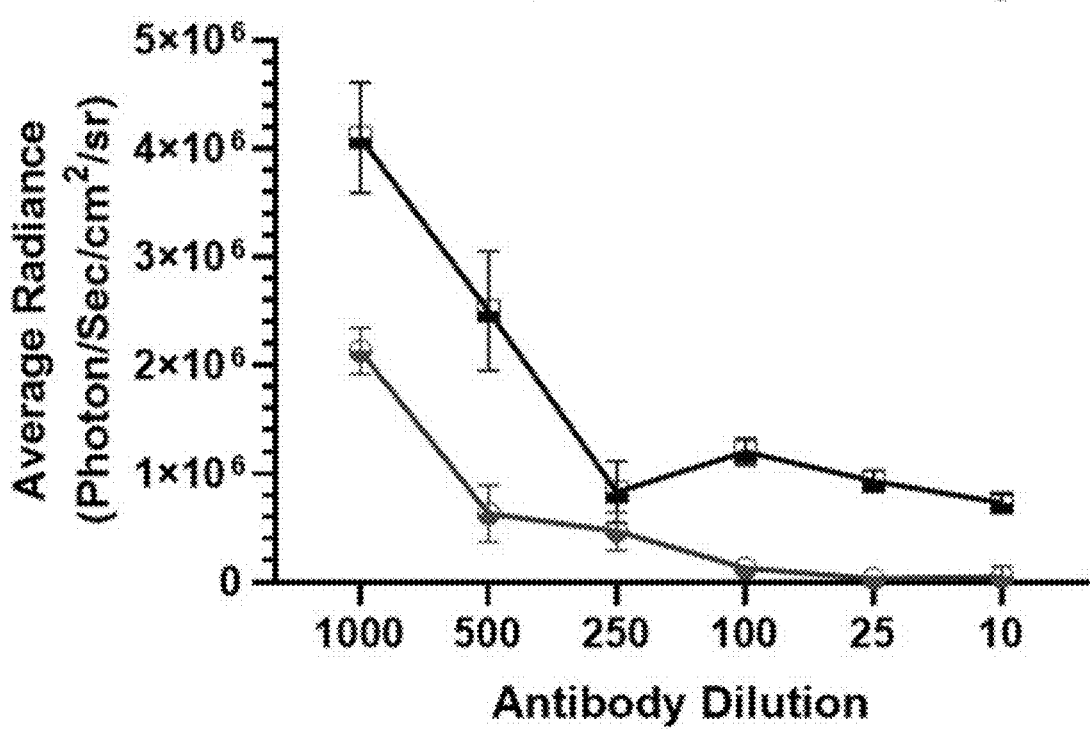

After successful evaluation of antibody induction by the delivered DNA vaccine, we tested the neutralizing effects of antibodies using lenti-pseudoviruses displaying the S protein of SC2 and expressing Firefly luciferase (FLuc)-Zs-Green reporter gene as a pseudovirus for a neutralization assay (BEI resources, NIAID). We first tested the specificity of spike-*lenti*-pseudoviruses for their infectivity to cells expressing the human ACE2 receptor. We infected viruses of the same titer to control cells and ACE2 expressing HEK293T (HEK293T-ACE2) cells, and assessed for infectivity 72 h post transduction using BLI. We observed selective transduction of pseudovirus into HEK293T-ACE2 cells, which established them as a suitable model to mimic infectivity of SC2 in the presence of neutralizing antibodies in different conditions (FIG. 13A). After confirmation of pseudovirus for its selectivity, we used the virus along with serum from mice (BALB/c and C57BL/6J-DR) collected different time points after DNA vaccine delivery to evaluate neutralizing antibody effects. We used a validated neutralizing antibody from a commercial source (SARS-CoV/SARS-CoV-2 Spike antibody, Chimeric Mab [SinoBiological]) as a positive control, while serum collected from control DNA treated mice was used as a negative control. The serum/Ab in different dilutions were incubated with pseudovirus ($5 \times 10^6$ viral particles) in 50 µL serum free medium for 1 h and added to cells ($0.5 \times 10^4$ cells/well in 96-well plates) by mixing with 50 µL of 2× medium. The cells were incubated further for 60 h and used for BLI after addition of 100 µg/mL D-Luciferin (D-Luc) using an IVIS Lumina imaging system. Antibodies from mice immunized with AuNS-chitosan-SC2-spike protein of Wuhan strain neutralized luciferase-expressing SC2 pseudovirus encoding the S protein of the same strain, which was reflected in the decline of FLuc signal. The time dependent variation in the antibody titer was also measured using ZsGreen-based FACS analysis, which correlated well with the trend observed in BLI (FIGS. 13B-13D). The histogram for pseudovirus transduced ZsGreen expression in HEK293T-ACE2 cells in the presence of serum collected from vaccinated mice on Week 3 was fully displaced towards the lower end and overlapped with that of control cells that were not subjected to pseudovirus transduction. Our findings indicated presence of a high titer of neutralizing anti-SC2 S antigen specific antibodies generated in the vaccinated mice, which could completely prevent the infection of SC2 pseudovirus in HEK293T-ACE2 cells.

Intranasal delivery of DNA vaccine expressing the S-protein of SC2 using AuNS-chitosan induced efficient production of neutralizing antibodies effective against different variants of SC2.

Figure 13E:
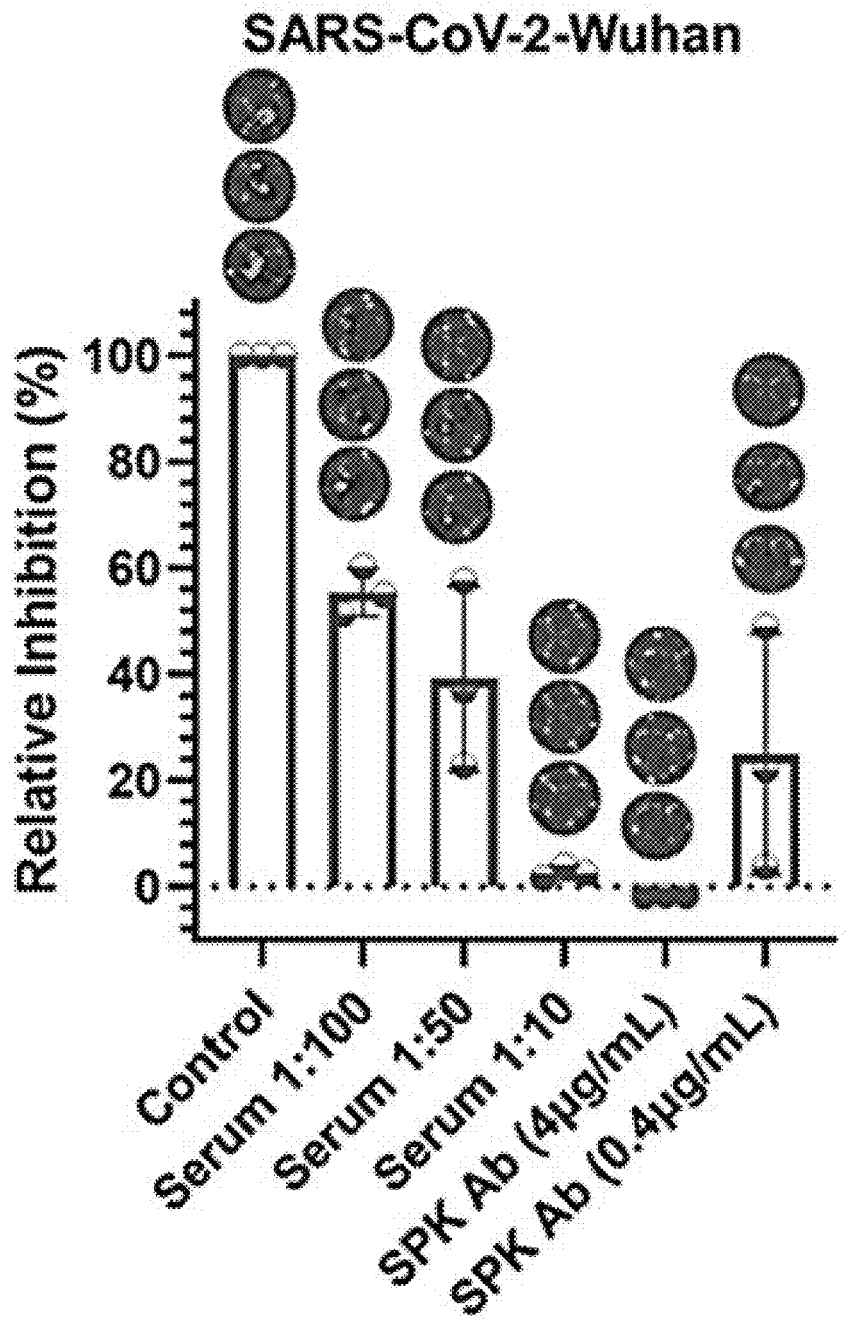
Figure 13F:
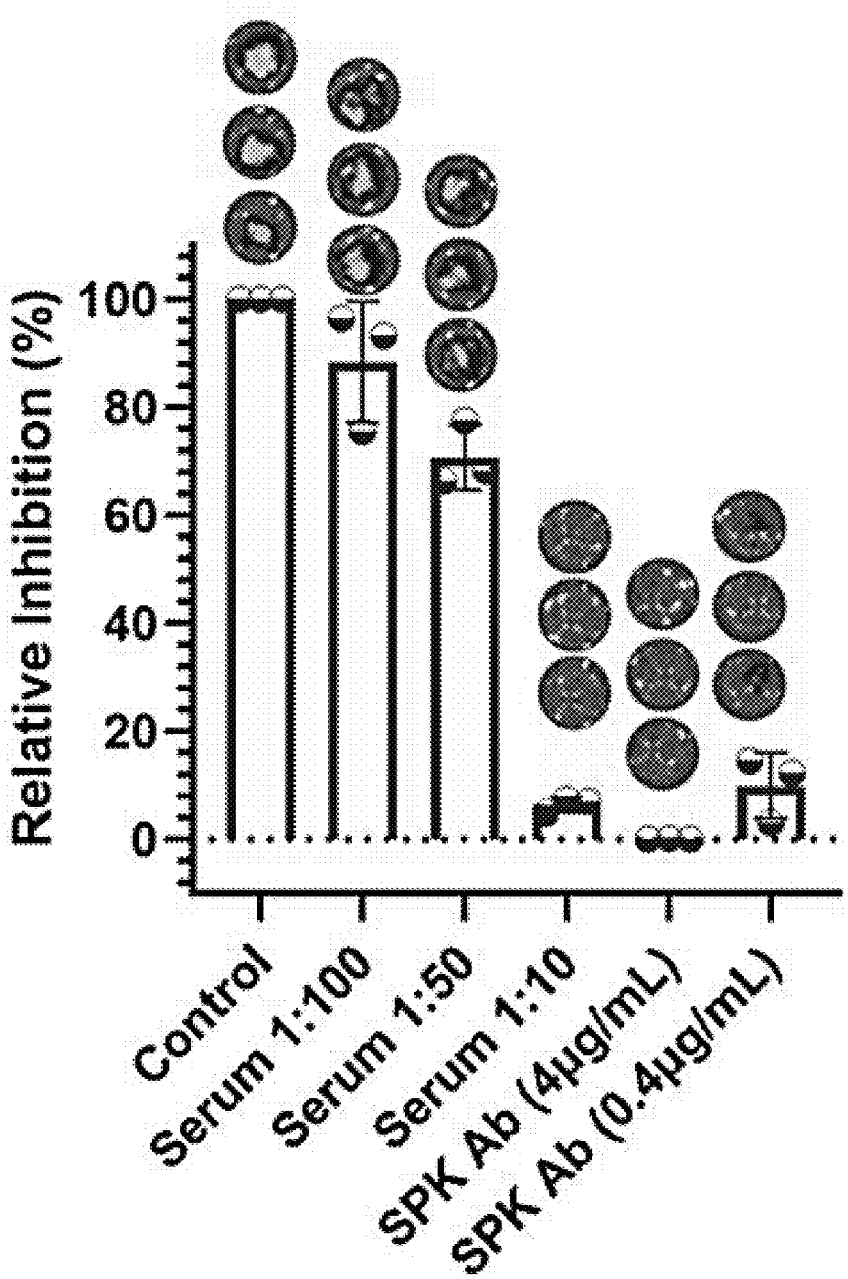
Figure 13G:
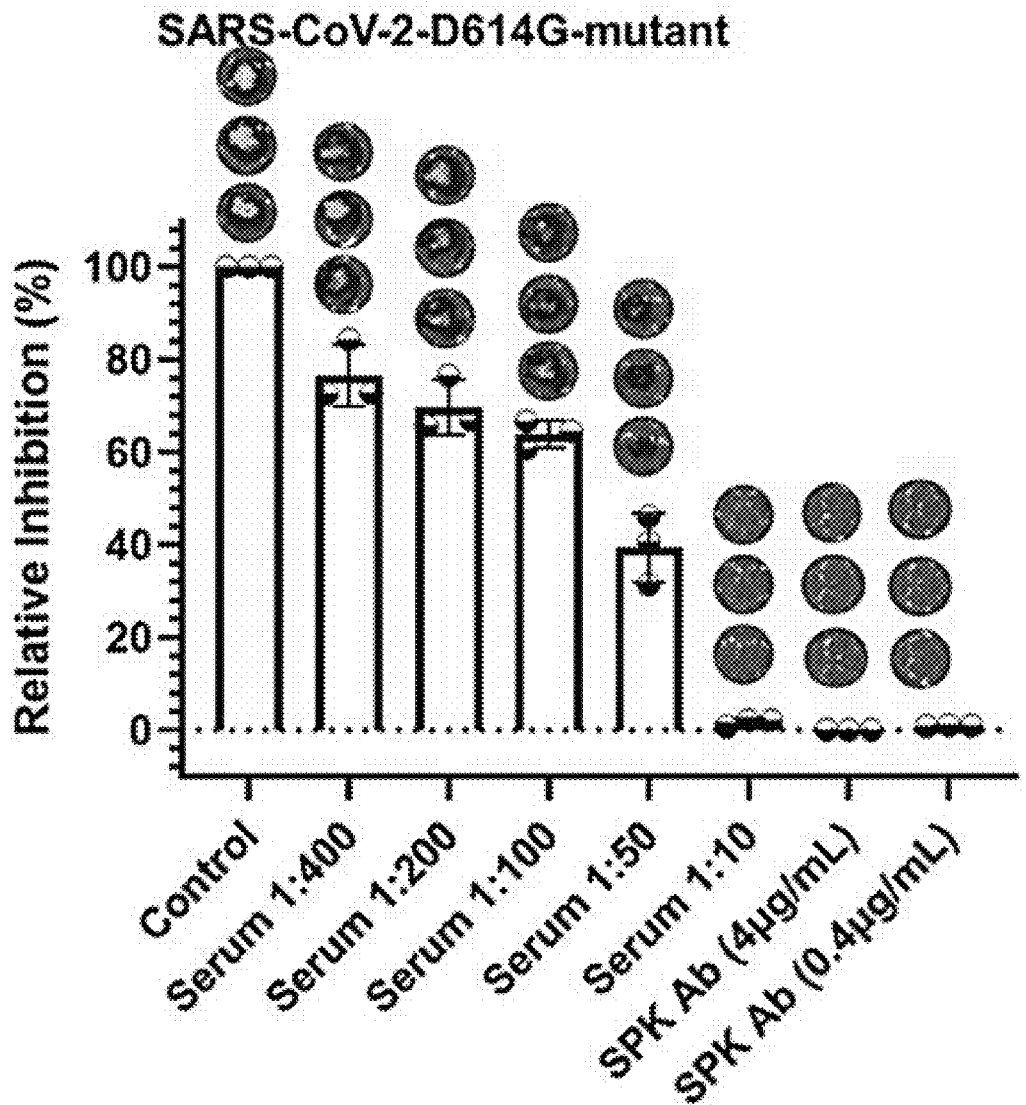

To investigate the efficacy of neutralizing antibodies generated in vaccinated mice against new emerging mutant variants of SC2, we evaluated the infectivity inhibition of vaccinated mice serum against SC2 pseudovirus with the S protein of Wuhan strain, D614G mutant, and the South African variant (SC2-SA-mutant).[40] We observed a dose dependent neutralizing effect by serum collected from mice treated with the DNA vaccine, and the results were represented as relative inhibition of infectivity (FIGS. 13E-13G). The HEK293T-ACE2 cells transduced with pseudovirus in the presence of serum collected from control DNA treated mice served as control, with 100% infectivity. In the absence of SC2 S antigen specific antibodies in the control DNA treated mice sera, the levels of pseudovirus infectivity were similar to those of cells transduced using pseudovirus in the absence of serum. We used vaccinated C57BL/6J mice serum with peak titers of anti-SC2 antibody achieved after booster dose administration for evaluating the neutralization assay, which corresponded to serum collected at Week 18 of the study. We used the serum at different dilutions to study the correlation of antibody titers in serum with infectivity of pseudovirus, and compared with that of commercial anti-SC2 antibody. We observed a dose dependent (serum dilutions) decline in infectivity, and at 1:50 dilution of serum, we found nearly complete inhibition of infectivity, which was almost similar to that achieved by commercial antibody at 4 µg/mL concentration (SARS-CoV/SARS-CoV-2 Spike antibody, Chimeric MAb). These trends were consistent across all three strains of pseudoviruses engineered for different variants of SC2 S proteins (i.e., SC2-Wuhan, SC2-SA-mutant, and SC2-D614G-mutant) with marginal difference in inhibition at higher serum dilutions. At 1:50 serum dilution, the infectivity of both SC2-Wuhan pseudovirus and SC2 D614G-mutant variant diminished to 38%±22% and 38%±5%, respectively, whereas for SC2-SA-mutant variant, the infectivity dropped to only 67%±7%. Despite these variations at higher dilutions of serum, when we used 1:10 serum dilution for the assay, infectivity of all three variants was inhibited completely, indicating the efficacy of this DNA vaccination approach against emerging mutant variants (FIGS. 13E-13G).

Intranasal delivery of DNA vaccine expressing SC2 S protein using AuNS-chitosan effectively induced cell-mediated immunity in C57BL/6J-DR mice.

A cell-mediated immune response plays a critical role in combating viral infections.[41] It is comprised of T cell responses that fundamentally differ from antibody (humoral) responses in that they result in infection control. Cell-mediated immunity is primarily driven by mature T cells, macrophages, DCs, NK cells, and the released cytokines, in response to antigen delivery.[42] In order to deduce the role of cell-mediated immunity after IN DNA vaccination, we performed immunophenotyping of leukocytes collected from lungs, spleen, thymus, and lymph nodes of mice delivered using control DNA and DNA coding for S protein of SC2 using AuNS-chitosan NPs. The major immune cell subsets that confer protection to the pulmonary immune system include AMs, DCs, T helper (TH) lymphocytes, cytotoxic T lymphocytes (CTLs, or TC), memory lymphocytes, NK cells, and B cells.[43, 44] We succeeded in isolating CD45+ positive populations with greater than 90% purity in all four sample sources (FIGS. 16B-16E).

SC2-spike DNA vaccine mediated antigen processing and immune cell activation in the lungs and spleen.

The important cellular mediators of pulmonary immunity consist of phagocytic cells (AMs, neutrophils, eosinophils) and NK cells.[45] They have the capacity to recognize and neutralize SC2-spike antigen expressing cells. Although circulating naive T lymphocytes are major responders in cell-mediated immunity, they have a limited capacity to leave the blood stream and migrate into peripheral tissues. Therefore, an important requirement that precedes the induction of adaptive immunity for SC2 in the lungs is the transport of antigen from the site of initial exposure to the T cells of the draining lymph nodes.[46] Such a transportation of antigen via afferent lymphatics is a specialized function of alveolar DCs.[47] We observed these initial events of interaction in our immunohistochemistry analysis of lungs from SC2-spike vaccinated mice.

Lung tissue stained for detection of immune cells and S protein show expression of transfected S protein in the endothelial cells lining the bronchi and alveoli, which are selectively recognized by the DCs. Some of these spike-DNA NPs are also directly captured and internalized by DCs from their extension through epithelial junctions and by other antigen-presenting cells (APCs).[48] These S antigen primed DCs process the antigen and drain into lymph nodes (FIG. 18) to prime other components of the cell-mediated immune response to home to the lungs. The presence of DCs in high density in the proximal airways and their inherent high phagocytic ability places them in a perfect position to capture S antigens expressed by the endothelial cells. Their strategic distribution, and their ability to capture and process antigen, and present them to T cells in the lymph nodes, all make DCs the key APCs in the lungs and in other mucosal surfaces.[49]

For example, analysis of spike expression and immune presentation in the lungs show that interaction of the immune-surveillant DCs present in the airway epithelium with cells expressing SPK antigen enacts their role as professional antigen-presenting cells to NK cells and stimulates T cell response (data not shown). The phagocytic alveolar macrophages also complement DCs in antigen presentation but at relatively low levels as they lack costimulatory molecules.

Our FACS analysis results of lymphocytes in lungs of S treated mice revealed an increase in CD11c+ DCs (7.5%), also accompanied by a surge in CD8+ T cells (5.5%). This explains the arrival of CTLs (MHC class I-restricted T cells) from lymph nodes into the lungs (FIG. 16C). The CD11c+ DCs represent the major DC subset in the lungs for cross-presenting antigens to CD8+ T cells, promoting viral clearance and directing T helper type 2 (Th2) responses to S antigen.[50] On the other hand, CD4+ T cells respond to the antigen presented on MHC-II, located primarily on APCs.

A plausible exposure to S antigen can induce naive CD4 T cell expansion and differentiation into effector cells, TH1, TH2, TH17, or Treg phenotypes, some undergoing further differentiation into memory cells that reactivate rapidly upon antigen re-exposure.[51] Thus, we evaluated the expansion of CD4+ T cells in lungs of S vaccinated mice, not only for effector and memory functions, but also for their role as T helper cells in the germinal centers of spleen and lymph nodes.[52] We observed the levels of CD4+ T helper cells in S treated mice to be increased marginally by 4.2%, which plausibly accounts for the presence of surviving T cells that remain in the alveoli as resident effector memory cells. Once activated, T helper cells activate B cells in the lymph node (B cell zone) and redirect them into lungs via the systemic circulation.[53] In agreement with this pathway, SPK treated mice manifested a 6.1% increase in CD19+ B cell populations (FIGS. 16B-16E). As these lung resident B cells represent a major component of adaptive immunity and account for antigen specific immunoglobulins against SC2 vaccine, it can be deduced with certainty that increase in B cells in the lungs correlate with generation of systemic SC2 specific IgM, IgA and IgG immunoglobulin responses (FIGS. 11E-11G).

In addition to DCs and T cells, resident AMs comprise >90% of the cells in the alveolar lumen and are indirectly in contact with DCs in the alveolar wall, which prompts a response for S antigen presentation by DCs.[54] We also observed a prominent increase (10.3%) in CD11b+ macrophage levels in lungs of S vaccinated mice to indicate their role in arming the cell-mediated immune response. As these resident AMs reside in close proximity with endothelial cells, they also come into contact with conventional DCs that extend dendritic snorkels into the alveolar lumen.

For example, analysis of the distribution of monocytes, NK cells, and DCs in lungs of untreated mice, pcDNA treated mice, and SPK DNA vaccine transfected mice show an increased presence of DCs in the alveoli and bronchi (data not shown). This indicates the arrival of circulatory DCs to complement the role of tissue resident alveolar DCs in recognition and processing of SPK antigen. The monocytes and alveolar macrophages are the other class of resident lung phagocytes that are recruited to the alveoli as well as closely associated to the bronchial epithelium expressing S protein to mediate recruitment of additional leukocyte subsets to the lungs. Furthermore, evaluation of the role of NK cells on DC and T cell responses in lungs upon IN administration of SPK vaccine shows that the increase in peripheral, immature local DCs in the SPK vaccinated lungs and their maturation and migration to draining lymph nodes drives the T cell response (CD4+ and CD8+ T cells) from the lymph nodes (data not shown). As result of this effector T response CD4+ and CD8+ T cells increase in lungs. On the other hand, increase in classical effector cells of the innate immune system i.e. NK cell complements in mounting T cell mediated SPK immunogenicity and also play a protective role in mitigating inflammation and tissue damage by modulating DC function to impact T cell responses.

From the circulation, DCs can enter the spleen in the marginal zone (MZ) sinus at the border between white and red pulp (RP) and mount a response. We observed such events of DC migration from marginal zones into GCs on spleen histology of S vaccinated mice. This stood in stark contrast to spleens from pDNA treated mice. Increased presence of DCs in the white pulp (WP) triggers adaptive immune responses from the spleen against simultaneous pancreas kidney (SPK) antigen.[55] Therefore, IN immunization induces mass DC migration into the T cell zone of the WP (FIGS. 16B-16E).

For example, characterization of immune cells in the spleen (data not shown) shows that differential intrasplenic migration of DC subsets tailor adaptive immunity. Spleen is divided by function and structure into red pulp (RP) and white pulp (WP); between these two regions is the marginal zone (MZ). The cDC arriving from spike vaccinated lungs modulate the dynamic architecture of immune cells in the spleen that regulates T and B cell responses. Upon activation by an innate immune response to S antigen, the cDCs migrate from the "peripheral tissue" of the spleen (MZ and RP) to the "lymph node" of the spleen (WP), i.e., the splenic T cell zone. DC migration from marginal zones into germinal centers leads to selective induction of either CD4+ or CD8+ T cell responses.

Likewise, FACS analysis of splenocytes from SC2-spike DNA vaccinated BALB/c mice also indicated 7.4% increase in CD11c positive dendritic cells, which was accompanied by 6.31% increase in B cell population. These results correlated well with histological evidence of cDC (circulatory DC) migration from marginal zones into GCs (FIG. 16B).

Figure 16A:
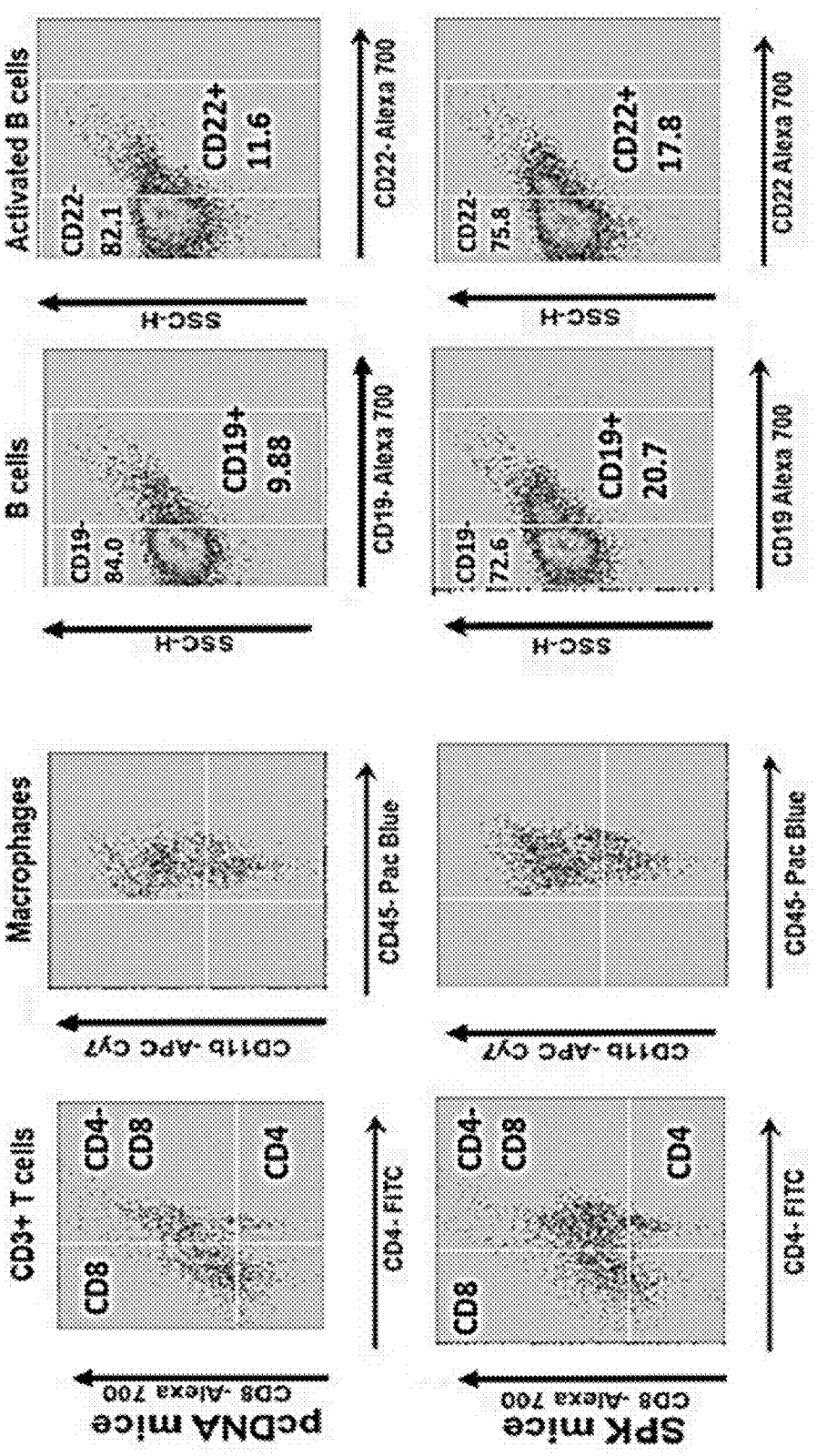
Figure 16B:
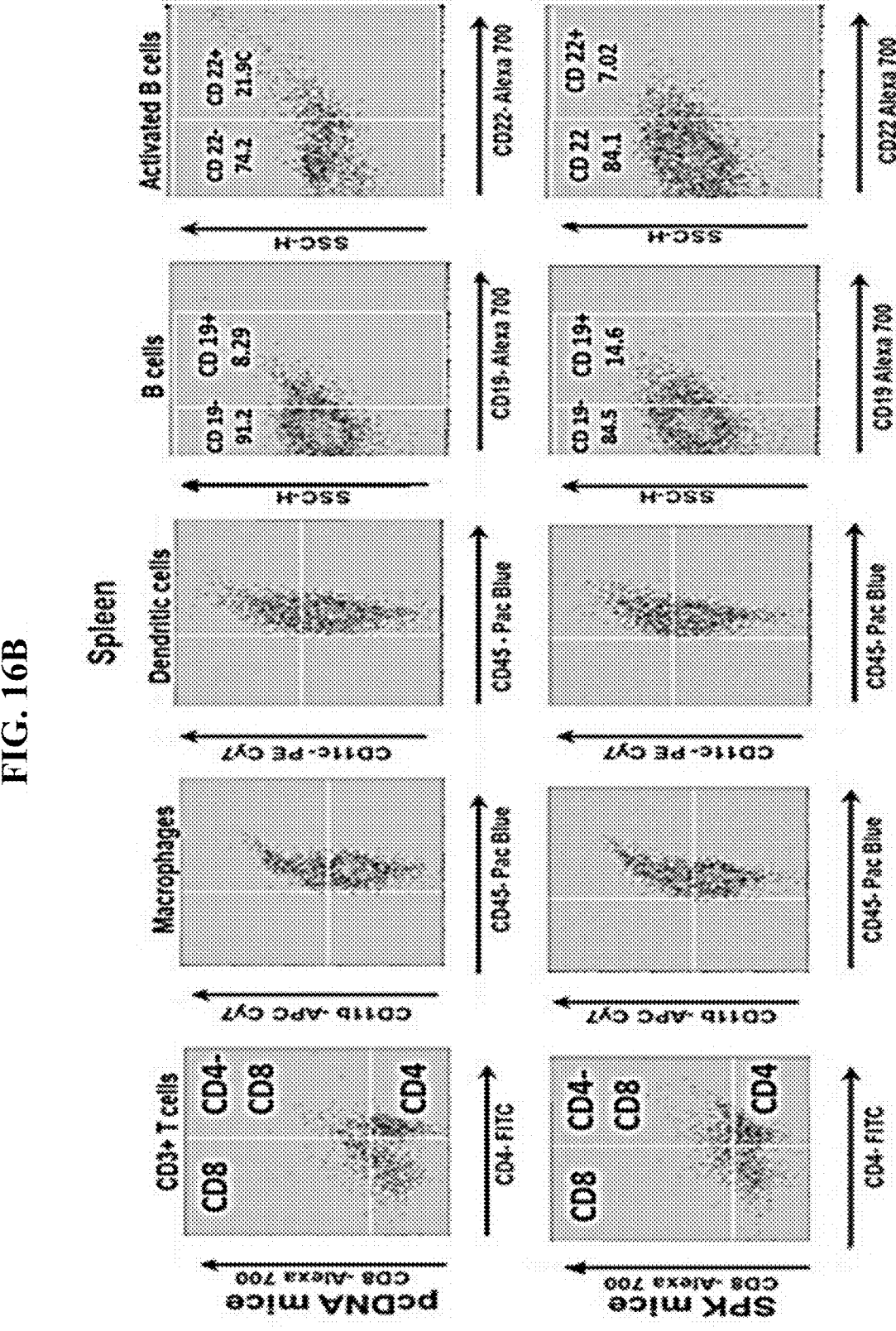
Figure 16C:
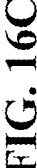
Figure 16D:
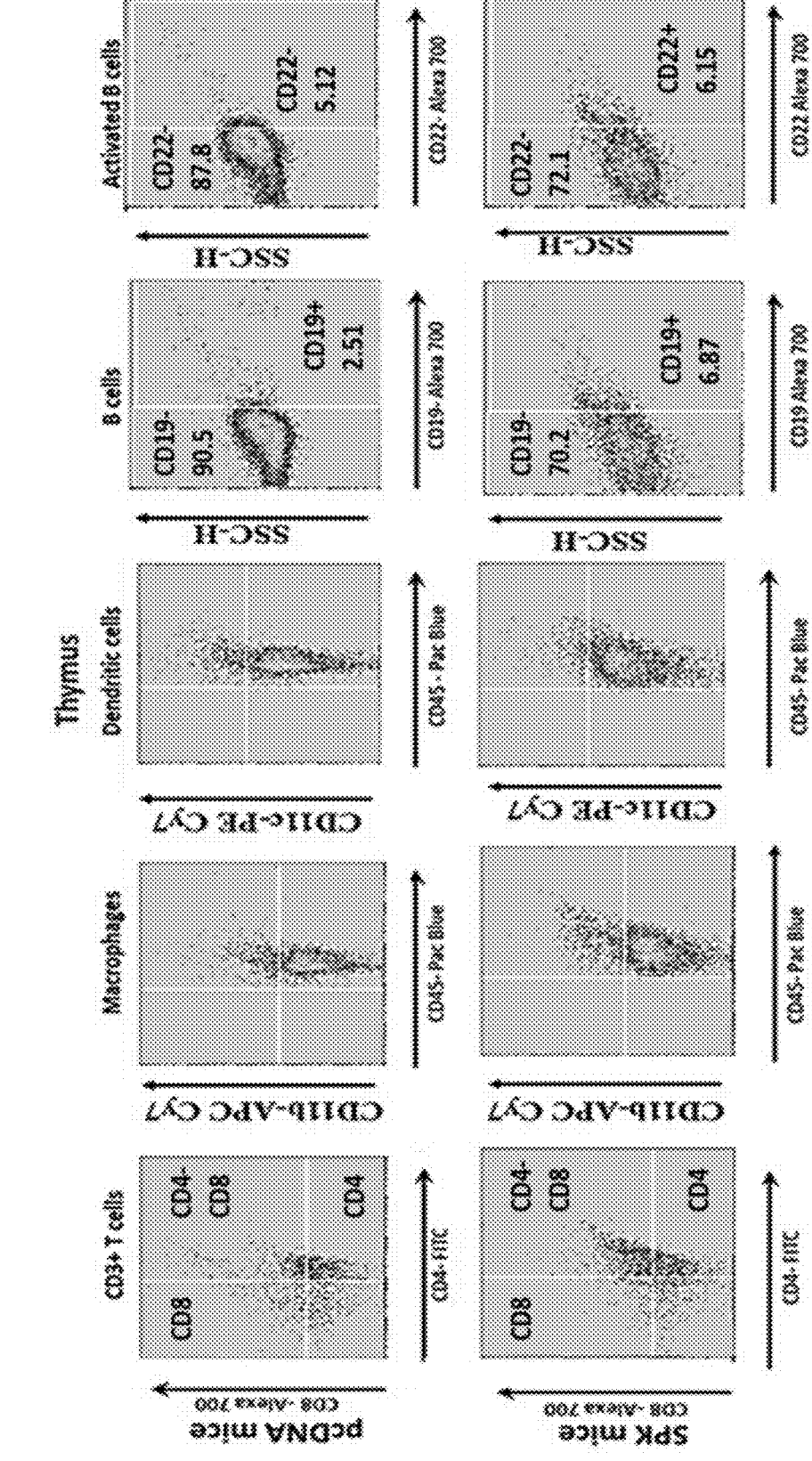
Figure 16E:
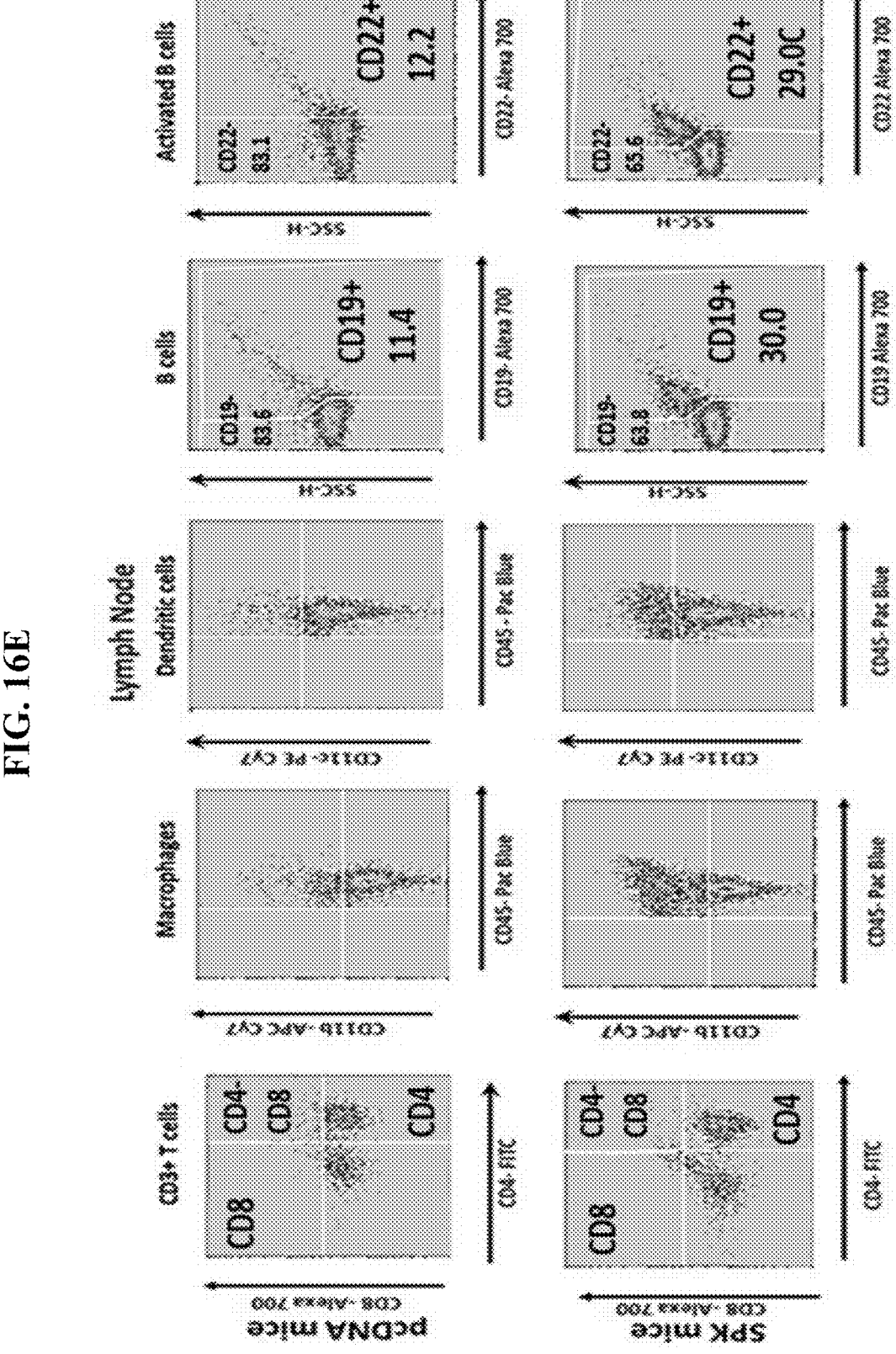
Figure 17A:
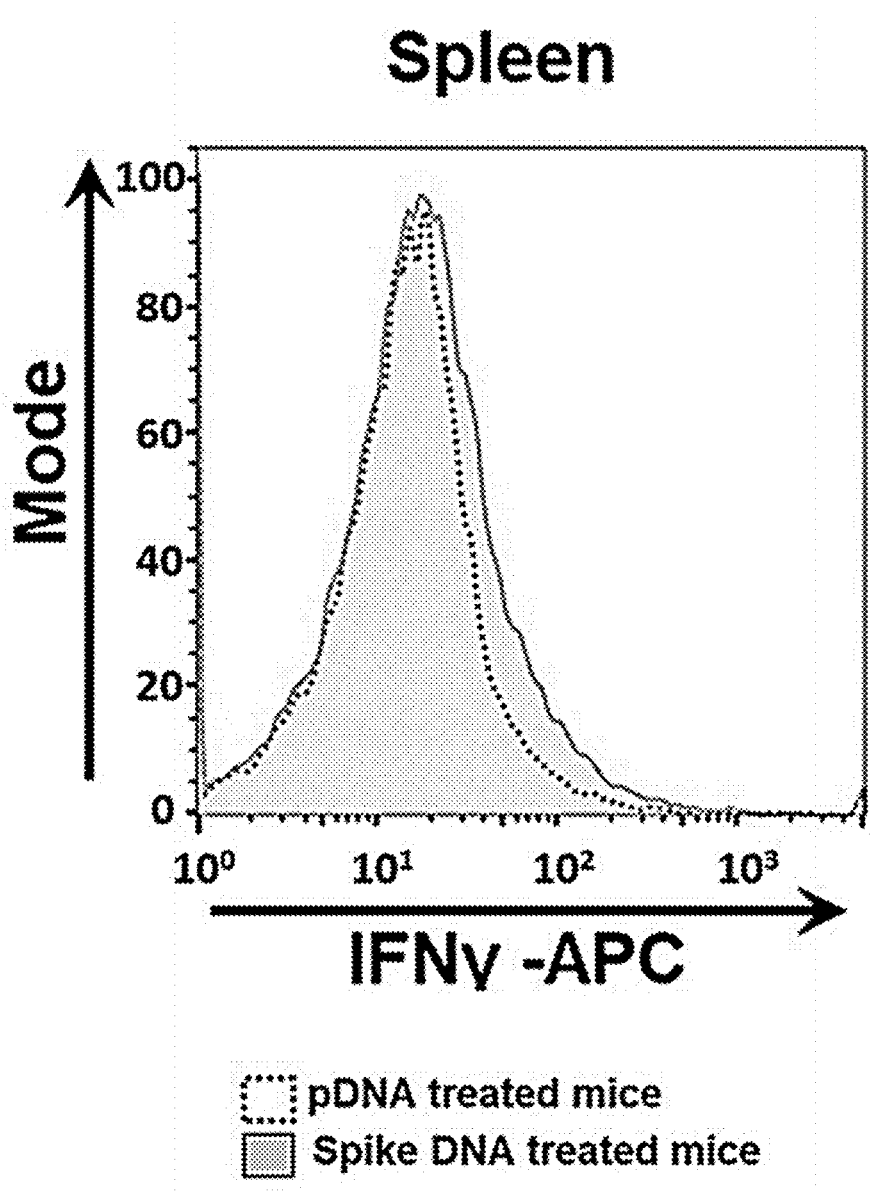
Figure 17B:
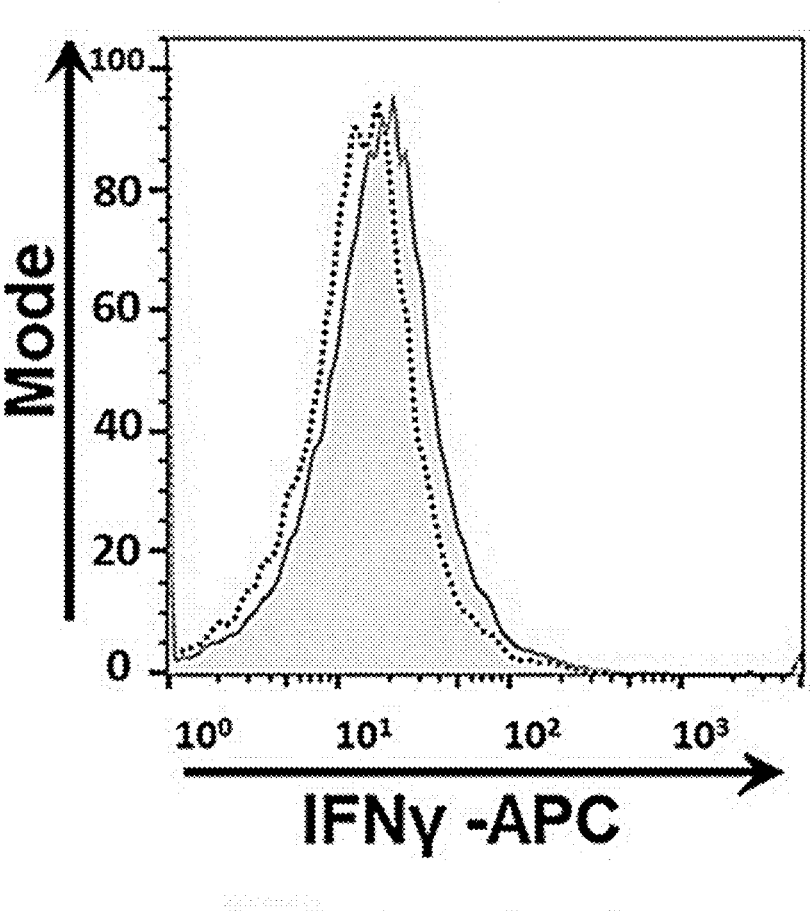
Figure 17C:
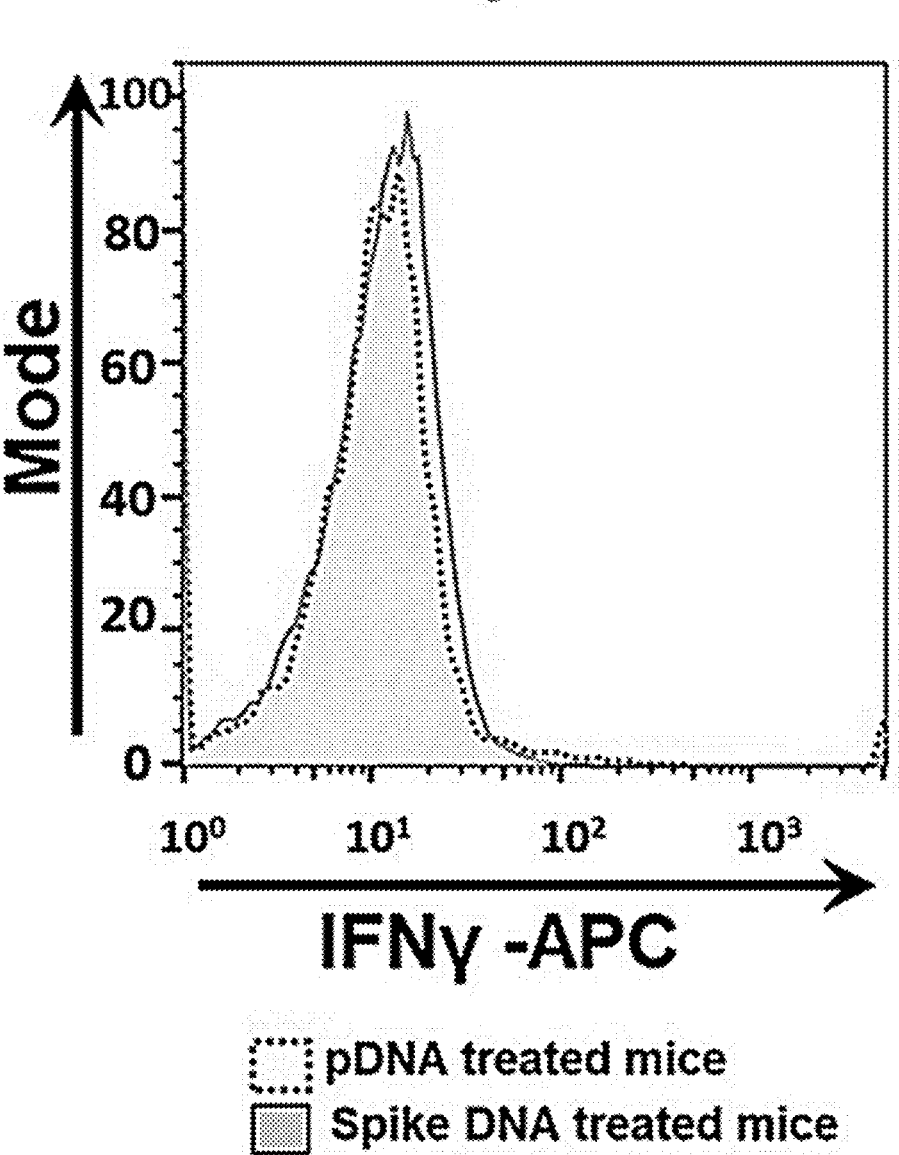
Figure 17D:
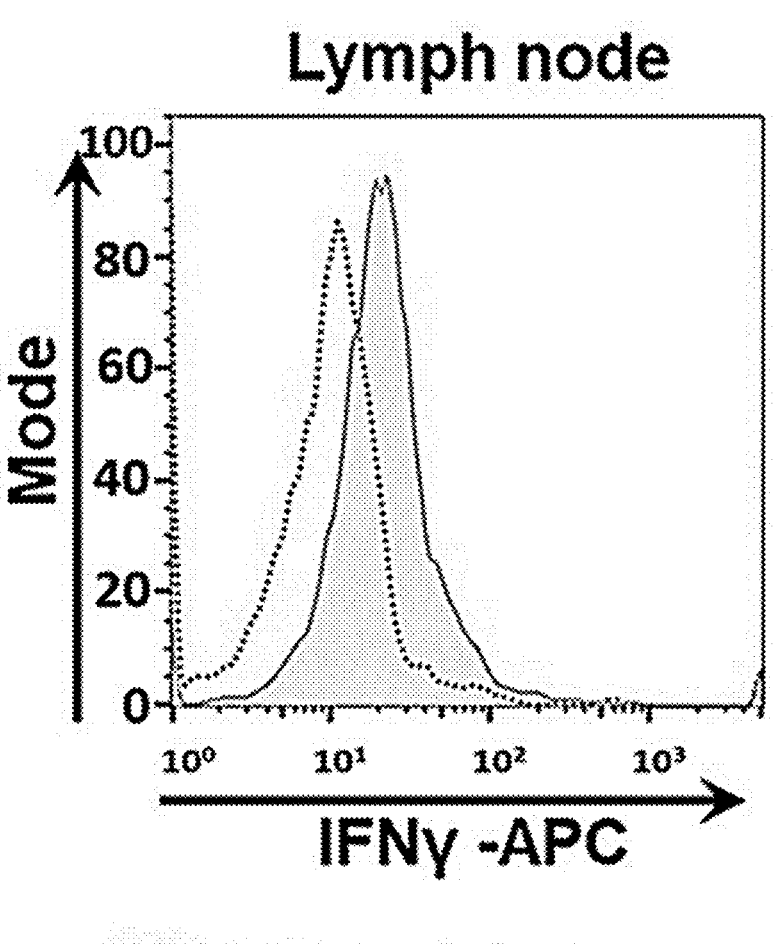
Figure 17D:
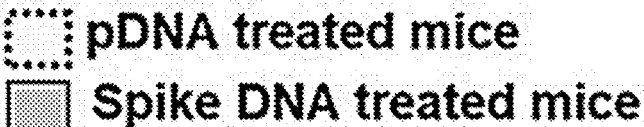
Figure 17E:
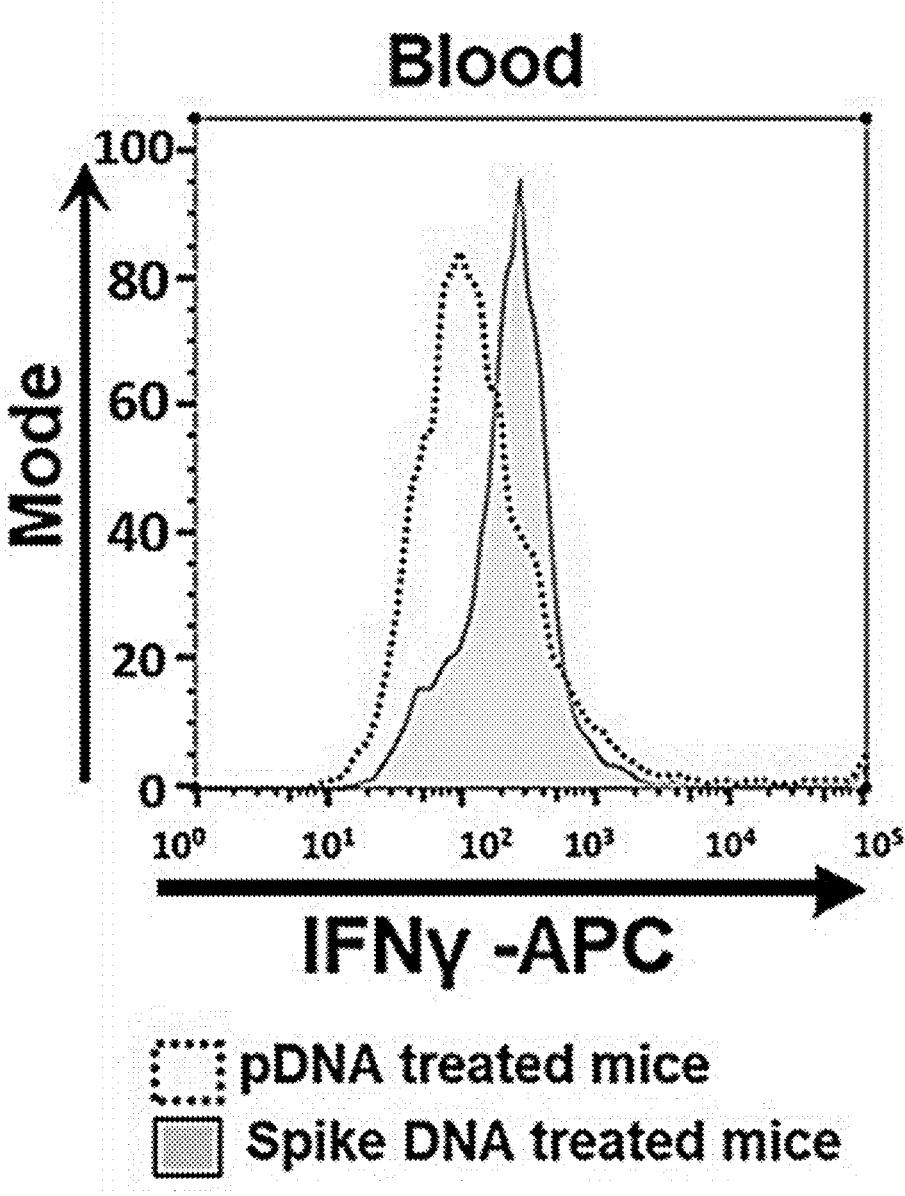

The synchronous surge in DCs and B lymphocytes in the spleen of vaccinated mice suggested that DCs were involved in transport and transfer of SC2 antigen to naive B lymphocytes, and upon this adoptive antigen transfer, B cells triggered SC2 specific antibody responses (FIGS. 11E-11G).[56,57] On the other hand, SC2 activated cDC interaction with B lymphocytes also primes subsequent T cell dependent response, and in agreement with this postulation, vaccinated mice manifested ~7.9% increase in CD4-CD8 double positive T cells (FIG. 16B).

Alongside the professional APCs, such as DCs, other APCs (macrophages) are also actively involved as promoters of germinal center B cell response.[58] Splenic macrophages are compartmentalized into white pulp, red pulp and marginal zones, and each of them play distinct roles in immune responses. The arrival of SC2 activated macrophages in the strategic location of the marginal zone and white pulp, places them in close proximity for interactions with both B and T cells to participate in SC2 immune responses (data not shown). Significantly, marginal zone (MZ) B cells are the major constituent of the marginal zone, together with myeloid, dendritic, and stromal cells. These MZ B cells are the main producers of IgM antibodies against S antigen. The enrichment and mobilization of MZ B cells indicate the characteristics of splenic immune response.

Similarly, we observed increases in prevalence of macrophages and monocytes in the white pulp and the marginal zones of spleens from SC2 vaccinated mice. This correlated well with a synchronous surge in CD11b+ macrophages by 10.3%, accompanied by 6.3% increase in B cells in the spleens of SC2 vaccinated BALBc mice (FIG. 16B).

Lastly, we evaluated for the presence of any toxic effects in the lungs of mice treated with multiple doses of the DNA vaccine, and in controls (N=3). Hematoxylin and Eosin staining of histological slices of lung and spleen tissues collected from mice treated with pDNA or pDNA-SC2-spike delivered using AuNS-chitosan was completed for these toxicological observations (data not shown). We observed that there was no significant tissue damage in the lungs of mice vaccinated with the S DNA vaccine.

SC2-spike DNA vaccine-mediated antigen processing, and B and T cell activation in lymph nodes.

Lymph nodes are the critical command centers of the immune response, housing T cells, B cells, and APCs that orchestrate adaptive immunity.[59] APCs, such as monocytes and DCs, can internalize the S antigen expressed in the lungs upon IN delivery of DNA vaccine using AuNS-chitosan, and physically carry the vaccine to lymph nodes. In addition to this role, lymph node-resident DCs possess important functions such as cross presentation for priming CD8+ T cells, which are absent in some tissue-resident DCs.[60] As evident from the interaction of DCs with S protein expressing cells in the lungs (data not shown), it would be expected that these DCs capture S antigen, proteolyze it into short peptide fragments, and load these peptides onto class I and class II MHC molecules, which are then physically presented on the surface of CD8+ and CD4+ T cells.[61] At the same time, it would be expected that APCs that have encountered SC2-spike antigen to migrate to the nearest lymph nodes in order to activate naive T helper cells. Once activated, T helper cells activate B cells that have encountered the same S antigen presented by DCs and macrophages.[62] Unlike typical macrophages, the subcapsular sinus macrophages direct target specific immune responses to a variety of lymph-borne pathogens by relaying antigens to B cells, producing cytokine signaling cascades to cause influx of DCs, neutrophils, NK cells, or in some conditions, presenting antigens to T cells, and SC2 vaccinated mice showed presence of such subcapsular sinus macrophages and DCs (data not shown).[63] Activation of B cells is often triggered by binding of S antigen to the B cell receptor, which can occur through B cell recognition of S antigens captured on cell membranes of APC in the lymph nodes.[64] As we could see a consistent dose dependent surge in S specific immunoglobulins (IgG, IgA and IgM) in vaccinated mice, it is certain that B cells in these mice were activated by the delivered S DNA vaccine and orchestrated the antigen specific response. In view of this concept, we further investigated the role of lymph nodes in mounting this B cell response, especially because of their crucial role in maturation and activation of B cells. Our results from histology staining show that draining lymph nodes bring together spike activated cDC, NK cells and macrophages for generating spike antigen specific immune response from B cell maturation centers i.e. germinal centers (GCs) (data not shown). Lymph nodes of vaccinated mice depict characteristics of reactive lymph nodes with multi-focal germinal centers with extensive B cell proliferation. The presence of interdigitating follicular dendritic cells (FDCs) in the GCs also validates the S specific B cell assortment in the GC and accounts for the rapid surge in immunoglobulin levels (IgG, IgM and IgA) in vaccinated mice. The events of B cell migration across the marginal zone into the interfollicular space represents short-lived antibody producing cells termed as plasmablasts. Interfollicular zone primes appropriate T cell response as well as B cell maturation.

To investigate whether the SC2 DNA vaccine could trigger such a characteristic S specific immune response in the lymph nodes, we harvested nodes from BALB/c mice treated using SC2 DNA vaccine along with pDNA treated mice as controls (N=3 animals for each condition) and analyzed using FACS to identify distributions of immune cell populations. The nodes are also where cytotoxic T cells are trained with S antigen presented by professional APCs, especially the DCs.[65] Our FACS analysis results indicated this modulation of CD4+ T cells in S vaccinated mice compared to that of pDNA vaccinated mice (FIGS. 16B-16E). The histology of lungs from vaccinated mice indicated the successful delivery and expression of S antigen and also captured the interaction of DCs with these S expressing cells (data not shown).

These migratory DCs in the lungs can transfer antigen to lymph node resident DCs.[66] These S antigen recognition events direct the immune response to the antigen to activate innate immune system pattern recognition receptors or cytokines, as well as chemokines induced in the lymph nodes in response to S antigen-mediated immunization. FACS analysis of both B and T cells in lymph nodes revealed their S antigen-specific enhancement in treated mice (i.e. 18.6% increase in CD19+ B cells and 6.3% increase in CD4+ T cells). Immunization studies in other preclinical models suggest that large amounts of antigens are required to drive CD8+ T cell responses,[66] whereas in our approach the efficient antigen processing and cross presentation by DCs was achieved via the IN route, which also led to a surge in a T cells immune response from the lymph nodes. Higher levels of available antigen and a greater production of follicular helper T cells can govern lymph node GC responses.

The histology of lymph nodes from C57BL/6J-DR mice vaccinated using SC2-spike indicated a characteristic feature of antigen activation. T and B cells were compartmentalized into specific locations, with T cells residing primarily in the deeper paracortex of nodes, while B cells were in the follicles (data not shown). S antigen carried to nodes by lymph or lymphatic-migrating APCs arrive at the subcapsular sinus of the draining lymph node. B cells that receive initial signaling by binding to S antigens enter specialized subregions of the follicles (the GCs). Such dynamic mobilization of B cells was evident in the vaccinated mice when compared to control mice (data not shown).[67] GCs develop in the B cell follicles of secondary lymphoid tissues during T cell-dependent antibody responses.[68] The B cells that give rise to GCs initially have to be activated outside the follicles, i.e., in the T cell rich zones in association with interdigitating cells and T helper cell.[69] Follicular DCs (FDCs) in the light zones are expected to capture and retain S antigen via Fc and complement receptors, which they can present for prolonged periods to local B cells.[70, 71] Within the GC, B cells can acquire antigens from FDCs that are processed and presented on class II MHC molecules. The activated B cells can exit the GC to become short-lived antibody producing cells termed plasmablasts. The results shown from histology staining (data not shown) illustrate the migration of B cells from the GC into the light zone as evidence for the movement of antibody producing plasmablasts in response to the SC2 DNA vaccine. The amount of antigen accumulated in lymph nodes directly correlates with the number of T follicular helper cells and GC B cells that develop in immunized lymph nodes.[72] Thus, the efficiency of S antigen delivery to follicular DCs will also affect responses to immunization. The FDCs are located along with B cells in the follicles of any secondary lymphoid organs.[73] FDCs have very important functions regarding the generation and the selection of high affinity plasmacytes, i.e., memory B lymphocytes, during the adaptive immune response.[74] One key property of FDCs is their ability to trap and display antigens as immune complexes in a highly stimulatory way to proliferating B cells. Within lymph nodes, there is a network of stromal cells that includes the FDCs. FDCs were first identified as "antigen retaining reticular cells".[75] Subsequently, FDCs have been recognized for their unique ability to retain antigens for prolonged periods. This property of FDCs is critical to several immune functions, including GC formation and long-term immune memory.[76] Our lymph node histology indicates the presence of such FDCs within the B cell follicles (BCFs) where GCs develop as a result of a T cell-dependent antibody response. The activated T cells and APCs drain along the nasal lymphatic pathways and eventually access the cervical lymph nodes.[77] Hence, we observed a complete remodeling of cervical nodes, with B cells centered on GCs and the presence of DCs in close proximity to B cells in these GCs (data not shown). Overall, our results confirm that the S antigen expressed by the delivery of DNA vaccine using AuNS-chitosan shows an effective cell-mediated immunity in the lymph nodes.

Considering the fact that IFNγ has a critical role in recognizing and eliminating pathogens, it has been identified as a prognostic marker for vaccine response. Type I IFNs are pleiotropic antiviral cytokines that can affect nearly every step of the immune response to SC2 vaccination, ranging from S protein expression, DC activation, to T cell differentiation. Unsurprisingly, type I IFNs have been found to be central mediators of T and B cell responses to SC2 vaccines. We also noticed an increased expression of INFγ by T cells in the lymph nodes and blood (FIGS. 17A-17E).[78] The increase in splenic CD8+ T cells expressing IFNγ, which is a signature cytokine of both innate and adaptive immune systems, was evident only in SC2 vaccinated mice but not the pDNA-control vector treated mice.

AuNS-chitosan showed a robust delivery of FLuc mRNA in the lungs of mice upon IN delivery as measured using bioluminescence imaging.

Figure 14A:
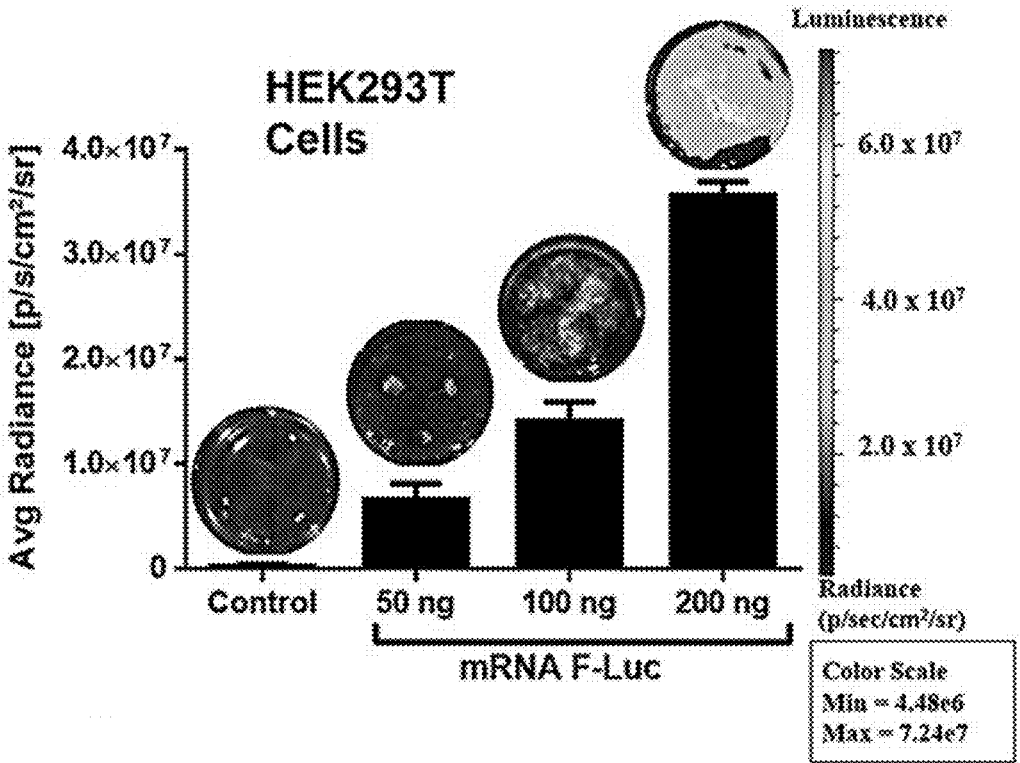
Figure 14B:
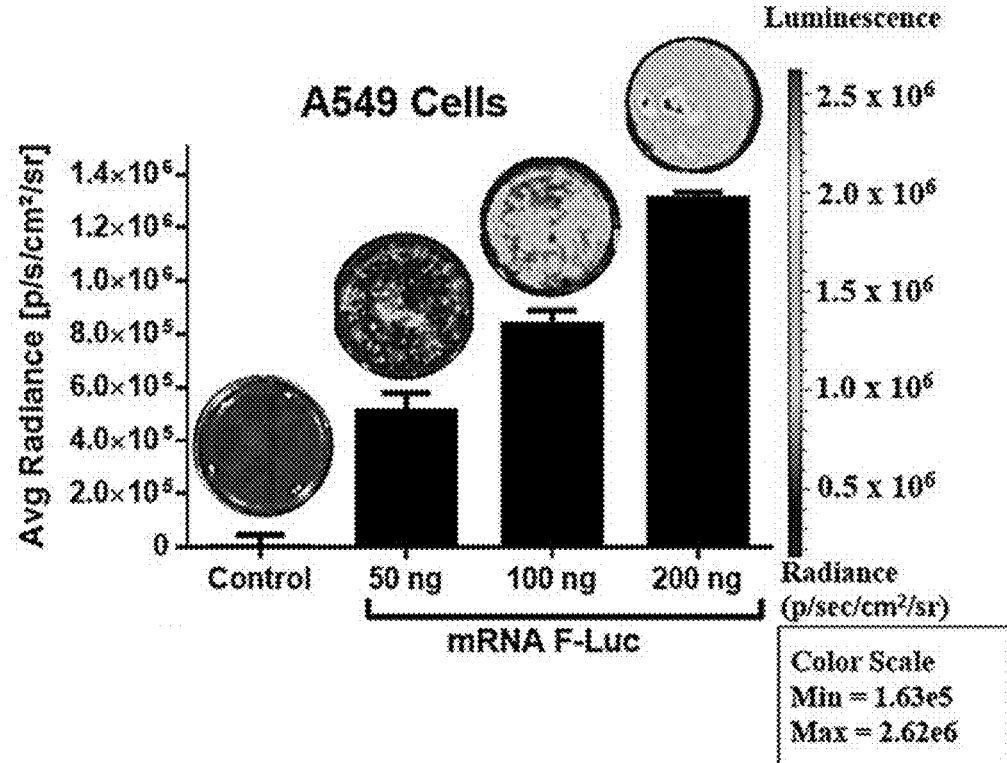
Figure 14C:
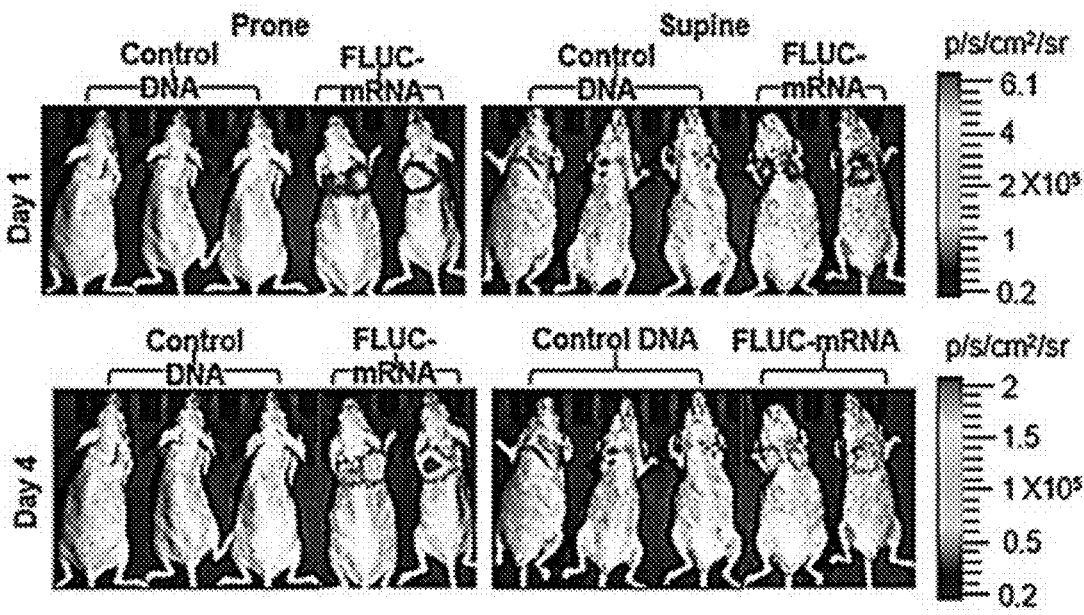
Figure 14D:
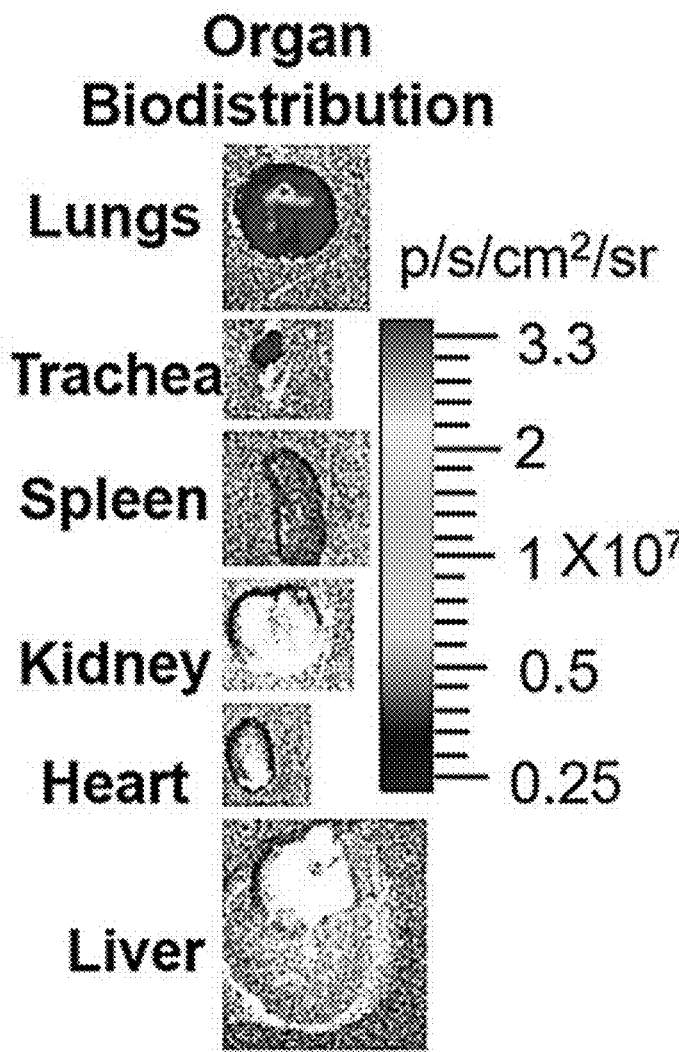

As the IN delivery of DNA vaccine was successful in achieving significant expression and in inducing a pulmonary immune response, we further evaluated the stability and expression of mRNA delivered using AuNS-chitosan in cells, and upon IN delivery in mice using BLI. We used mRNA coding for FLuc reporter gene for this proof-of principle study component. The in vitro results in HEK-293T and A549 cells using the optimal N/P ratio complex transfected with different mRNA concentrations (50, 100, and 200 ng) demonstrated a dose-dependent luciferase expression in both cell types (FIGS. 14A-14B). We used the optimal AuNS-chitosan-FLuc-mRNA complex for IN delivery in mice; 5 µL of NP complex four times in each nostril (a total of 20 µL for each dose; 2 µg of mRNA equivalent). We used 3 mice each for the treatments and controls. We delivered AuNS-chitosan-mRNA, obtained BLI every 24 h after delivery, and continued the dosage every day for three days. Three days after the final dose, the mice were imaged for in vivo bioluminescence signal, and were then sacrificed for ex vivo biodistribution in tissues. The mice revealed strong BLI signals in the lungs (FIG. 14C). Ex vivo analysis (lungs, spleen, liver, trachea, and kidneys) showed strong BLI signals in lungs and tracheobronchial junctions. Signal was absent from other organs, including spleen (FIG. 14D). These findings clearly supported the efficiency of AuNS-chitosan for in vitro and in vivo delivery of synthetic mRNA, and also the stability and functional efficiency of mRNA for in vivo applications.

Conclusion

We evaluated the potential advantages of IN delivery of a novel SC2 vaccine using DNA coding for its S protein as antigen. The delivery of DNA vaccine using AuNS-chitosan NPs yields successful expression of this antigen in respiratory mucosa and lungs of mice, which leads to recruitment of antigen presenting DCs to the lungs and an enhanced humoral antibody response. The antibody response develops as early as 1 week after the IN delivery of three doses of DNA vaccine. The antibody levels were consistently elevated for several weeks without a significant decline, as demonstrated in two different mouse models (BALB/c and C57BL/6J-DR). The antibody response results in high levels of IgG and IgA, which show a strong neutralizing effect against pseudoviruses expressing different spike variants of SC2 (Wuhan, D614G and SA mutant). Additional evaluation using immunostaining-based FACS and confocal microscopy for cell-mediated immune response shows an effective activation of T and B cell responses in the lungs and lymph nodes, which are similar to immune responses normally observed against infectious diseases. Our findings highlight the merits of using AuNS-chitosan as an efficient in vitro and in vivo nanoformulation to deliver DNA and synthetic mRNA, and also its role in stabilizing nucleic acids for functional in vivo transfection for future mRNA vaccine development and applications. This proof-of-principle study highlights the capabilities of this IN SC2 DNA vaccine to yield a strong mucosal immune response, and to also provide a roadmap for the use of mRNA vaccines coding for different antigens of SC2 (N, E, M and S proteins). This may result in a long-lasting, wide spectrum antibody response to combat the large number of SC2 variants distributed around the world, and which are continuously evolving.

Materials and Methods

Materials

We purchased TritonX-100, tetrachloroauric acid, sodium borohydride (NaBH₄), ascorbic acid (AA), silver nitrate (AgNO₃) from Sigma-Aldrich; and gold(III) chloride trihydrate (HAuCl₄·3H₂O), L(+)-ascorbic acid (AA), trisodium citrate dihydrate, 1N hydrochloric acid solution (HCl), chitosan, and phosphate buffered saline (PBS) from Sigma-Aldrich (St Louis, MO) at the highest purity grade available. We used double-distilled water in all preparations. Carbon-coated copper TEM grids were obtained from VWR (Radnor, PA). We pretreated the glassware used for the synthesis of gold NPs in aqua regia for 30 min, then washed and cleaned with double-distilled water under ultrasonication (3 min) thrice.

Methods

Synthesis of AuNS

We synthesized gold nanostar octapods using a modified seed assisted growth of gold nanostars synthesis procedure, as reported previously.[20] In brief, gold nanoseeds were generated from $AuCl_4$—by means of $NaBH_4$, in 0.15 M TritonX-100 and the resultant colloidal gold was used as seeds for nanostar growth. 5 μL of seed gold NPs were added to 5 mL of an aqueous solution containing 0.1 M TritonX-100 and 250 μL of 0.004 M $AgNO_3$ in water. Approximately 5 mL of $HAuCl_4$ (0.001 M) was then supplemented to the resulting mixture and stirred for 30 min at 70° C. After completing homogenous dissolution of all components, we lowered the solution temperature to 37° C. and added 400 μL of 0.0788 M ascorbic acid in an aqueous solution. We stirred the aqueous solution for 30 min and further added 0.6 mL of a previously ice-cooled solution of 0.001 M $NaBH_4$ solution dropwise. The mixture was constantly agitated at 1000 rpm, resulting in a homogenous suspension that subsequently changed to intense green, and at this point the reaction was stopped by reducing the temperature to −4° C. The resultant gold nanostars were separated by centrifugation at 13,000 rpm for 30 min and wash thrice with distilled water before using in further in vitro and in vivo studies.

Formulation of SC2 Plasmid or pcDNA Loaded AuNS.

The chitosan dissolved in 0.2% acetic acid was microfluidized using a LV1-microfluidics system (Microfluidics, Westwood, MA) at 30,000 psi. We extracted the suspension of chitosan at the outlet at a 0.5 mg/mL concentration and used this for coating the AuNS. We then incubated the solubilized chitosan with 400 μL (stock—5 mg/mL) AuNS in a rotary incubator at 200 rpm overnight at 30° C. Prior to co-incubation, as-prepared Au nanostars were dispersed in sterile double-distilled water by brief probe sonication, i.e., 5 s "On" amplitude 40%, to form a 5 mg/mL uniform suspension of NPs. After the overnight incubation, we subjected the reaction mixture to centrifugal separation at 13,000 rpm for 30 min and the resultant pellet was pooled together in a stipulated volume of 600 μL sterile double-distilled water. We used a stock SC2 plasmid (2 μg) diluted to 200 ng/μL in DEPC water and complexed with increasing amount of chitosan capped AuNS, and then incubated at 37° C. for 15 min. The complexes were loaded on 0.7% agarose gel and the electrophoresis run at 40 V for 45 min. After the run, the gel was imaged in BioRad Gel Doc XR+ Gel Documentation system (Bio Rad, Hercules, CA, USA) to further quantify and analyze the extent of DNA encapsulation. The optimized SC2 plasmid or pcDNA loaded AuNS-chitosan was adapted for subsequent in vitro and in vivo studies. The plasmid DNA loaded complexes were administered in 20 μL dosages at each time point of study.

Nanoparticle Characterization.

We characterized each step of AuNS surface modification during the synthesis procedure for mean hydrodynamic diameters and zeta potential using dynamic light scattering (DLS) in a Malvern Zetasizer Nano Z system at 25° C. with a scattering angle of 90°. We determined the ζ-potential (surface charge) of the AuNS based NPs using Smoluchowski approximation. We prepared samples in PBS and diluted with deionized water to ensure that the measurements were performed under conditions of low ionic strength where the surface charge of the particles can be measured accurately. We characterized the particle size and morphology of the AuNS-chitosan loaded with SC2 plasmid using transmission electron microscopy (TEM, FEI-Tecnai G2 F20 X-TWIN). Images were acquired using an ORIUS CCD camera through digital micrography, and energy dispersive X-ray spectra (EDS) were recorded through the FEI-TIA interface. For sample preparation, 10 μL of AuNS-chitosan loaded with SC2 plasmid were drop casted on glow discharged copper grids with pure carbon support film, and incubated for 10-15 min and then washed with ultrapure water.

In Vitro Evaluation of AuNS-Chitosan Mediated DNA Transfection in Cells.

We estimated cellular uptake and FLuc plasmid delivery by AuNS-chitosan quantitatively using BLI. The A549 cells were treated with FLuc EGFP (1 μg) plasmid loaded on AuNS-chitosan. At 48 h we imaged the treated cells for bioluminescence signal using an IVIS Lumina-III In Vivo Imaging System in the presence of D-Luc (150 μg/mL) substrate. The bioluminescence signal was quantified for all treatment conditions to draw clear correlations.

Mice Strains and Immunizations.

We purchased 6-8 weeks old BALB/c female mice, from Charles River Laboratories (Wilmington, MA); and C57BL/6J mice, as well as mice carrying the $Ccr2^{RFP}Cx3cr1^{GFP}$ dual-reporter from the Jackson Laboratory (Bar Harbor, ME). Mice were maintained under specific pathogen-free conditions. We performed all animal experiments under the guidance of the Administrative Panel on Laboratory Animal Care (APLAC) of our university. We immunized mice IN with 10 μg of SC2 DNA or pcDNA vaccine in solution. We performed the IN delivery of the NP formulation in mice under mild sedation, using isoflurane gas anesthesia, to enable animal recovery within a couple of minutes. We placed each mouse in an induction chamber and adjusted the oxygen flowmeter to 0.8-1.5 L/min. Once a steady breathing rate was established, we administered 20 μL of the nano-formulation IN as 5 μL/drop over 15-20 min. After administering each drop, we stopped for 3-4 min to ensure the animal inhaled the drop and that it was breathing at a steady rate. The nostrils were observed closely for signs of blockage or irritation. After administering the full dose, each animal was allowed to recover from anesthesia before transfer to its cage.

Serum Neutralization Assay with Pseudotyped Lentivirus.

Virus neutralization by antibodies is an important prognostic factor in many viral diseases. To easily and rapidly measure titers of neutralizing antibodies in serum or plasma, we developed pseudovirion particles. The SC2 spike D614G pseudotyped lentiviruses were produced using SC2 Spike (Genbank Accession #QHD43416.1; with D614G mutation) as the envelope glycoproteins instead of the commonly used VSV-G. These pseudovirions contain the FLuc gene driven by a CMV promoter; therefore, the spike-mediated cell entry can be conveniently determined via FLuc imaging. The SC2 Spike D614G pseudotyped lentivirus can be used to measure the activity of neutralizing antibody against SC2 in a Biosafety Level 2 facility. A variant called B.1.351 was first identified in the fall of 2020 in the Republic of South Africa. This South African variant, also known as 501Y.V2, has many mutations which may lead to higher transmissibility and infectivity. The Spike (B.1.351 Variant) (SC2) pseudotyped lentiviruses were produced using SC2 B.1.351 Variant Spike (Genbank Accession #QHD43416.1 with B.1.351 mutations; as the envelope glycoproteins instead of the commonly used VSV-G.

We seeded HEK293T-ACE2 cells in 96-well plates at 5×10^4 cells per well the day prior to infection. WE seeded HEK293FT and HEK293T-ACE2 cells in 96-well plates (ThermoFisher, US) the day before infection. Pseudotyped MLV viruses were added to the pre-cultured cells. We cultured cells at 37° C. with 5% $CO_2$ for 2 days. All cells in each well were assayed for luciferase expression levels in the presence of D-Luc substrate. After validating the ACE2 receptor specific transfection of pseudovirus, we evaluated its infectivity in the presence of animal serum. We serially diluted sera in a volume of 50 μL using DMEM with 10% FBS, 2 mM L-glutamine and 200 μg/mL hygromycin B as diluent, and pre-incubated with 50 μL of pseudotyped viruses at 37° C. for 1 h. For these infections, virus stocks were used at a dilution in the absence of serum. Cells were then infected with the serum/pseudovirion mixtures. Luciferase was measured 48 h post infection using D-Luc substrate. We plotted neutralization titers using Prism 8 (GraphPad, US).

Measurement of SPK-Specific IgG, IgM and IgA Antibodies in Peripheral Blood.

We drew blood from the tail of each mouse from all five groups, two days before the first immunization, 12 days after the first and second immunizations, and 15 days after the last immunization, to evaluate the humoral immune response. The blood was centrifuged, and serum isolated for specific IgG, IgM and IgA detection by enzyme-linked immunosorbent assay (ELISA). Briefly, we coated 96-well plates (Maxisorp, Nunc) with 50 μL of 5 μg/mL SPK peptide in phosphate buffered saline (PBS) overnight at 4° C. Plates were blocked with 100 μL of 1% bovine serum albumin in PBS for 2 h at room temperature. We diluted serum from individual mice to 1:1600 or 1:400, added to wells, and incubated for 1 h at room temperature. After washing it three times with PBST, we incubated the plates for 1 h at room temperature with secondary antibodies rabbit anti-mouse IgG, IgA or IgM (1:2000), conjugated to horseradish peroxidase (Serotec, Oxford, UK). Then we added 200 μL of the substrate TMB (3,3',5,5'-Tetramethylbenzidine)/$H_2O_2$ (BD Biosciences, San Jose, CA, USA) and incubated in the dark for 30 min at room temperature, and the reaction was stopped by adding 50 μL $H_2SO_4$ 2N. The plates were read at OD450 nm using Tecan Spectrophotometer, and antibody titers were expressed as mean absorbance±standard deviation (SD).

Immunoblot Analysis.

To determine the expression of SPK protein in transfected cells and screen the specificity of SC2 antibody against mutant variants of SC2 with respect to purified SPK proteins, we performed immunoblot analysis using anti-SC2 SPK antibody. We seeded 500,000 HEK293 cells in 10 cm well plates and transfected with 10 μg pDNA (pcDNA, SC2-Wuhan, SC2-SA-mutant, and SC2-D614G-mutant) using Lipofectamine™ 3000 reagent (Thermo Fisher Scientific) and after 48 h treatment, we harvested and processed cells further for immunoblot analysis using anti-SPK antibody. In brief, we lysed cells in 500 μL lysis buffer, and mixed 100 μg of total protein with β-mercaptoethanol (Bio-Rad) and 10 μL of NuPAGE™ LDS (4X) loading buffer, heated at 95° C. for 5 min, and loaded in 4-12% SDS-polyacrylamide gel electrophoresis gradient gel (Invitrogen) and run at 80 V for 2 h. The resolved proteins from the gel were then electroblotted onto a 0.2 um pore size nitrocellulose membrane (Schleicher & Schuell, Keene, NH, USA). The membrane was blocked with 5% non-fat dry milk in tris-buffered saline containing 0.01% Tween™-20 (TBS-T, pH 7.6) for 30 min and incubated with the anti-rabbit SPK monoclonal antibody overnight at 4° C. on a rocking platform. On the following day, we washed away the primary antibody using PBST, added peroxidase conjugated goat anti-rabbit IgG secondary antibody (1:10 000 dilution, Rockland Immunochemicals, Gilbersville, PA, USA), and allowed this to rock for 2 h at room temperature. The blots were developed with Pierce ECL Western Blotting Substrate (Thermo Fisher Scientific, USA) and imaged and quantified with the IVIS™ Lumina III In-Vivo Imaging System.

Histology of Lungs, Spleen, and Lymph Nodes.

We performed cardiac perfusion of animals under deep anesthesia to harvest the organs for histology. Briefly, under anesthesia we dissected each mouse below the diaphragm and cut the rib cage to expose the heart. We made a left ventriculotomy and inserted a needle into the aorta and clamped, and then cut the right atrium to allow flow. Each animal was transcardially perfused using 30 mL PBS for 4-5 min or until the liver was cleared of blood. Next, to preserve tissue morphology and retain the antigenicity of the target molecules, we perfused the animal with 30 mL 4% paraformaldehyde for 4 min. Following aldehyde fixation, we harvested the tissues (spleen, lymph nodes, and lungs), transferred into 30% sucrose in PBS for overnight equilibration, and then processed for OCT embedding. The OCT blocks were sectioned at 5 μm thick tissue sections using a cryostat and thaw-mounted onto gelatin-coated histological slides. We then dried the slides for 30 min at 37° C. and rehydrated in a wash buffer for 10 min. The tissues were blocked using 1% bovine serum albumin in PBS for 30 min at room temperature and then incubated with antigen specific anti-mouse fluorophore tagged antibody (CD4-FITC, CD8-Alexa™-700, CD19 Alexa™-700) and incubated overnight at 2-8° C. After the incubation time, we washed the antibodies three times for 15 minutes in wash buffer. We then incubated the slides in 300 μL of the diluted solution of Hoechst 33342 and incubated for 5 min at room temperature. The slide were finally rinsed once with PBS and mounted with an anti-fade mounting media and visualized using a Leica DMi8 confocal microscope under respective filters.

Flow cytometry immunophenotyping: We performed cell surface marker based immune cell analysis using flow cytometry for lungs, spleen, lymph nodes, thymus, and blood samples. Briefly, we prepared single-cell suspensions from tissues using mechanical dissociation, and red blood cells were removed using ACK lysing buffer. After the final wash, we filtered cells through a 70-um cell strainer and viability was checked using 0.1% trypan blue. One million cells were labeled with cell surface marker specific anti-mouse antibody labelled with fluorochrome, i.e., CD45-Pac-Blue, CD3/CD4/CD8 PE-CY7/FITC/Alexa™-700, CD45/CD11b PacBlue/APC-Cy7, CD45/CD11c PacBlue/PE-Cy7, CD45/CD86 Pac Blue/PE, CD19 Alexa™-700, CD22 Alexa™-700 (Biolegend). Isotype antibodies were included for gating and compensation. Following addition of antibodies, we kept cells in the dark for 30 min. We washed cells using PBS and suspended in fresh PBS, then analyzed for 20,000 events using a Guava® easyCyte™ Flow Cytometer.

Statistical analyses: We used GraphPad Prism 8 (version 8.0a; GraphPad Soft-ware, Inc., La Jolla, CA, USA) to plot all graphs and perform statistical analyses. We pooled data from 3-5 mice from independent experiments and presented results as mean±standard deviation (SD) or standard errors of means (SEM), as indicated in the figure legends, and interquartile range between the first (25th percentile) and third (75th percentile) was adopted for analysis. We compared grouped data using two-tailed Students t-test and calculated multiple comparisons of grouped data. For correlation analysis between ELISA and neutralization titers, significance (p) were calculated using Prism 9.0 (Graphpad).

Differences were considered significant when p values were less than 0.05. p values if not indicated in corresponding figure legends denote level of significance (* denotes $0.01 < p < 0.05$,  denotes $0.001 < p < 0.01$, * denotes $0.0001 < p < 0.001$, and **** denotes $p < 0.0001$).

Tables

TABLE 1

Complex size and surface characteristics. Size is shown in diameter. For complexes without outer layer and/or nucleic acid, size is shown for the nanoparticle core.

| Category | Size (nm) | Polydispersity Index (PDI) | Zeta Potential (mV) |
|---|---|---|---|
| AuNS-Large | 69.8 | 0.304 | −17.5 |
| AuNS-Large-CD-CS | 158.9 | 0.285 | +34.0 |
| AuNS-Large-CD-CS-DNA | 215.6 | 0.368 | +20.3 |
| AuNS-Small | 50.2 | 0.332 | −16.2 |
| AuNS-Small-CD-CS | 143.7 | 0.265 | +38.1 |
| AuNS-Small-CD-CS-DNA | 282.2 | 0.329 | +12.8 |
| AuNP-Sphere | 45.8 | 0.298 | −18.5 |
| AuNP-Sphere-CD-CS | 137.6 | 0.308 | +35.0 |
| AuNP-Sphere-CD-CS-DNA | 202.6 | 0.388 | +25.4 |

TABLE 2

Viruses and antigens targeted by the complexes provided herein.

| Virus | Principal Syndromes | Viral antigen targets for vaccine | Accession Number |
|---|---|---|---|
| Human respiratory syncytial virus (HRSV) | Upper respiratory infection (URI), bronchiolitis, croup, bronchitis, pneumonia | Glycoprotein G (receptor binding), Glycoprotein F (membrane fusion), and Glycoprotein SH | M74568.1 |
| Human parainfluenza virus (HPV) | URI, croup, bronchiolitis, bronchitis, pneumonia | HN-Tetramer, F-Protein trimer, Matrix protein (M) | NC_021928.1 |
| Human rhinovirus (HRV) | URI; asthma and COPD exacerbation | Viral capsid glycoproteins (VP1, VP2, VP3 and VP4) | FJ445170.1 |
| Adenovirus (ADV) | URI, PCF, bronchitis, pneumonia | Hexon, Penton, Fiber, IIIa, VIII, and IX | J01917.1 |
| Human coronavirus (HCoV) | URI, bronchitis, pneumonia | Envelop, Membrane, Spike Protein and Nucleocapsid protein | KX344031.1 |
| Coronavirus associated with SARS (SARS-CoV) | SARS | Envelop, Membrane, Spike Protein and Nucleocapsid protein | AY323977.2 |
| Human metapneumovirus (HMPV) | URI, bronchitis, pneumonia | Glycoprotein-G, Fusion protein-F, Nucleoprotein-N, SH-Protein, Matrix protein | MN867464.1 |
| Human bocavirus (HBoV) | URI, bronchiolitis, asthma exacerbation, bronchitis, pneumonia | Viral capsid proteins 1 and 2 (VP1 and VP2) | KP710213.1 |

REFERENCES FOR EXAMPLES 1-4

1. Hoffmann, M.; Kleine-Weber, H.; Schroeder, S.; Kruger, N.; Herrler, T.; Erichsen, S.; Schiergens, T. S.; Herrler, G.; Wu, N. H.; Nitsche, A.; Muller, M. A.; Drosten, C.; Pohlmann, S., SARS-CoV-2 Cell Entry Depends on ACE2 and TMPRSS2 and Is Blocked by a Clinically Proven Protease Inhibitor. *Cell* 2020, 181 (2), 271-280 e8.
2. Verdecchia, P.; Cavallini, C.; Spanevello, A.; Angeli, F., The pivotal link between ACE2 deficiency and SARS-CoV-2 infection. *Eur J Intern Med* 2020, 76, 14-20.
3. Zhang, H.; Penninger, J. M.; Li, Y.; Zhong, N.; Slutsky, A. S., Angiotensin-converting enzyme 2 (ACE2) as a SARS-CoV-2 receptor: molecular mechanisms and potential therapeutic target. *Intensive Care Med* 2020, 46 (4), 586-590.
4. Shang, J.; Wan, Y.; Luo, C.; Ye, G.; Geng, Q.; Auerbach, A.; Li, F., Cell entry mechanisms of SARS-CoV-2. *Proc Natl Acad Sci USA* 2020, 117 (21), 11727-11734.
5. Grifoni, A.; Weiskopf, D.; Ramirez, S. I.; Mateus, J.; Dan, J. M.; Moderbacher, C. R.; Rawlings, S. A.; Sutherland, A.; Premkumar, L.; Jadi, R. S.; Marrama, D.; de Silva, A. M.; Frazier, A.; Carlin, A. F.; Greenbaum, J. A.; Peters, B.; Krammer, F.; Smith, D. M.; Crotty, S.; Sette, A., Targets of T Cell Responses to SARS-CoV-2 Coronavirus in Humans with COVID-19 Disease and Unexposed Individuals. *Cell* 2020, 181 (7), 1489-1501 e15.
6. Amanat, F.; Krammer, F., SARS-CoV-2 Vaccines: Status Report. *Immunity* 2020, 52 (4), 583-589.
7. Mona Fani; Ali Teimoori; Ghafari., S., Comparison of the COVID-2019 (SARS-CoV-2) pathogenesis with SARS-CoV and MERS-CoV infections. *Future Virol.* 2020, (10.2217/fvl-2020-0050.).
8. Graham, R. L.; Donaldson, E. F.; Baric, R. S., A decade after SARS: strategies for controlling emerging coronaviruses. *Nat Rev Microbiol* 2013, 11 (12), 836-48.
9. Yang, Z. Y.; Kong, W. P.; Huang, Y.; Roberts, A.; Murphy, B. R.; Subbarao, K.; Nabel, G. J., A DNA vaccine induces SARS coronavirus neutralization and protective immunity in mice. *Nature* 2004, 428 (6982), 561-4.
10. Jiang, S.; He, Y.; Liu, S., SARS vaccine development. *Emerg Infect Dis* 2005, 11 (7), 1016-20.
11. Widjaja, I.; Wang, C.; van Haperen, R.; Gutierrez-Alvarez, J.; van Dieren, B.; Okba, N. M. A.; Raj, V. S.; Li, W.; Femandez-Delgado, R.; Grosveld, F.; van Kuppeveld, F. J. M.; Haagmans, B. L.; Enjuanes, L.; Drabek, D.; Bosch, B. J., Towards a solution to MERS: protective human monoclonal antibodies targeting different domains and functions of the MERS-coronavirus spike glycoprotein. *Emerg Microbes Infect* 2019, 8 (1), 516-530.

12. Kim, M. H.; Kim, H. J.; Chang, J., Superior immune responses induced by intranasal immunization with recombinant adenovirus-based vaccine expressing full-length Spike protein of Middle East respiratory syndrome coronavirus. *PLoS One* 2019, 14 (7), e0220196.

13. Liu, W. J.; Zhao, M.; Liu, K.; Xu, K.; Wong, G.; Tan, W.; Gao, G. F., T-cell immunity of SARS-CoV: Implications for vaccine development against MERS-CoV. *Antiviral Res* 2017, 137, 82-92.

14. Jiang, S.; Du, L.; Shi, Z., An emerging coronavirus causing pneumonia outbreak in Wuhan, China: calling for developing therapeutic and prophylactic strategies. Emerg *Microbes Infect* 2020, 9 (1), 275-277.

15. Shi, J.; Zhang, J.; Li, S.; Sun, J.; Teng, Y.; Wu, M.; Li, J.; Li, Y.; Hu, N.; Wang, H.; Hu, Y., Epitope-Based Vaccine Target Screening against Highly Pathogenic MERS-CoV: An In Silico Approach Applied to Emerging Infectious Diseases. *PLoS One* 2015, 10 (12), e0144475.

16. Xie, Q.; He, X.; Yang, F.; Liu, X.; Li, Y.; Liu, Y.; Yang, Z.; Yu, J.; Zhang, B.; Zhao, W., Analysis of the Genome Sequence and Prediction of B-Cell Epitopes of the Envelope Protein of Middle East Respiratory Syndrome-Coronavirus. *IEEE/ACM Trans Comput Biol Bioinform* 2018, 15 (4), 1344-1350.

17. Alberer M, G.-V. U., Hong HS, Mehr K T, Backert L, Finak G, et al., Safety and immunogenicity of a mRNA rabies vaccine in healthy adults: an open-label, non-randomised, prospective, first-in-human phase 1 clinical trial.. *Lancet* 2017, 390, 1511-20.

18. Bahl K, S. J., Yuzhakov O, Bulychev A, Brito L A, Hassett K J, et al; Preclinical and Clinical Demonstration of Immunogenicity by mRNA Vaccines against H10N8 and H7N9 Influenza Viruses. *Mol Ther* 2017, 25, 1316-27.

19. Sakhatskyy, P.; Wang, S.; Chou, T. H.; Lu, S., Immunogenicity and protection efficacy of monovalent and polyvalent poxvirus vaccines that include the D8 antigen. Virology 2006, 355 (2), 164-74.

20. Schlingmann, B.; Castiglia, K. R.; Stobart, C. C.; Moore, M. L., Polyvalent vaccines: High-maintenance heroes. *PLoS Pathog* 2018, 14 (4), e1006904.

21. Sukumar, U. K.; Bose, R. J. C.; Malhotra, M.; Babikir, H. A.; Afjei, R.; Robinson, E.; Zeng, Y.; Chang, E.; Habte, F.; Sinclair, R.; Gambhir, S. S.; Massoud, T. F.; Paulmurugan, R., Intranasal delivery of targeted polyfunctional gold-iron oxide nanoparticles loaded with therapeutic microRNAs for combined theranostic multimodality imaging and presensitization of glioblastoma to temozolomide. *Biomaterials* 2019, 218, 119342.

22. Thakor, A. S.; Paulmurugan, R.; Kempen, P.; Zavaleta, C.; Sinclair, R.; Massoud, T. F.; Gambhir, S. S., Oxidative stress mediates the effects of Raman-active gold nanoparticles in human cells. *Small* 2011, 7 (1), 126-36.

23. Thakor, A. S.; Luong, R.; Paulmurugan, R.; Lin, F. I.; Kempen, P.; Zavaleta, C.; Chu, P.; Massoud, T. F.; Sinclair, R.; Gambhir, S. S., The fate and toxicity of Raman-active silica-gold nanoparticles in mice. *Sci Transl Med* 2011, 3 (79), 79ra33.

24. Thakor, A. S.; Jokerst, J.; Zavaleta, C.; Massoud, T. F.; Gambhir, S. S., Gold nanoparticles: a revival in precious metal administration to patients. *Nano Lett* 2011, 11 (10), 4029-36.

25. Dwivedy, A.; Aich, P., Importance of innate mucosal immunity and the promises it holds. *Int J Gen Med* 2011, 4, 299-311.

26. Ho, M.; Pastan, I., Mammalian cell display for antibody engineering. *Methods Mol Biol* 2009, 525, 337-52, xiv.

27. Zhou, C.; Jacobsen, F. W.; Cai, L.; Chen, Q.; Shen, W. D., Development of a novel mammalian cell surface antibody display platform. *MAbs* 2010, 2 (5), 508-18.

REFERENCES FOR EXAMPLES 5

1. Harapan, H.; Itoh, N.; Yufika, A.; Winardi, W.; Keam, S.; Te, H.; Megawati, D.; Hayati, Z.; Wagner, A. L.; Mudatsir, M., Coronavirus disease 2019 (COVID-19): A literature review. *J Infect Public Health* 2020, 13 (5), 667-673.

2. Krammer, F., SARS-CoV-2 vaccines in development. *Nature* 2020, 586 (7830), 516-527.

3. Arashkia, A.; Jalilvand, S.; Mohajel, N.; Afchangi, A.; Azadmanesh, K.; Salehi-Vaziri, M.; Fazlalipour, M.; Pouriayevali, M. H.; Jalali, T.; Mousavi Nasab, S. D.; Roohvand, F.; Shoja, Z.; Iran, S. C.-R. R. T. o. P. I. o., Severe acute respiratory syndrome-coronavirus-2 spike (S) protein based vaccine candidates: State of the art and future prospects. *Rev Med Virol* 2020, e2183.

4. Bettini, E.; Locci, M., SARS-CoV-2 mRNA Vaccines: Immunological Mechanism and Beyond. *Vaccines (Basel)* 2021, 9 (2).

5. Schlake, T.; Thess, A.; Fotin-Mleczek, M.; Kallen, K. J., Developing mRNA-vaccine technologies. *RNA Biol* 2012, 9 (11), 1319-30.

6. Hassan, A. O.; Kafai, N. M.; Dmitriev, I. P.; Fox, J. M.; Smith, B. K.; Harvey, I. B.; Chen, R. E.; Winkler, E. S.; Wessel, A. W.; Case, J. B.; Kashentseva, E.; McCune, B. T.; Bailey, A. L.; Zhao, H.; VanBlargan, L. A.; Dai, Y. N.; Ma, M.; Adams, L. J.; Shrihari, S.; Danis, J. E.; Gralinski, L. E.; Hou, Y. J.; Schafer, A.; Kim, A. S.; Keeler, S. P.; Weiskopf, D.; Baric, R. S.; Holtzman, M. J.; Fremont, D. H.; Curiel, D. T.; Diamond, M. S., A Single-Dose Intranasal ChAd Vaccine Protects Upper and Lower Respiratory Tracts against SARS-CoV-2. *Cell* 2020, 183 (1), 169-184 e13.

7. Zuckerman, J. N., The importance of injecting vaccines into muscle. Different patients need different needle sizes. *BMJ* 2000, 321 (7271), 1237-8.

8. Ho, W.; Gao, M.; Li, F.; Li, Z.; Zhang, X. Q.; Xu, X., Next-Generation Vaccines: Nanoparticle-Mediated DNA and mRNA Delivery. *Adv Healthc Mater* 2021, 10 (8), e2001812.

9. Suhail, M.; Rosenholm, J. M.; Minhas, M. U.; Badshah, S. F.; Naeem, A.; Khan, K. U.; Fahad, M., Nanogels as drug-delivery systems: a comprehensive overview. *Ther Deliv* 2019, 10 (11), 697-717.

10. Prego, C.; Paolicelli, P.; Diaz, B.; Vicente, S.; Sanchez, A.; Gonzalez-Fernandez, A.; Alonso, M. J., Chitosan-based nanoparticles for improving immunization against hepatitis B infection. *Vaccine* 2010, 28 (14), 2607-14.

11. Mohammed, M. A.; Syeda, J. T. M.; Wasan, K. M.; Wasan, E. K., An Overview of Chitosan Nanoparticles and Its Application in Non-Parenteral Drug Delivery. *Pharmaceutics* 2017, 9 (4).

12. Saenz, L.; Neira-Carrillo, A.; Paredes, R.; Cortes, M.; Bucarey, S.; Arias, J. L., Chitosan formulations improve the immunogenicity of a GnRH-I peptide-based vaccine. *Int J Pharm* 2009, 369 (1-2), 64-71.

13. An, X.; Martinez-Paniagua, M.; Rezvan, A.; Fathi, M.; Singh, S.; Biswas, S.; Pourpak, M.; Yee, C.; Liu, X.;

Varadarajan, N., Single-dose intranasal vaccination elicits systemic and mucosal immunity against SARS-CoV-2. bioRxiv 2020.

14. Chiu, C.; Openshaw, P. J., Antiviral B cell and T cell immunity in the lungs. *Nat Immunol* 2015, 16(1), 18-26.

15. Chen, L.; Wang, J.; Zganiacz, A.; Xing, Z., Single intranasal mucosal *Mycobacterium bovis* BCG vaccination confers improved protection compared to subcutaneous vaccination against pulmonary tuberculosis. *Infect Immun* 2004, 72 (1), 238-46.

16. Davis, S. S., Nasal vaccines. *Adv Drug Deliv Rev* 2001, 51 (1-3), 21-42.

17. Cain, M. D.; Salimi, H.; Gong, Y.; Yang, L.; Hamilton, S. L.; Heffernan, J. R.; Hou, J.; Miller, M. J.; Klein, R. S., Virus entry and replication in the brain precedes blood-brain barrier disruption during intranasal alphavirus infection. *J Neuroimmunol* 2017, 308, 118-130.

18. Kunda, N. K.; Somavarapu, S.; Gordon, S. B.; Hutcheon, G. A.; Saleem, I. Y., Nanocarriers targeting dendritic cells for pulmonary vaccine delivery. *Pharm Res* 2013, 30 (2), 325-41.

19. Tao, W.; Ziemer, K. S.; Gill, H. S., Gold nanoparticle-M2e conjugate coformulated with CpG induces protective immunity against influenza A virus. *Nanomedicine* (Lond) 2014, 9 (2), 237-51.

20. Sukumar, U. K.; Bose, R. J. C.; Malhotra, M.; Babikir, H. A.; Afjei, R.; Robinson, E.; Zeng, Y.; Chang, E.; Habte, F.; Sinclair, R.; Gambhir, S. S.; Massoud, T. F.; Paulmurugan, R., Intranasal delivery of targeted polyfunctional gold-iron oxide nanoparticles loaded with therapeutic microRNAs for combined theranostic multimodality imaging and presensitization of glioblastoma to temozolomide. *Biomaterials* 2019, 218, 119342.

21. Bastus, N. G.; Sanchez-Tillo, E.; Pujals, S.; Farrera, C.; Kogan, M. J.; Giralt, E.; Celada, A.; Lloberas, J.; Puntes, V., Peptides conjugated to gold nanoparticles induce macrophage activation. *Mol Immunol* 2009, 46 (4), 743-8.

22. Watanabe, K.; Watanabe, C.; Honma, T.; Tian, Y. S.; Kawashima, Y.; Kawashita, N.; Takagi, T.; Fukuzawa, K., Intermolecular Interaction Analyses on SARS-CoV-2 Spike Protein Receptor Binding Domain and Human Angiotensin-Converting Enzyme 2 Receptor-Blocking Antibody/Peptide Using Fragment Molecular Orbital Calculation. *J Phys Chem* Lett 2021, 12 (16), 4059-4066.

23. Li, L.; Petrovsky, N., Molecular mechanisms for enhanced DNA vaccine immunogenicity. *Expert Rev Vaccines* 2016, 15 (3), 313-29.

24. Singh, M.; Briones, M.; O'Hagan, D. T., A novel bioadhesive intranasal delivery system for inactivated influenza vaccines. *J Control Release* 2001, 70 (3), 267-76.

25. Dutta, A.; Huang, C. T.; Lin, C. Y.; Chen, T. C.; Lin, Y. C.; Chang, C. S.; He, Y. C., Sterilizing immunity to influenza virus infection requires local antigen-specific T cell response in the lungs. *Sci Rep* 2016, 6, 32973.

26. Zhu, Y.; Yu, D.; Han, Y.; Yan, H.; Chong, H.; Ren, L.; Wang, J.; Li, T.; He, Y., Cross-reactive neutralization of SARS-CoV-2 by serum antibodies from recovered SARS patients and immunized animals. *Sci Adv* 2020, 6 (45).

27. Rappazzo, C. G.; Tse, L. V.; Kaku, C. I.; Wrapp, D.; Sakharkar, M.; Huang, D.; Deveau, L. M.; Yockachonis, T. J.; Herbert, A. S.; Battles, M. B.; O'Brien, C. M.; Brown, M. E.; Geoghegan, J. C.; Belk, J.; Peng, L.; Yang, L.; Hou, Y.; Scobey, T. D.; Burton, D. R.; Nemazee, D.; Dye, J. M.; Voss, J. E.; Gunn, B. M.; McLellan, J. S.; Banc, R. S.; Gralinski, L. E.; Walker, L. M., Broad and potent activity against SARS-like viruses by an engineered human monoclonal antibody. *Science* 2021, 371 (6531), 823-829.

28. Bleul, T.; Zhuang, X.; Hildebrand, A.; Lange, C.; Bohringer, D.; Schlunck, G.; Reinhard, T.; Lapp, T., Different Innate Immune Responses in BALB/c and C57BL/6 Strains following Corneal Transplantation. *J Innate Immun* 2021, 13 (1), 49-59.

29. Mahler, M.; Janke, C.; Wagner, S.; Hedrich, H. J., Differential susceptibility of inbred mouse strains to *Helicobacter pylori* infection. *Scand J Gastroenterol* 2002, 37 (3), 267-78.

30. Skums, P.; Kirpich, A.; Icer Baykal, P.; Zelikovsky, A.; Chowell, G., Global transmission network of SARS-CoV-2: from outbreak to pandemic. medRxiv 2020.

31. Chen, R. E.; Zhang, X.; Case, J. B.; Winkler, E. S.; Liu, Y.; VanBlargan, L. A.; Liu, J.; Errico, J. M.; Xie, X.; Suryadevara, N.; Gilchuk, P.; Zost, S. J.; Tahan, S.; Droit, L.; Turner, J. S.; Kim, W.; Schmitz, A. J.; Thapa, M.; Wang, D.; Boon, A. C. M.; Presti, R. M.; O'Halloran, J. A.; Kim, A. H. J.; Deepak, P.; Pinto, D.; Fremont, D. H.; Crowe, J. E., Jr.; Corti, D.; Virgin, H. W.; Ellebedy, A. H.; Shi, P. Y.; Diamond, M. S., Resistance of SARS-CoV-2 variants to neutralization by monoclonal and serum-derived polyclonal antibodies. *Nat Med* 2021, 27 (4), 717-726.

32. Stamatatos, L.; Czartoski, J.; Wan, Y. H.; Homad, L. J.; Rubin, V.; Glantz, H.; Neradilek, M.; Seydoux, E.; Jennewein, M. F.; MacCamy, A. J.; Feng, J.; Mize, G.; De Rosa, S. C.; Finzi, A.; Lemos, M. P.; Cohen, K. W.; Moodie, Z.; McElrath, M. J.; McGuire, A. T., mRNA vaccination boosts cross-variant neutralizing antibodies elicited by SARS-CoV-2 infection. *Science* 2021.

33. Shang, J.; Wan, Y.; Luo, C.; Ye, G.; Geng, Q.; Auerbach, A.; Li, F., Cell entry mechanisms of SARS-CoV-2. *Proc Natl Acad Sci USA* 2020, 117 (21), 11727-11734.

34. Dhakal, S.; Renu, S.; Ghimire, S.; Shaan Lakshmanappa, Y.; Hogshead, B. T.; Feliciano-Ruiz, N.; Lu, F.; Hogen-Esch, H.; Krakowka, S.; Lee, C. W.; Renukaradhya, G. J., Mucosal Immunity and Protective Efficacy of Intranasal Inactivated Influenza Vaccine Is Improved by Chitosan Nanoparticle Delivery in Pigs. *Front Immunol* 2018, 9, 934.

35. Sterlin, D.; Mathian, A.; Miyara, M.; Mohr, A.; Anna, F.; Claer, L.; Quentric, P.; Fadlallah, J.; Devilliers, H.; Ghillani, P.; Gunn, C.; Hockett, R.; Mudumba, S.; Guihot, A.; Luyt, C. E.; Mayaux, J.; Beurton, A.; Fourati, S.; Bruel, T.; Schwartz, 0.; Lacorte, J. M.; Yssel, H.; Parizot, C.; Dorgham, K.; Charneau, P.; Amoura, Z.; Gorochov, G., IgA dominates the early neutralizing antibody response to SARS-CoV-2. *Sci Transl Med* 2021, 13 (577).

36. Ejemel, M.; Li, Q.; Hou, S.; Schiller, Z. A.; Tree, J. A.; Wallace, A.; Amcheslavsky, A.; Kurt Yilmaz, N.; Buttigieg, K. R.; Elmore, M. J.; Godwin, K.; Coombes, N.; Toomey, J. R.; Schneider, R.; Ramchetty, A. S.; Close, B. J.; Chen, D. Y.; Conway, H. L.; Saeed, M.; Ganesa, C.; Carroll, M. W.; Cavacini, L. A.; Klempner, M. S.; Schiffer, C. A.; Wang, Y., A cross-reactive human IgA monoclonal antibody blocks SARS-CoV-2 spike-ACE2 interaction. *Nat Commun* 2020, 11 (1), 4198.

37. Ejemel, M.; Li, Q.; Hou, S.; Schiller, Z. A.; Wallace, A. L.; Amcheslavsky, A.; Yilmaz, N. K.; Toomey, J. R.; Schneider, R.; Close, B. J.; Chen, D. Y.; Conway, H. L.; Mohsan, S.; Cavacini, L. A.; Klempner, M. S.; Schiffer, C. A.; Wang, Y., IgA MAb blocks SARS-CoV-2 Spike-ACE2 interaction providing mucosal immunity. bioRxiv 2020.

38. Russell, M. W.; Moldoveanu, Z.; Ogra, P. L.; Mestecky, J., Mucosal Immunity in COVID-19: A Neglected but Critical Aspect of SARS-CoV-2 Infection. *Front Immunol* 2020, 11, 611337.

39. Marklund, E.; Leach, S.; Axelsson, H.; Nystrom, K.; Norder, H.; Bemark, M.; Angeletti, D.; Lundgren, A.; Nilsson, S.; Andersson, L. M.; Yilmaz, A.; Lindh, M.; Liljeqvist, J. A.; Gisslen, M., Serum-IgG responses to SARS-CoV-2 after mild and severe COVID-19 infection and analysis of IgG non-responders. *PLoS One* 2020, 15 (10), e0241104.

40. Li, Q.; Wu, J.; Nie, J.; Zhang, L.; Hao, H.; Liu, S.; Zhao, C.; Zhang, Q.; Liu, H.; Nie, L.; Qin, H.; Wang, M.; Lu, Q.; Li, X.; Sun, Q.; Liu, J.; Zhang, L.; Li, X.; Huang, W.; Wang, Y., The Impact of Mutations in SARS-CoV-2 Spike on Viral Infectivity and Antigenicity. *Cell* 2020, 182 (5), 1284-1294 e9.

41. Shah, V. K.; Firmal, P.; Alam, A.; Ganguly, D.; Chattopadhyay, S., Overview of Immune Response During SARS-CoV-2 Infection: Lessons From the Past. *Front Immunol* 2020, 11, 1949.

42. Liu, W. J.; Zhao, M.; Liu, K.; Xu, K.; Wong, G.; Tan, W.; Gao, G. F., T-cell immunity of SARS-CoV: Implications for vaccine development against MERS-CoV. *Antiviral Res* 2017, 137, 82-92.

43. Kopf, M.; Schneider, C.; Nobs, S. P., The development and function of lung-resident macrophages and dendritic cells. *Nat Immunol* 2015, 16 (1), 36-44.

44. Martin, T. R.; Frevert, C. W., Innate immunity in the lungs. *Proc Am Thorac Soc* 2005, 2 (5), 403-11.

45. Kumar, V., Pulmonary Innate Immune Response Determines the Outcome of Inflammation During Pneumonia and Sepsis-Associated Acute Lung Injury. *Front Immunol* 2020, 11, 1722.

46. Lambrecht, B. N.; Prins, J. B.; Hoogsteden, H. C., Lung dendritic cells and host immunity to infection. *Eur Respir J* 2001, 18 (4), 692-704.

47. Martin-Fontecha, A.; Lanzavecchia, A.; Sallusto, F., Dendritic cell migration to peripheral lymph nodes. *Handb Exp Pharmacol* 2009, (188), 31-49.

48. Al-Halifa, S.; Gauthier, L.; Arpin, D.; Bourgault, S.; Archambault, D., Nanoparticle-Based Vaccines Against Respiratory Viruses. *Front Immunol* 2019, 10, 22.

49. Fries, C. N.; Curvino, E. J.; Chen, J. L.; Permar, S. R.; Fouda, G. G.; Collier, J. H., Advances in nanomaterial vaccine strategies to address infectious diseases impacting global health. *Nat Nanotechnol* 2021, 16 (4), 1-14.

50. Nakano, H.; Burgents, J. E.; Nakano, K.; Whitehead, G. S.; Cheong, C.; Bortner, C. D.; Cook, D. N., Migratory properties of pulmonary dendritic cells are determined by their developmental lineage. *Mucosal Immunol* 2013, 6 (4), 678-91.

51. Flaherty, S.; Reynolds, J. M., Mouse Naive CD4+ T Cell Isolation and In vitro Differentiation into T Cell Subsets. *J Vis Exp* 2015, (98).

52. Odak, I.; Barros-Martins, J.; Bosnjak, B.; Stahl, K.; David, S.; Wiesner, O.; Busch, M.; Hoeper, M. M.; Pink, I.; Welte, T.; Comberg, M.; Stoll, M.; Goudeva, L.; Blasczyk, R.; Ganser, A.; Prinz, I.; Forster, R.; Koenecke, C.; Schultze-Florey, C. R., Reappearance of effector T cells is associated with recovery from COVID-19. *EBioMedicine* 2020, 57, 102885.

53. Bousso, P., T-cell activation by dendritic cells in the lymph node: lessons from the movies. *Nat Rev Immunol* 2008, 8 (9), 675-84.

54. Mule, J. J., Dendritic cells: at the clinical crossroads. *J Clin Invest* 2000, 105 (6), 707-8.

55. Weller, S.; Reynaud, C. A.; Weill, J. C., Splenic marginal zone B cells in humans: where do they mutate their Ig receptor? *Eur J Immunol* 2005, 35 (10), 2789-92.

56. Fayette, J.; Durand, I.; Bridon, J. M.; Arpin, C.; Dubois, B.; Caux, C.; Liu, Y. J.; Banchereau, J.; Briere, F., Dendritic cells enhance the differentiation of naive B cells into plasma cells in vitro. *Scand J Immunol* 1998, 48 (6), 563-70.

57. Wykes, M.; Pombo, A.; Jenkins, C.; MacPherson, G. G., Dendritic cells interact directly with naive B lymphocytes to transfer antigen and initiate class switching in a primary T-dependent response. *J Immunol* 1998, 161 (3), 1313-9.

58. Veninga, H.; Borg, E. G.; Vreeman, K.; Taylor, P. R.; Kalay, H.; van Kooyk, Y.; Kraal, G.; Martinez-Pomares, L.; den Haan, J. M., Antigen targeting reveals splenic CD169+ macrophages as promoters of germinal center B-cell responses. *Eur J Immunol* 2015, 45 (3), 747-57.

59. Tozuka, M.; Oka, T.; Jounai, N.; Egawa, G.; Ishii, K. J.; Kabashima, K.; Takeshita, F., Efficient antigen delivery to the lymph nodes is a key component in the immunogenic pathway of the intradermal vaccine. *J Dermatol Sci* 2016, 82 (1), 38-45.

60. Irvine, D. J.; Aung, A.; Silva, M., Controlling timing and location in vaccines. *Adv Drug Deliv Rev* 2020, 158, 91-115.

61. Zhou, X.; Jiang, X.; Qu, M.; Aninwene, G. E., 2nd; Jucaud, V.; Moon, J. J.; Gu, Z.; Sun, W.; Khademhosseini, A., Engineering Antiviral Vaccines. *ACS Nano* 2020, 14 (10), 12370-12389.

62. Faiq, M. A., B-cell engineering: A promising approach towards vaccine development for COVID-19. *Med Hypotheses* 2020, 144, 109948.

63. Louie, D. A. P.; Liao, S., Lymph Node Subcapsular Sinus Macrophages as the Frontline of Lymphatic Immune Defense. *Front Immunol* 2019, 10, 347.

64. Kwak, K.; Akkaya, M.; Pierce, S. K., B cell signaling in context. *Nat Immunol* 2019, 20 (8), 963-969.

65. Buettner, M.; Bode, U., Lymph node dissection—understanding the immunological function of lymph nodes. *Clin Exp Immunol* 2012, 169 (3), 205-12.

66. Mueller, S. N., Spreading the load: Antigen transfer between migratory and lymph node-resident dendritic cells promotes T-cell priming. *Eur J Immunol* 2017, 47 (10), 1798-1801.

67. Pal, I.; Ramsey, J. D., The role of the lymphatic system in vaccine trafficking and immune response. *Adv Drug Deliv Rev* 2011, 63 (10-11), 909-22.

68. van der Poel, C. E.; Bajic, G.; Macaulay, C. W.; van den Broek, T.; Ellson, C. D.; Bouma, G.; Victora, G. D.; Degn, S. E.; Carroll, M. C., Follicular Dendritic Cells Modulate Germinal Center B Cell Diversity through FcgammaRIIB. *Cell Rep* 2019, 29 (9), 2745-2755 e4.

69. Tarlinton, D. M., Immunology: To affinity and beyond. *Nature* 2014, 509 (7502), 573-4.

70. Allen, C. D.; Cyster, J. G., Follicular dendritic cell networks of primary follicles and germinal centers: phenotype and function. *Semin Immunol* 2008, 20 (1), 14-25.

71. Wang, X.; Cho, B.; Suzuki, K.; Xu, Y.; Green, J. A.; An, J.; Cyster, J. G., Follicular dendritic cells help establish follicle identity and promote B cell retention in germinal centers. *J Exp Med* 2011, 208 (12), 2497-510.

72. Tam, H. H.; Melo, M. B.; Kang, M.; Pelet, J. M.; Ruda, V. M.; Foley, M. H.; Hu, J. K.; Kumari, S.; Crampton, J.; Baldeon, A. D.; Sanders, R. W.; Moore, J. P.; Crotty, S.; Langer, R.; Anderson, D. G.; Chakraborty, A. K.; Irvine, D. J., Sustained antigen availability during germinal center initiation enhances antibody responses to vaccination. *Proc Natl Acad Sci USA* 2016, 113 (43), E6639-E6648.

73. Heath, W. R.; Kato, Y.; Steiner, T. M.; Caminschi, I., Antigen presentation by dendritic cells for B cell activation. *Curr Opin Immunol* 2019, 58, 44-52.

74. Kranich, J.; Krautler, N. J., How Follicular Dendritic Cells Shape the B-Cell Antigenome. *Front Immunol* 2016, 7, 225.

75. Dave, R. S.; Jain, P.; Byrareddy, S. N., Follicular Dendritic Cells of Lymph Nodes as Human Immunodeficiency Virus/Simian Immunodeficiency Virus Reservoirs and Insights on Cervical Lymph Node. *Front Immunol* 2018, 9, 805.

76. Hannum, L. G.; Haberman, A. M.; Anderson, S. M.; Shlomchik, M. J., Germinal center initiation, variable gene region hypermutation, and mutant B cell selection without detectable immune complexes on follicular dendritic cells. *J Exp Med* 2000, 192 (7), 931-42.

77. Pichler, W. J.; Wyss-Coray, T., T cells as antigen-presenting cells. *Immunol Today* 1994, 15 (7), 312-5.

78. Kak, G.; Raza, M.; Tiwari, B. K., Interferon-gamma (IFN-gamma): Exploring its implications in infectious diseases. *Biomol Concepts* 2018, 9 (1), 64-79.

What is claimed is:

1. An intranasal vaccine composition comprising complexes of:

(a) a nanoparticle consisting of a gold core coated with an outer layer consisting of a uniform monolayer of a cationic polysaccharide, wherein the cationic polysaccharide is chitosan and the outer layer is covalently attached to the gold core; and (b) a nucleic acid encoding a SARS-CoV-2 S protein, wherein the nucleic acid is attached to said nanoparticle and (c) a pharmaceutically acceptable excipient, wherein the complexes are from about 20 nm to about 80 nm in diameter.

2. The complex of claim 1, comprising a plurality of nucleic acids encoding said pulmonary viral protein or fragment thereof.

3. A method of treating or preventing a pulmonary viral disease in a subject, the method comprising intranasal administration of the pharmaceutical composition of claim 1 to the subject.

4. A method of immunizing a subject susceptible to a pulmonary viral disease, the method comprising intranasal administration of the pharmaceutical composition of claim 1 to the subject.

* * * * *